US00RE49343E

(19) United States
(12) Reissued Patent
Kawamura et al.

(10) Patent Number: US RE49,343 E
(45) Date of Reissued Patent: Dec. 20, 2022

(54) ORGANIC ELECTROLUMINESCENCE DEVICE

(71) Applicant: IDEMITSU KOSAN CO., LTD., Chiyoda-ku (JP)

(72) Inventors: Masahiro Kawamura, Sodegaura (JP); Hirokatsu Ito, Sodegaura (JP); Toshinari Ogiwara, Sodegaura (JP); Yumiko Mizuki, Sodegaura (JP)

(73) Assignee: IDEMITSU KOSAN CO., LTD., Chiyoda-ku (JP)

(21) Appl. No.: 15/668,439

(22) Filed: Aug. 3, 2017

Related U.S. Patent Documents

Reissue of:
(64) Patent No.: 9,099,658
Issued: Aug. 4, 2015
Appl. No.: 13/906,404
Filed: May 31, 2013

(30) Foreign Application Priority Data

Jun. 1, 2012 (JP) ..... 2012-126500
Oct. 3, 2012 (JP) ..... 2012-221701

(51) Int. Cl.

| | |
|---|---|
| ***H01L 35/24*** | (2006.01) |
| ***H01L 51/00*** | (2006.01) |
| ***H01L 51/50*** | (2006.01) |
| ***C07D 209/86*** | (2006.01) |
| ***C09B 57/00*** | (2006.01) |
| ***C09K 11/06*** | (2006.01) |

(52) U.S. Cl.
CPC ..... *H01L 51/0067* (2013.01); *C07D 209/86* (2013.01); *C09B 57/00* (2013.01); *C09K 11/06* (2013.01); *H01L 51/0061* (2013.01); *H01L 51/0072* (2013.01); *H01L 51/5012* (2013.01); *C09K 2211/1007* (2013.01); *C09K 2211/1029* (2013.01); *C09K 2211/1044* (2013.01)

(58) Field of Classification Search
CPC ..... C07D 209/86; C09K 11/06; C09K 2211/1007; C09K 2211/1044; C09K 2211/1029; H01L 51/5012; H01L 51/0061; H01L 51/0067; H01L 51/0072; C09B 57/00
See application file for complete search history.

(56) References Cited

U.S. PATENT DOCUMENTS

| | | | | |
|---|---|---|---|---|
| 7,501,189 | B2 * | 3/2009 | Tokailin | C07C 211/54 313/504 |
| 8,647,754 | B2 * | 2/2014 | Mizuki | C09B 57/00 428/690 |
| 8,652,654 | B2 * | 2/2014 | Inoue | H05B 33/20 428/690 |
| 8,829,783 | B2 * | 9/2014 | Funahashi | C07C 211/58 313/504 |
| 9,130,174 | B2 * | 9/2015 | Mizuki | C07D 403/14 |
| 9,147,847 | B2 * | 9/2015 | Kawamura | C07D 307/79 |
| 9,203,036 | B2 * | 12/2015 | Mizuki | H01L 51/0072 |
| 9,209,406 | B2 * | 12/2015 | Mizutani | C07D 405/14 |
| 9,741,938 | B2 * | 8/2017 | Mizuki | C07D 307/91 |
| 2004/0076853 | A1 * | 4/2004 | Jarikov | C09K 11/06 428/690 |
| 2005/0221124 | A1 | 10/2005 | Hwang et al. | |
| 2006/0051613 | A1 * | 3/2006 | Tomita | H05B 33/14 428/690 |
| 2006/0088728 | A1 * | 4/2006 | Kwong | C07D 209/82 428/690 |
| 2008/0315754 | A1 * | 12/2008 | Kawamura | H05B 33/14 313/504 |
| 2010/0051914 | A1 | 3/2010 | Hwang et al. | |
| 2011/0147718 | A1 | 6/2011 | Howard, Jr. et al. | |
| 2011/0279020 | A1 * | 11/2011 | Inoue | H01L 51/5024 313/504 |
| 2012/0175599 | A1 * | 7/2012 | Yokoyama | C07D 417/14 257/40 |
| 2013/0075716 | A1 * | 3/2013 | Nishimura | H01L 51/5004 257/40 |
| 2013/0214258 | A1 * | 8/2013 | Mizuki | C07D 403/04 257/40 |
| 2013/0264548 | A1 * | 10/2013 | Mizuki | H01L 51/5012 257/40 |

FOREIGN PATENT DOCUMENTS

| | | | | |
|---|---|---|---|---|
| CN | 102709485 | A | 10/2012 | |
| EP | 1 661 888 | A1 | 5/2006 | |
| EP | 2 107 095 | A1 | 10/2009 | |
| EP | 2 169 028 | A2 | 3/2010 | |
| EP | 2 690 681 | A1 | 1/2014 | |
| EP | 2 790 239 | A1 | 10/2014 | |
| JP | 2005/183345 | A | 7/2005 | |
| JP | 2009-518342 | | 5/2009 | |
| JP | 2009-120582 | A | 6/2009 | |
| JP | 2009-123976 | A | 6/2009 | |
| JP | 2010-180204 | | 8/2010 | |
| JP | 2011-222831 | | 11/2011 | |
| JP | WO-2011155507 | * | 12/2011 | H01L 51/50 |
| JP | 2012-079915 | | 4/2012 | |
| TW | 201211003 | A | 3/2012 | |

(Continued)

OTHER PUBLICATIONS

European Office Action dated Mar. 19, 2018 in European Patent Appiication No. 13 797 623.9, 6 pages.

(Continued)

*Primary Examiner* — Ling X Xu
*Assistant Examiner* — Alan Diamond
(74) *Attorney, Agent, or Firm* — Oblon, McClelland, Maier & Neustadt, L.L.P.

(57) ABSTRACT

An organic electroluminescence device includes: a cathode; an anode; and an organic thin-film layer disposed between the cathode and the anode, the organic thin-film layer having one or more layers including an emitting layer, in which the emitting layer includes a first material represented by the following formula (1) and a second material in a form of a fluorescent dopant material.

$$(B)_b - L - (A)_a \quad (1)$$

44 Claims, 15 Drawing Sheets

(56) References Cited

FOREIGN PATENT DOCUMENTS

| | | | | |
|---|---|---|---|---|
| WO | 2003/080760 | | 10/2003 | |
| WO | WO 03/080760 | | 10/2003 | |
| WO | 2005/091684 | | 9/2005 | |
| WO | WO 2005/091684 | | 9/2005 | |
| WO | WO-2006096399 | * | 9/2006 | ..... C08G 61/12 |
| WO | 2007/065678 | | 6/2007 | |
| WO | WO 2007/065678 | | 6/2007 | |
| WO | 2010/134350 | | 11/2010 | |
| WO | 2010/134352 | | 11/2010 | |
| WO | WO 2010/134350 | | 11/2010 | |
| WO | WO 2010/134352 | | 11/2010 | |
| WO | WO 2011/024451 | A1 | 3/2011 | |
| WO | 2011/070963 | | 6/2011 | |
| WO | WO 2011/070963 | | 6/2011 | |
| WO | 2012/015017 | A1 | 2/2012 | |
| WO | 2012/133188 | | 10/2012 | |
| WO | WO 2012/133188 | | 10/2012 | |

OTHER PUBLICATIONS

Katumi Tokumaru, "Organic Photochemical Reaction Theory" Tokyo Kagaku Dojin Co., Ltd., Mar. 1973, 9 pages (w/ English lanuage translation).

Kang et al., "Prevention of H-Aggregates Formation in Cy5 Labeled Macromolecules" International Journal of Polymer Science, vol. 2010, Article ID 264781,2010, pp. 1-7.

Yokoyama et al., "Horizontal orientation of linear-shaped organic molecules having bulky substituents in neat and doped vacuum-deposited amorphous films" Organic Electronics, vol. 10, No. 1, Feb. 2009, 9 pages.

Yokoyama et al., "Horizontal molecular orientation in vacuum-deposited organic amorphous films of hole and electron transport materials" Applied Physics Letters, vol. 93. 2008, pp. 1-3.

Yokoyama et al., "Enhancement of electron transport by horizontal molecular orientation of oxadiazole planar molecules in organic amorphous films" Applied Physics Letters, vol. 95, 2009, pp. 1-3.

Taiwanese Office Action dated Dec. 21, 2015 in corr. Taiwanese Patent Application No. 102119431 (w/ English translation).

European Search Report dated Sep. 7, 2016 in corr. European Patent Application No. 13797623.9.

European Office Action dated Jun. 28, 2017 in corr. European Patent Application No. 13797623.9.

European Search Report dated Sep. 29, 2021, in European Patent Application No. 2026518.1.

N. Agarwal, et al., "Tuning of HOMO levels of carbazole derivatives: New molecules for blue OLED", Synthetic Metals, vol. 161, No. 5, pp. 466-473 (2011).

Satoh et al., "Expression of Thermally-Activated Delayed Fluorescence of High Efficiency and Application Thereof to Oled", Center for Organic Photonics and Electronics Research, Center or Future Laboratory, Kyushu University, Jun. 2010.

Nasu et al.,"Development of Highly-Efficient Fluorescent Electroluminescence device Utilizing Thermally Activated Delayed Fluorescence of Spiro-Structured Molecules", Kyusyu University, OLED; Thermally activated delayed fluorescence; Spiro configuration, Jan. 2012.

International Search Report for corr. International Application No. PCT/JP2013/065095, dated Sep. 3, 2012.

Jing Kang, et al., "Prevention of H-Aggregates Formation in Cy5 Labeled Macromolecules" International Journal of Polymer Science, vol. 2010, Article ID 264781, 2010, pp. 1-7.

M. Kasha, et al., "The Exciton Model in Molecular Spectroscopy" Pure and Applied Chemistry, vol. 11, 1965, pp. 371-392.

Suresh Das et al., "Can H-Aggregates Serve as Light-Harvesting Antennae? Triplet-Triplet Energy Transfer between Excited Aggregates and Monomer Thionine in Aerosol-OT Solutions" J. Phys. Chem. B., vol. 103, No. 1, 1999, pp. 209-215.

Daisuke Yokoyama, et al., "Horizontal orientation of linear-shaped organic molecules having bulky substituents in neat and doped vacuum-deposited amorphous films" Organic Electronics, vol. 10, No. 1, Feb. 2009, 9 pages.

Daisuke Yokoyama, et al., "Horizontal molecular orientation in vacuum-deposited organic amorphous films of hole and electron transport materials" Applied Physics Letters, vol. 93, 2008, pp. 1-3.

Daisuke Yokoyama, et al., "Enhancement of electron transport by horizontal molecular orientation of oxadiazole planar molecules in organic amorphous films" Applied Physics Letters, vol. 95, 2009, pp. 1-3.

* cited by examiner

H-1

LUMO

HOMO

H-2

LUMO

HOMO

H-3

LUMO

HOMO

ORGANIC ELECTROLUMINESCENCE DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION(S)

The *present* application is *a reissue application of U.S. Pat. No. 9,099,658, which is* based upon and claims the benefit of priority from the prior Japanese Patent Application No. 2012-126500, filed Jun. 1, 2012, and Japanese Patent Application No. 2012-221701, filed Oct. 3, 2012; the entire contents of which are incorporated herein by reference.

FIELD

Embodiments described herein relates to an organic electroluminescence device.

BACKGROUND

When voltage is applied on an organic electroluminescence device (hereinafter, referred to as an organic EL device), holes and electrons are respectively injected into an emitting layer from an anode and a cathode. The injected holes and electrons are recombined in the emitting layer to form excitons. Here, according to the electron spin statistics theory, singlet excitons and triplet excitons are generated at a ratio of 25%:75%. In the classification according to the emission principle, in a fluorescent EL device which uses emission caused by singlet excitons, an internal quantum efficiency of the organic EL device is believed to be limited to 25%. On the other hand, it has been known that the internal quantum efficiency can be improved up to 100% under efficient intersystem crossing from the singlet excitons in a phosphorescent EL device which uses emission caused by triplet excitons.

A technology for extending a lifetime of a fluorescent organic EL device has recently been improved and applied to a full-color display of a mobile phone, TV and the like. However, an efficiency of a fluorescent EL device is required to be improved.

Based on such a background, a highly efficient fluorescent organic EL device using delayed fluorescence has been proposed and developed. For instance, Literature 1 (International Publication No. WO2010/134350) and Literature 2 (International Publication No. WO2011/070963) disclose an organic EL device using TTF (Triplet-Triplet Fusion) mechanism that is one of mechanisms for delayed fluorescence. The TTF mechanism utilizes a phenomenon in which singlet excitons are generated by collision between two triplet excitons.

By using delayed fluorescence by the TTF mechanism, it is considered that an internal quantum efficiency can be theoretically raised up to 40% even in fluorescent emission. However, as compared with phosphorescent emission, the fluorescent emission is still problematic on improving efficiency. Accordingly, in order to enhance the internal quantum efficiency, an organic EL device using another delayed fluorescence mechanism has been studied.

For instance, TADF (Thermally Activated Delayed Fluorescence) mechanism is used. The TADF mechanism utilizes a phenomenon in which inverse intersystem crossing from triplet excitons to singlet excitons is generated by using a material having a small energy gap (ΔST) between the singlet level and the triplet level. An organic EL device using the TADF mechanism is disclosed in, for instance, Literature 3: "Expression of Thermally-Activated Delayed Fluorescence of High Efficiency and Application thereof to OLED" Organic EL Symposium, proceeding for the tenth meeting edited by Chihaya Adachi et al., pp. 11-12, Jun. 17-18, 2010. In the organic EL device of Literature 3, a compound having a small ΔST is used as a dopant material to cause inverse intersystem crossing from the triplet level to the singlet level by heat energy. It is considered that the internal quantum efficiency can be theoretically raised up to 100% even in fluorescent emission by using delayed fluorescence by the TADF mechanism.

An organic EL device having a doped layer using a specific host material and a specific compound having a spiro skeleton as a dopant material is disclosed in Literature 4: "Development of Highly-Efficient Fluorescent Electroluminescence device Utilizing Thermally Activated Delayed Fluorescence of Spiro-Structured Molecules" Chemical Society of Japan, proceeding for the 92nd Spring meeting on Mar. 25-28, 2012 edited by Chihaya Adachi et al., 3M3-37). The organic EL device exhibits a high external quantum efficiency with the use of the TADF mechanism.

However, although the organic EL devices disclosed in Literatures 3 and 4 exhibit the maximum luminous efficiency at 0.01 mA/cm$^2$ of a low current density area, so-called roll-off is generated to decrease a luminous efficiency in a practically high current density area from approximately 1 mA/cm$^2$ to 10 mA/cm$^2$.

Accordingly, it is considered that many practical problems in using delayed fluorescence by the TADF mechanism are left unsolved, among which improvement in the luminous efficiency in the practically high current density area has been particularly demanded.

BRIEF SUMMARY OF THE INVENTION

An organic electroluminescence device according to an exemplary embodiment includes: a cathode; an anode; and an organic thin-film layer disposed between the cathode and the anode, the organic thin-film layer having one or more layers comprising an emitting layer, the emitting layer including a first material represented by a formula (1) below and a second material in a form of a fluorescent dopant material,

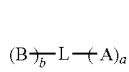

$$(B)_b - L - (A)_a \quad (1)$$

where, in the formula (1):

A is a group having a partial structure selected from formulae (a-1) to (a-7) below;

B is a group having a partial structure selected from formulae (b-1) to (b-6) below;

L represents a single bond or a linking group;

the linking group is:

a substituted or unsubstituted aryl group having 6 to 30 ring carbon atoms;

a substituted or unsubstituted heterocyclic group having 5 to 30 ring atoms; or a group derived from a group formed by mutually bonding two to five of the substituted or unsubstituted aryl group having 6 to 30 ring carbon atoms and/or the substituted or unsubstituted heterocyclic group having 5 to 30 ring atoms, the mutually bonded groups being the same or different;

a is an integer in a range from 1 to 5 representing the number of a substituent(s) of A directly bonded to L;

a plurality of A being mutually the same or different when a is 2 or more, b is an integer in a range from 1 to 5 representing the number of a substituent(s) of B directly bonded to L, a plurality of B being mutually the same or different when b is 2 or more;

(a-1)

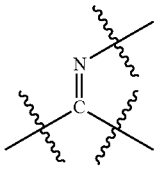

(a-2)

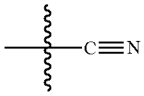

(a-3)

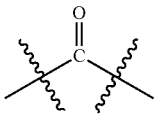

(a-4)

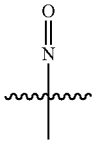

(a-5)

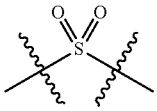

(a-6)

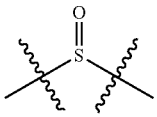

(a-7)

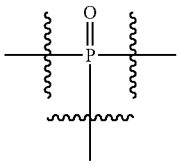

(b-1)

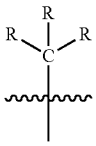

(b-2)

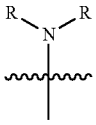

-continued (b-3)

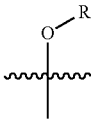

(b-4)

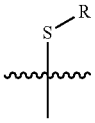

(b-5)

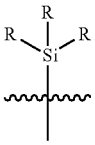

(b-6)

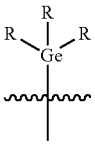

where, in the formula (b-1) to (b-6):

R is:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms, and when a plurality of R are present, the plurality of R being mutually the same or different.

In an organic electroluminescence device according to another exemplary embodiment, the second material contained in the emitting layer may be a dopant material that is not a heavy metal complex.

Specifically, the organic electroluminescence device according to the above exemplary embodiment includes: a cathode; an anode; and an organic thin-film layer disposed between the cathode and the anode, the organic thin-film layer having one or more layers including an emitting layer, in which the emitting layer includes a first material represented by the above formula (1) and a second material in a form of a dopant material, with the proviso that the dopant material is not a heavy metal complex.

The first material represented by the formula (1) in the above exemplary embodiment is the same as described above.

The organic EL device according to the exemplary embodiment(s) efficiently emits light even in a practical high-current-density area.

DETAILED DESCRIPTION OF THE INVENTION

Arrangement(s) of Organic EL Device

Figure 1:
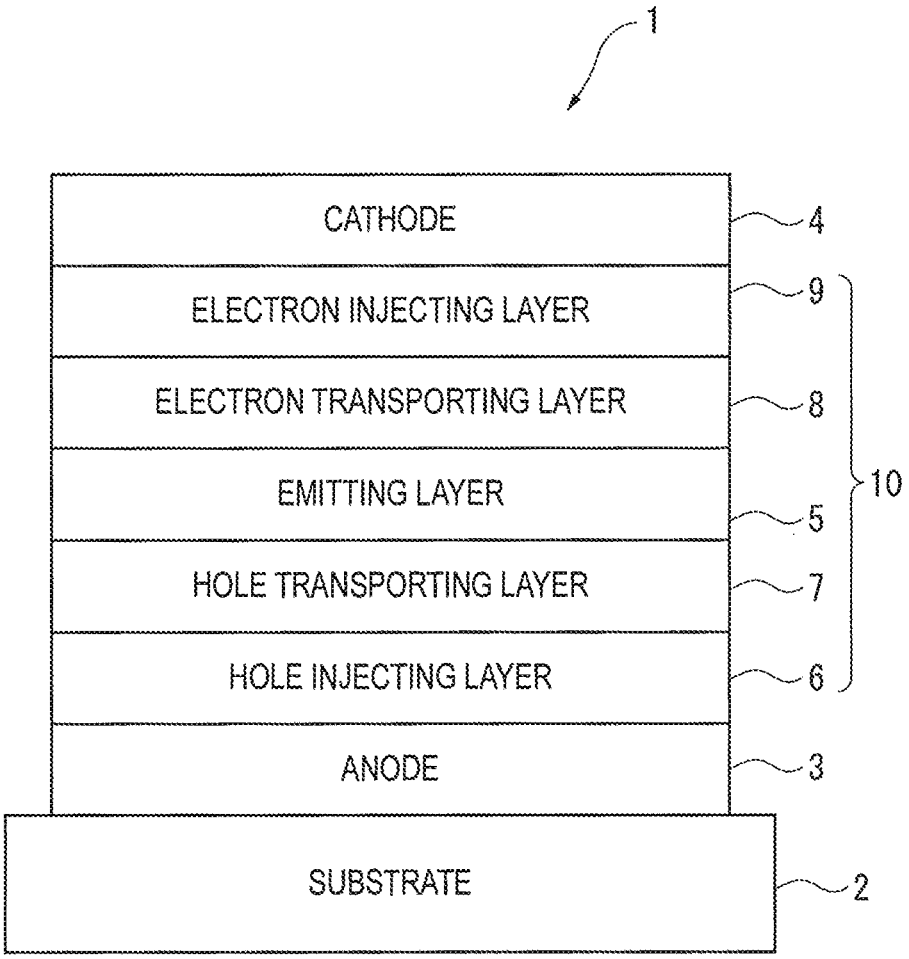
FIG. 1 schematically shows an exemplary arrangement of an organic EL device according to an exemplary embodiment of the invention.

Arrangement(s) of an organic EL device according to an exemplary embodiment will be described below.

The organic EL device according to the exemplary embodiment includes a pair of electrodes and an organic compound layer between the pair of electrodes. The organic compound layer includes at least one layer formed of an organic compound. The organic compound layer may include an inorganic compound.

In the organic EL device according to the exemplary embodiment, at least one layer of the organic compound layer includes an emitting layer. Accordingly, the organic compound layer may be provided by a single emitting layer. Alternatively, the organic compound layer may be provided by layers applied in a known organic EL device such as a hole injecting layer, a hole transporting layer, an electron injecting layer, an electron transporting layer, a hole blocking layer and an electron blocking layer.

The following are representative structure examples of an organic EL device:

(a) anode/emitting layer/cathode;

(b) anode/hole injecting•transporting layer/emitting layer/cathode;

(c) anode/emitting layer/electron injecting transporting layer/cathode;

(d) anode/hole injecting transporting layer/emitting layer/electron injecting•transporting layer/cathode; and (e) anode/hole injecting•transporting layer/emitting layer/blocking layer/electron injecting•transporting layer/cathode.

While the arrangement (d) is preferably used among the above arrangements, the arrangement of the invention is not limited to the above arrangements.

It should be noted that the aforementioned "emitting layer" is an organic compound layer generally employing a doping system and including a first material and a second material. In general, the first material promotes recombination of electrons and holes and transmits excitation energy generated by recombination to the second material. The first material is often referred to as a host material. Accordingly, the first material is referred to as the host material in descriptions hereinafter. In general, the second material receives the excitation energy from the host material (the first material) to exhibit a high luminescent performance. The second material is often referred to as a dopant material. Accordingly, the second material is referred to as the dopant material in descriptions hereinafter. The dopant material is preferably a compound having a high quantum efficiency. In the exemplary embodiment, a material showing fluorescence (fluorescent dopant material) is used as the dopant material.

The "hole injecting/transporting layer" means "at least one of a hole injecting layer and a hole transporting layer" while the "electron injecting/transporting layer" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode.

In the exemplary embodiment, the electron transporting layer means an organic layer having the highest electron mobility among organic layer(s) providing an electron transporting zone existing between the emitting layer and the cathode. When the electron transporting zone is provided by a single layer, the single layer is the electron transporting layer. Moreover, a blocking layer having an electron mobility that is not always high may be provided as shown in the arrangement (e) between the emitting layer and the electron transporting layer in order to prevent diffusion of excitation energy generated in the emitting layer. Thus, the organic layer adjacent to the emitting layer is not always an electron transporting layer.

FIG. 1 schematically shows an arrangement of an organic EL device according to the exemplary embodiment.

An organic electroluminescence device 1 includes a light-transmissive substrate 2, an anode 3, a cathode 4 and an organic compound layer 10 disposed between the anode 3 and the cathode 4.

The organic compound layer 10 includes an emitting layer 5 containing a host material and a dopant material. The organic compound layer 10 also includes a hole injecting layer 6 and a hole transporting layer 7 between the emitting layer 5 and the anode 3 in sequence from the anode 3. The organic compound layer 10 further includes an electron transporting layer 8 and an electron injecting layer 9 between the emitting layer 5 and the cathode 4 in sequence from the emitting layer 5.

Emitting Layer

Compound(s) of Emitting Layer

After conducting concentrated studies in order to solve the above problem, the inventors found that the organic EL device efficiently causes light emission even in a practical high-current-density area by using a specific compound as a first material and a fluorescent dopant material as a second material, and reached the invention.

It is speculated that the use of a specific fluorescent dopant material as the second material would result in a more advantageous effect.

Compounds to be used herein as the host material and the dopant material are as follows.

Host Material

As the host material, a first material represented by the following formula (1) is usable.

$$(B)_b-L-(A)_a \quad (1)$$

In the formula (1):

A is a group having a partial structure selected from the formulae (a-1) to (a-7) below; B is a group having a partial structure selected from the formulae (b-1) to (b-6) below; and L represents a single bond or a linking group.

The linking group is a group derived from: a substituted or unsubstituted aryl group having 6 to 30 ring carbon atoms, substituted or unsubstituted heterocyclic group having 5 to 30 ring atoms, or a group formed by bonding two to five of the above groups;

The mutually bonded groups are the same or different.

a is an integer in a range from 1 to 5 representing the number of a substituent(s) of A directly bonded to L, a plurality of A being mutually the same or different when a is 2 or more; and b is an integer in a range from 1 to 5 representing the number of a substituent(s) of B directly bonded to L, a plurality of B being mutually the same or different when b is 2 or more.

(a-1)

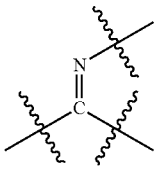

(a-2)

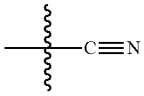

(a-3)

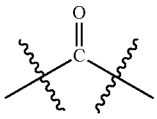

(a-4)

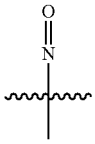

(a-5)

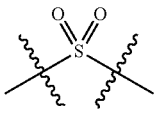

-continued (a-6)

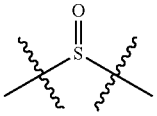

(a-7)

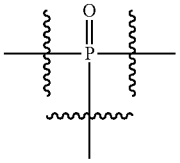

(b-1)

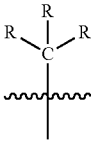

(b-2)

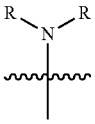

(b-3)

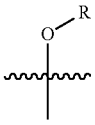

(b-4)

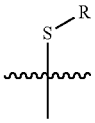

(b-5)

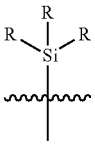

(b-6)

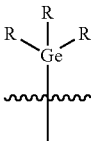

In the formula (b-1) to (b-6), R is selected from a hydrogen atom, substituted or unsubstituted aryl group having 6 to 30 ring carbon atoms, substituted or unsubstituted heterocyclic group having 5 to 30 ring atoms or substituted or unsubstituted alkyl group having 1 to 30 carbon atoms. When a plurality of R are present, the plurality of R are mutually the same or different.

In the above formula (1), B is a component having a donor element and A is a component having an acceptor component. In other words, the partial structure of B selected from the above formulae (b-1) to (b-6) is the structure having the donor element, and the partial structure of A selected from the above formulae (a-1) to (a-7) is the structure having the acceptor element. It should be noted that the donor element refers to electron-donating property while the acceptor element refers to electron-accepting property.

Preferably, the formula (1) is represented by one of the following formulae (1a) to (1g).

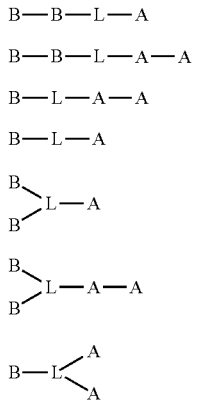

(1a)

(1b)

(1c)

(1d)

(1e)

(1f)

(1g)

The aryl group having 6 to 30 ring carbon atoms in the formulae (1) and (b-1) to (b-6) includes a fused aryl group, examples of which are a phenyl group, 1-naphthyl group, 2-naphthyl group, 1-anthryl group, 2-anthryl group, 9-anthryl group, benzanthryl group, 1-phenanthryl group, 2-phenanthryl group, 3-phenanthryl group, 4-phenanthryl group, 9-phenanthryl group, naphthacenyl group, pyrenyl group, 1-chrysenyl group, 2-chrysenyl group, 3-chrysenyl group, 4-chrysenyl group, 5-chrysenyl group, 6-chrysenyl group, benzo[c]phenanthryl group, benzo[g]chrysenyl group, 1-triphenylenyl group, 2-triphenylenyl group, 3-triphenylenyl group, 4-triphenylenyl group, 1-fluorenyl group, 2-fluorenyl group, 3-fluorenyl group, 4-fluorenyl group, 9-fluorenyl group, benzofluorenyl group, dibenzofluorenyl group, 2-biphenylyl group, 3-biphenylyl group, 4-biphenylyl group, o-terphenyl group, m-terphenyl-4-yl group, m-terphenyl-3-yl group, m-terphenyl-2-yl group, p-terphenyl-4-yl group, p-terphenyl-3-yl group, p-terphenyl-2-yl group, m-quarterphenyl group, 3-fluoranthenyl group, 4-fluoranthenyl group, 8-fluoranthenyl group, 9-fluoranthenyl group, benzofluoranthenyl group, o-tolyl group, m-tolyl group, p-tolyl group, 2,3-xylyl group, 3,4-xylyl group, 2,5-xylyl group, mesityl group, o-cumenyl group, m-cumenyl group, p-cumenyl group, p-t-butylphenyl group, p-(2-phenylpropyl)phenyl group, 4'-methylbiphenylyl group and 4"-t-butyl-p-terphenyl-4-yl group.

The aryl group preferably has 6 to 20 ring carbon atoms, more preferably 6 to 12 ring carbon atoms. Among the aryl group, a phenyl group, biphenyl group, naphthyl group, phenanthryl group and terphenyl group are particularly preferable.

The heterocyclic group having 5 to 30 ring carbon atoms includes a fused heterocyclic group, examples of which are a pyroryl group, pyrazinyl group, pyridinyl group, indolyl group, isoindolyl group, imidazolyl group, furyl group, benzofuranyl group, isobenzofuranyl group, dibenzofuranyl group, dibenzothiophenyl group, quinolyl group, isoquinolyl group, quinoxalinyl group, carbazolyl group, phenantridinyl group, acridinyl group, phenanthrolinyl group, phenazinyl group, phenothiazinyl group, phenoxazinyl group, oxazolyl group, oxadiazoyl group, furazanyl group, thienyl group, benzothiophenyl group and a group formed from a pyridine ring, pyrazine ring, pyrimidine ring, pyridazine ring, triazine ring, indole ring, quinoline ring, acridine ring, pirrolidine ring, dioxane ring, piperidine ring, morpholine ring, piperadine ring, carbazole ring, furan ring, thiophene ring, oxazole ring, oxadiazole ring, benzoxazole ring, thiazole ring, thiadiazole ring, benzothiazole ring, triazole ring, imidazole ring, benzimidazole ring, pyrane ring and dibenzofuran ring.

Specific examples of the heterocyclic group having 5 to 30 ring atoms are a 1-pyroryl group, 2-pyroryl group, 3-pyroryl group, pyrazinyl group, 2-pyridinyl group, 2-pyrimidinyl group, 4-pyrimidinyl group, 5-pyrimidinyl group, 6-pyrimidinyl group, 1,2,3-triazine-4-yl group, 1,2,4-triazine-3-yl group, 1,3,5-triazine-2-yl group, 1-imidazolyl group, 2-imidazolyl group, 1-pyrazolyl group, 1-indolidinyl group, 2-indolidinyl group, 3-indolidinyl group, 5-indolidinyl group, 6-indolidinyl group, 7-indolidinyl group, 8-indolidinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, azacarbazolyl-1-yl group, azacarbazolyl-2-yl group, azacarbazolyl-3-yl group, azacarbazolyl-4-yl group, azacarbazolyl-5-yl group, azacarbazolyl-6-yl group, azacarbazolyl-7-yl group, azacarbazolyl-8-yl group, azacarbazolyl-9-yl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline- 7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group and 4-germafluorenyl group.

The heterocyclic group preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are preferable. In 1-carbazolyl group, 2-carbazolyl group, 3-carbazolyl group and 4-carbazolyl group, a nitrogen atom at the ninth position is preferably substituted by a substituted or unsubstituted aryl group having 6 to 30 ring carbon atoms or a substituted or unsubstituted heterocyclic group having 5 to 30 ring atoms.

The alkyl group having 1 to 30 carbon atoms in the formulae (b-1) to (b-6) may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group, and 1,2,3-trinitropropyl group.

Examples of the cyclic alkyl group (cycloalkyl group) are a cyclopropyl group, cyclobutyl group, cyclopentyl group, cyclohexyl group, 4-methylcyclohexyl group, 3,5-tetramethylcyclohexyl group, cycloheptyl group, cyclooctyl group, 1-adamantyl group, 2-adamantyl group, 1-norbornyl group and 2-norbornyl group.

The linear or branched alkyl group preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group and n-hexyl group are preferable.

The cycloalkyl group preferably has 3 to 10 ring carbon atoms, more preferably 5 to 8 ring carbon atoms. Among the cycloalkyl group, a cyclopentyl group and a cyclohexyl group are preferable.

A halogenated alkyl group provided by substituting the alkyl group with a halogen atom is exemplified by a halogenated alkyl group provided by substituting the alkyl group having 1 to 30 carbon atoms with one or more halogen groups. Specific examples of the halogenated alkyl group are a fluoromethyl group, difluoromethyl group, trifluoromethyl group, fluoroethyl group and trifluoromethylmethyl group.

In the formula (1), L is preferably single bond or a divalent group derived from any one of a phenyl group, biphenyl group, terphenyl group and triphenylenyl group. With the use of the above L, the electron orbits of LUMO and HOMO of a compound can be localized so as not to be overlapped with each other.

Further, in the compound represented by the above formula (1), in order to localize (i.e. not to overlap) the electron orbits of LUMO and HOMO, the A and B in the above formula (1) preferably have no fused aromatic hydrocarbon as a partial structure thereof.

When R is a group derived from a substituted or unsubstituted aryl group having 6 to 30 ring carbon atoms in the formula (b-1) to (b-6), R is preferably a phenyl group, a biphenyl group, a terphenyl group or a triphenylenyl group.

In the organic EL device according to the above exemplary embodiment, B in the above formula (1) is preferably represented by any one of formulae (2), (3), (4), (5) and (6) below.

(2)

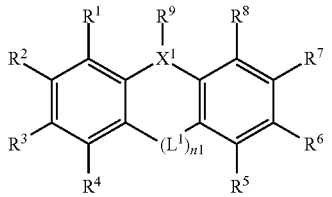

In the formula (2), $R^1$ to $R^9$ each independently represent:

a hydrogen atom;

a substituted or unsubstituted aryl group having 6 to 30 ring carbon atoms;

a substituted or unsubstituted heterocyclic group having 5 to 30 ring atoms;

a substituted or unsubstituted alkyl group having 1 to 30 carbon atoms;

a substituted or unsubstituted alkylsilyl group having 3 to 30 carbon atoms;

a substituted or unsubstituted arylsilyl group having 6 to 60 ring carbon atoms;

a substituted or unsubstituted alkoxy group having 1 to 30 carbon atoms;

a substituted or unsubstituted aryloxy group having 6 to 30 ring carbon atoms;

a substituted or unsubstituted alkylamino group having 2 to 30 carbon atoms;

a substituted or unsubstituted arylamino group having 6 to 60 ring carbon atoms;

a substituted or unsubstituted alkylthio group having 1 to 30 carbon atoms; or a substituted or unsubstituted arylthio group having 6 to 30 ring carbon atoms.

In the above, at least one of the combinations of $R^1$ and $R^2$, $R^2$ and $R^3$, $R^3$ and $R^4$, $R^5$ and $R^6$, $R^6$ and $R^7$, $R^7$ and $R^8$, $R^8$ and $R^9$ and $R^9$ and $R^1$ may form a saturated or unsaturated cyclic structure.

$L^1$ is a linking group selected from the formulae (21) to (27) below.

n1 represents an integer in a range from 1 to 3. A plurality of $L^1$ are mutually the same or different when n1 is 2 or 3.

$X^1$ is a linking group selected from the formulae (41) to (45) below.

(21)

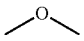

(22)

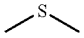

(23)

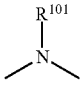

(24)

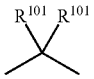

(25)

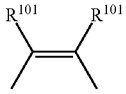

(26)

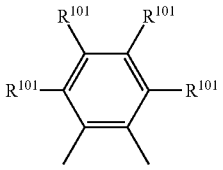

(27)

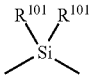

In the formulae (23) to (27), $R^{101}$ are the same as $R^1$ to $R^9$ in the formula (2).

In the formula (2), one of $R^1$ to $R^9$ or $R^{101}$ is a single bond to be bonded to L.

When a plurality of $R^{101}$ are present, the plurality of $R^{101}$ are mutually the same or different.

(41)

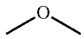

(42)

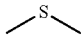

(43)

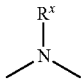

(44)

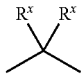

(45)

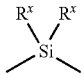

In the above formulae (43) to (45), $R^x$ represents:

a hydrogen atom;

a substituted or unsubstituted aryl group having 6 to 30 ring carbon atoms;

a substituted or unsubstituted heterocyclic group having 5 to 30 ring atoms, or a substituted or unsubstituted alkyl group having 1 to 30 carbon atoms.

When a plurality of $R^x$ are present, the plurality of $R^x$ are mutually the same or different.

The compound represented by the formula (2) may alternatively be represented by any one of the following formulae (2a) to (2c):

(2a)

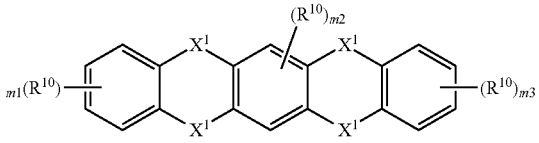

In the above formula (2a), $R^{10}$ is the same as $R^1$ to $R^9$ in the formula (2).

m1 and m3 represent an integer in a range from 0 to 4. m2 represents an integer in a range from 0 to 2.

Plural $R^{10}$ may be mutually the same or different.

$X^1$ is a linking group selected from the above formulae (41) to (45).

Plural $X^1$ may be mutually the same or different.

In the formula (2a), one of $R^{10}$ and $R^x$ in the above formulae (43) to (45) is a single bond to be bonded to L.

(2b)

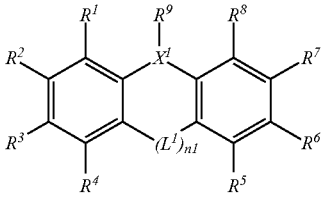

-continued (2b)

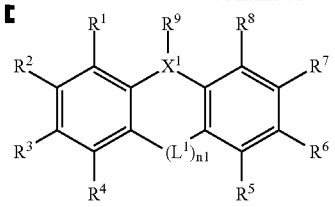

In the formula (2b), $R^1$ to $R^9$, $L^1$ and n1 are the same as $R^1$ to $R^9$, $L^1$ and n1 in the above formula (2).

(2c)

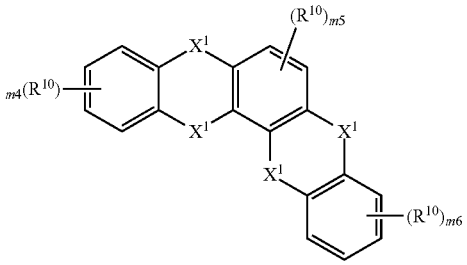

In the above formula (2c), $R^{10}$ is the same as $R^1$ to $R^9$ in the formula (2).

m4 and m6 represent an integer in a range from 0 to 4. m5 represents an integer in a range from 0 to 2.

Plural $R^{10}$ may be mutually the same or different.

$X^1$ is a linking group selected from the above formulae (41) to (45).

Plural $X^1$ may be mutually the same or different.

(3)

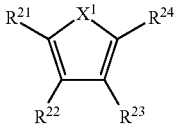

In the above formula (3), $R^{21}$ to $R^{24}$ represent the same as $R^1$ to $R^9$ in the formula (2).

One of the combinations of $R^{21}$ and $R^{22}$, $R^{22}$ and $R^{23}$, and $R^{23}$ and $R^{24}$ may form a saturated or unsaturated cyclic structure.

$X^1$ is a linking group selected from the above formulae (41) to (45).

In the above formula (3), one of $R^{21}$ to $R^{24}$ and $R^x$ is a single bond to be bonded to L.)

(4)

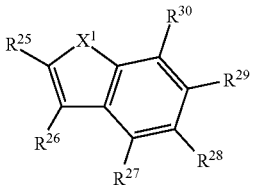

In the above formula (4), $R^{25}$ to $R^{30}$ represent the same as $R^1$ to $R^9$ in the formula (2).

One of the combinations of $R^{25}$ and $R^{26}$, $R^{27}$ and $R^{28}$, $R^{28}$ and $R^{29}$, and $R^{29}$ and $R^{30}$ may form a saturated or unsaturated cyclic structure.

$X^1$ is a linking group selected from the above formulae (41) to (45).

In the above formula (4), one of $R^{25}$ to $R^{30}$ and $R^x$ is a single bond to be bonded to L.

(5)

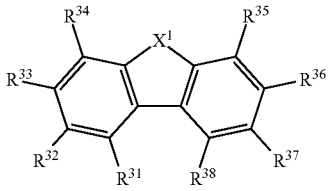

In the above formula (5), $R^{31}$ to $R^{38}$ represent the same as $R^1$ to $R^9$ in the formula (2).

One of the combinations of $R^{31}$ and $R^{32}$, $R^{32}$ and $R^{33}$, $R^{33}$ and $R^{34}$, and $R^{35}$ and $R^{36}$, $R^{36}$ and $R^{37}$, and $R^{37}$ and $R^{38}$ may form a saturated or unsaturated cyclic structure.

$X^1$ is a linking group selected from the above formulae (41) to (45).

In the above formula (5), one of $R^{31}$ to $R^{38}$ and $R^x$ is a single bond to be bonded to L.

At least one of $R^{31}$ to $R^{38}$ in the above formula (5) is preferably represented by a formula (51) below.

(51)

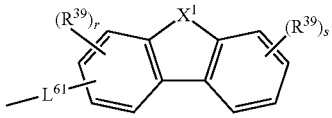

In the above formula (51), $R^{39}$ represents the same as $R^1$ to $R^9$ in the formula (2).

r represents an integer in a range from 0 to 3; and S represents an integer in a range from 0 to 4.

Plural $R^{39}$ may be mutually the same or different.

$X^1$ is a linking group selected from the above formulae (41) to (45).

$L^{61}$ represents a single bond or a linking group;

Examples of the linking group are as follows:

a substituted or unsubstituted aryl group having 6 to 30 ring carbon atoms;

a substituted or unsubstituted heterocyclic group having 5 to 30 ring atoms, or a group derived from a group formed by mutually bonding two to five of the substituted or unsubstituted aryl group having 6 to 30 ring carbon atoms and/or the substituted or unsubstituted heterocyclic group having 5 to 30 ring atoms. The mutually bonded groups are the same or different.

$$(Z^b)_r—Ar^b— \quad (6)$$

$$(Z^b)_r—Ar^b— \quad (6)$$

In the above formula (6), $Ar^b$ represents a single bond, or a substituted or unsubstituted aryl group having 6 to 30 ring carbon atoms.

[Zb] $Z^b$ represents:

a substituted or unsubstituted tertiary alkyl group having 4 to 30 carbon atoms;

a substituted or unsubstituted alkylsilyl group having 3 to 30 carbon atoms;

a substituted or unsubstituted arylsilyl group having 6 to 60 ring carbon atoms;

a substituted or unsubstituted alkoxy group having 1 to 30 carbon atoms;

a substituted or unsubstituted aryloxy group having 6 to 30 ring carbon atoms;

a substituted or unsubstituted alkylamino group having 2 to 60 carbon atoms;

a substituted or unsubstituted [acylamino] *arylamino* group having 6 to 60 ring carbon atoms;

a substituted or unsubstituted alkylthio group having 1 to 30 carbon atoms; or a substituted or unsubstituted arylthio group having 6 to 30 ring carbon atoms.

r is an integer in a range from 1 to 5 representing the number of a substituent(s) of $Z^b$ directly bonded to [$A^b$] $Ar^b$, a plurality of $Z^b$ being mutually the same or different when r is 2 or more.

The aryl group having 6 to 30 ring carbon atoms and heterocyclic group having 5 to 30 ring carbon atoms in the formulae (2) to (6) and (51) may be the group explained with reference to the above formulae (1) and (b-1) to (b-6).

The alkyl group having 1 to 30 carbon atoms in the formulae (2) to (5) and (51) may be the group explained with reference to the above formulae (1) and (b-1) to (b-6).

The tertiary alkyl group having 4 to 30 carbon atoms in the formula (6) may be the tertiary alkyl group in the groups explained with reference to the above formulae (1) and (b-1) to (b-6).

The alkylsilyl group having 3 to 60 carbon atoms in the formulae (2) to (6) is exemplified by a trialkylsilyl group having the examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyldimethylsilyl group, propyldimethylsilyl group and triisopropylsilyl group. Three alkyl groups may be the same or different.

Examples of the arylsilyl group having 6 to 60 ring carbon atoms are a dialkylarylsilyl group, alkyldiarylsilyl group and triarylsilyl group.

The dialkylarylsilyl group is exemplified by a dialkylarylsilyl group having two of the examples of the alkyl group having 1 to 30 carbon atoms and one of the aryl group having 6 to 30 ring carbon atoms. The dialkylarylsilyl group preferably has 8 to 30 carbon atoms. Two alkyl groups may be the same or different.

The alkyldiarylsilyl group is exemplified by an alkyldiarylsilyl group having one of the examples of the alkyl group having 1 to 30 carbon atoms and two of the aryl group having 6 to 30 ring carbon atoms. The dialkylarylsilyl group preferably has 13 to 30 carbon atoms. Two aryl groups may be the same or different.

The triarylsilyl group is exemplified by a triarylsilyl group having three of the aryl group having 6 to 30 ring carbon atoms. The triarylsilyl group preferably has 18 to 30 carbon atoms. Three aryl groups may be the same or different.

Examples of the above arylsilyl group are a phenyldimethylsilyl group, a diphenylmethylsilyl group, a diphenyl-t-butylsilyl group and a triphenylsilyl group.

The alkoxy group having 1 to 30 carbon atoms is represented by —$OR_V$. $R_V$ is exemplified by the above alkyl group having 1 to 30 carbon atoms. As the above alkoxy group, an alkoxy group having 1 to 6 carbon atoms is preferable and specific examples thereof are a methoxy group, ethoxy group, propoxy group, butoxy group, pentyloxy group, and hexyloxy group.

A halogenated alkoxy group provided by substituting the alkoxy group with a halogen atom is exemplified by a halogenated alkoxy group provided by substituting the alkoxy group having 1 to 30 carbon atoms with one or more halogen groups.

The aryloxy group having 6 to 30 ring carbon atoms is represented by —$OR_W$. $R_W$ is exemplified by the above aryl group having 6 to 30 ring carbon atoms. The aryloxy group is exemplified by a phenoxy group.

The alkylamino group having 2 to 60 carbon atoms is represented by —$NHR_V$ or —$N(R_V)_2$. $R_V$ is exemplified by the alkyl group having 1 to 30 carbon atoms.

The arylamino group having 6 to 60 ring carbon atoms is represented by [—$NH_2R_W$ or —$NH(R_W)_2$] —$NHR_W$ *or* —$N(R_W)_2$. $R_W$ is exemplified by the above aryl group having 6 to 30 ring carbon atoms.

The alkylthio group having 1 to 30 carbon atoms is represented by —$SR_V$. $R_V$ is exemplified by the alkyl group having 1 to 30 carbon atoms.

The arylthio group having 6 to 30 ring carbon atoms is represented by —$SR_W$. $R_W$ is exemplified by the above aryl group having 6 to 30 ring carbon atoms.

In the above formulae (2) to (6) and (51), when $R^1$ to $R^9$, $R^{11}$ to $R^{19}$, $R^{21}$ to $R^{24}$, $R^{101}$, $R^{201}$, $R^x$, $R^{25}$ to $R^{30}$ and $R^{31}$ to $R^{38}$ are a substituted or unsubstituted aryl group having 6 to 30 ring carbon atoms, $Ar^b$ and $R_W$ are preferably a phenyl group, a biphenyl group, a terphenyl group or a triphenylenyl group in order to localize (i.e. not to overlap) the electron orbits of LUMO and HOMO of the compound represented by the above formula (1).

B in the above formula (1) may be represented by a formula (3a) below.

(3a)

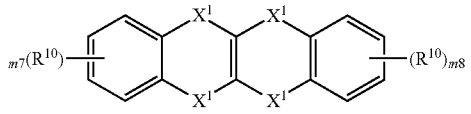

In the above formula (3a), $R^{10}$ is the same as $R^1$ to $R^9$ in the formula (2).

m7 and m8 represent an integer in a range from 0 to 4.

Plural $R^{10}$ may be mutually the same or different.

$X^1$ is a linking group selected from the above formulae (41) to (45).

Plural $X^1$ may be mutually the same or different.

In the organic EL device according to the above exemplary embodiment, A in the above formula (1) is preferably represented by one of formulae (8), (9), (10), (11), (12), (13) and (14) below.

(8)

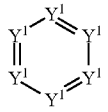

In the formula (8), two to four of $Y^1$ are a nitrogen atom, one of $Y^1$ is a carbon atom bonded to L and the rest of $Y^1$ is $CR^y$.

When the formula (8) includes a plurality of $R^y$, the plurality of $R^y$ independently represent: a hydrogen atom; a fluorine atom; a cyano group; a nitro group; a substituted or unsubstituted aryl group having 6 to 30 ring carbon atoms; a substituted or unsubstituted heterocyclic group having 5 to 30 ring atoms; a substituted or unsubstituted alkyl group having 1 to 30 carbon atoms; a substituted or unsubstituted alkylcarbonyl group having 1 to 30 carbon atoms; a substituted or unsubstituted arylcarbonyl group having 6 to 30 carbon atoms; a substituted or unsubstituted alkylsulfinyl group having 1 to 30 carbon atoms; a substituted or unsubstituted arylsulfinyl group having 6 to 30 ring carbon atoms; a substituted or unsubstituted alkylphosphinyl group having 2 to 60 carbon atoms; a substituted or unsubstituted arylphosphinyl group having 6 to 60 ring carbon atoms; a substituted or unsubstituted alkylsulphonyl group having 1 to 30 carbon atoms; a substituted or unsubstituted arylsulphonyl group having 6 to 30 ring carbon atoms; a substituted or unsubstituted alkylsilyl group having 3 to 60 carbon atoms; a substituted or unsubstituted arylsilyl group having 8 to 60 ring carbon atoms; a substituted or unsubstituted alkoxy group having 1 to 30 carbon atoms; or a substituted or unsubstituted aryloxy group having 6 to 30 ring carbon atoms.

Adjacent two $Y^1$ may form a saturated or unsaturated cyclic structure when the adjacent two $Y^1$ are $CR^y$.

(9)

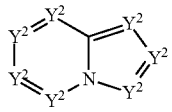

In the above formula (9), $Y^2$ is the same as the other $Y^1$ in the formula (8).

(10)

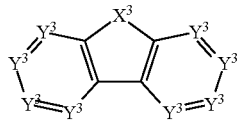

(11)

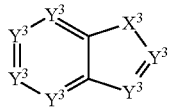

(12)

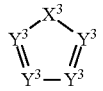

In the above formulae (10), (11) and (12), $Y^3$ represents the same as the other $Y^1$ in the formula (8).

$X^3$ is a linking group selected from the formulae (41) to (45) below.

(41)

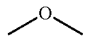

(42)

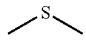

(43)

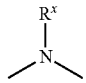

(44)

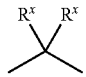

(45)

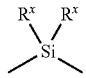

In the above formulae (43) to (45), $R^x$ independently represents: a hydrogen atom, a substituted or unsubstituted aryl group having 6 to 30 carbon atoms, a substituted or unsubstituted heterocyclic group having 5 to 30 ring atoms and a substituted or unsubstituted alkyl group having 1 to 30 carbon atoms.

When a plurality of $R^x$ are present, the plurality of $R^x$ are mutually the same or different.

(13)

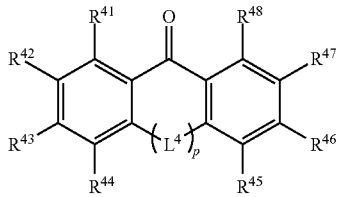

In the above formula (13), one of $R^{41}$ to $R^{48}$ is a single bond to be bonded to L.

The rest of $R^{41}$ to $R^{48}$ represent the same as $R^y$ in the above formula (8).

$L^4$ is a linking group selected from the formulae (131) to (136) below.

p represents an integer in a range from 1 to 3. The plurality of $L^4$ are mutually the same or different when p is 2 or 3.

(131)

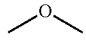

(132)

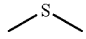

(133)

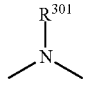

(134)

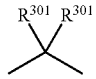

-continued (135)

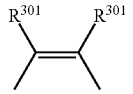

(136)

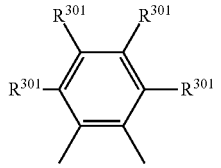

In the above formulae (133) to (136), $R^{301}$ independently represents: a hydrogen atom, a substituted or unsubstituted aryl group having 6 to 30 ring carbon atoms, a substituted or unsubstituted heterocyclic group having to 30 ring atoms and a substituted or unsubstituted alkyl group having 1 to 30 carbon atoms.

When a plurality of $R^{301}$ are present, the plurality of $R^{301}$ are mutually the same or different.

(14)

$$—Ar^a—(Z^a)_q$$

In the above formula (14), $Ar^a$ represents: a substituted or unsubstituted aryl group having 6 to 30 ring carbon atoms, or a substituted or unsubstituted heterocyclic group having 5 to 30 ring atoms.

$Zr^a$ represents one of: a fluorine atom; a cyano group; a nitro group; a substituted or unsubstituted alkylcarbonyl group having 1 to 20 carbon atoms; a substituted or unsubstituted arylcarbonyl group having 6 to 30 ring carbon atoms; a substituted or unsubstituted alkylsulfinyl group having 1 to 20 carbon atoms; a substituted or unsubstituted arylsulfinyl group having 6 to 30 ring carbon atoms; a substituted or unsubstituted alkylphosphinyl group having 2 to 60 carbon atoms; a substituted or unsubstituted arylphosphinyl group having 6 to 60 ring carbon atoms; a substituted or unsubstituted alkylsulphonyl group having 1 to 30 carbon atoms; and a substituted or unsubstituted arylsulphonyl group having 6 to 30 ring carbon atoms.

q is an integer in a range from 1 to 5 representing the number of a substituent(s) of $Z^a$ directly bonded to $Ar^a$, a plurality of $Z^a$ being mutually the same or different when q is 2 or more.

The aryl group having 6 to 30 ring carbon atoms, the heterocyclic group having 5 to 30 ring atoms, the alkyl group having 1 to 30 carbon atoms, the alkylsilyl group having 3 to 60 carbon atoms, the arylsilyl group having 8 to 30 ring carbon atoms, the alkoxy group having 1 to 30 carbon atoms and the aryloxy group having 6 to 30 ring carbon atoms in the formulae (8) to (14) may be the groups explained with reference to the above formulae (1), (b-1) to (b-2) and (2) to (6).

The alkylcarbonyl group having 1 to 30 carbon atoms is represented by $—COOR_V$.

The arylcarbonyl group having 6 to 30 ring carbon atoms is represented by $—COOR_W$.

The alkylsulphinyl group having 1 to 30 carbon atoms is represented by $—S(=O)R_V$.

The arylsulphinyl group having 6 to 30 ring carbon atoms is represented by $—S(=O)R_W$.

The alkylphosphinyl group having 2 to 40 carbon atoms is represented by $—P(=O)HR_V$ or $—P(=O)(R_V)_2$.

The arylphosphinyl group having 6 to 30 ring carbon atoms is represented by $—P(=O)HR_W$ or $—P(=O)(R_W)_2$.

The alkylsulphonyl group having 1 to 30 carbon atoms is represented by $—S(=O)_2R_V$.

The arylsulphonyl group having 6 to 30 ring carbon atoms is represented by $—S(=O)_2R_W$.

In the above groups, $R_V$ is exemplified by the alkyl group having 1 to 30 carbon atoms. $R_W$ is exemplified by the above aryl group having 6 to 30 ring carbon atoms. The aryl group having 6 to 30 ring carbon atoms are preferably a phenyl group, a biphenyl group, a terphenyl group and a triphenylenyl group.

As the first material represented by the above formula (1), since the first material is a compound in which a donor element is bonded to an acceptor element in a molecule, the first material is preferably a biscarbazole derivative represented by the following formula (101).

(101)

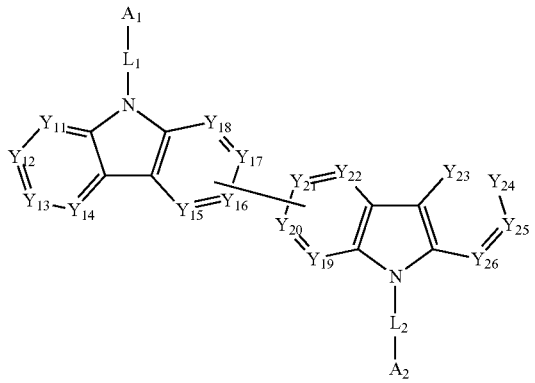

In the above formula (101), $A_1$ and $A_2$ each independently represent:

a hydrogen atom;

a halogen atom;

a cyano group, a substituted or unsubstituted aryl group having 6 to 30 ring carbon atoms;

a substituted or unsubstituted heterocyclic group having 5 to 30 ring atoms;

a substituted or unsubstituted alkyl group having 1 to 30 carbon atoms;

a substituted or unsubstituted alkoxy group having 1 to 30 carbon atoms;

a substituted or unsubstituted aralkyl group having 7 to 30 carbon atoms;

a substituted or unsubstituted aryloxy group having 6 to 30 ring carbon atoms;

a substituted or unsubstituted alkylsilyl group having 3 to 60 carbon atoms; or a substituted or unsubstituted arylsilyl group having 8 to 30 ring carbon atoms.

However, it is preferable that at least one of $A_1$ and $A_2$ is a cyano group.

In the above formula (101), $Y_{11}$ to $Y_{14}$ and $Y_{23}$ to $Y_{26}$ independently represent C(R) or a nitrogen atom. $Y_{15}$ to $Y_{18}$ independently represent C(R), a nitrogen atom or a carbon atom to be bonded to one of $Y_{19}$ to $Y_{22}$. $Y_{19}$ to $Y_{22}$ independently represent C(R), a nitrogen atom or a carbon atom to be bonded to one of $Y_{15}$ to $Y_{18}$. R independently represent a hydrogen atom or a substituent. When R is a substituent, the substituent of R is the same as the substituent of the above $A_1$ and $A_2$ when $A_1$ and $A_2$ are substituted.

$L_1$ and $L_2$ in the above formula (101) each independently represent a single bond, a substituted or unsubstituted divalent aromatic hydrocarbon group having 6 to 30 ring carbon atoms, a substituted or unsubstituted divalent heterocyclic group having 5 to 30 ring atoms, or a group formed by bonding the above divalent aromatic hydrocarbon group and the above divalent heterocyclic group.

At least one of $L_1$ and $L_2$ is preferably represented by a formula (a) below.

(a)

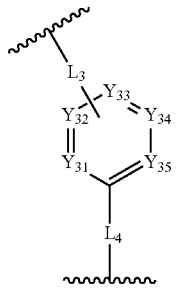

In the above formula (a), $Y_{31}$ to $Y_{35}$ each independently represent $C(R_a)$, a nitrogen atom or a carbon atom to be bonded to $L_3$, $R_a$ each representing a hydrogen atom or a substituent. When R is a substituent, the substituent of $R_a$ is the same as the substituent of the above $A_1$ and $A_2$ when $A_1$ and $A_2$ are substituted.

In the above formula (a), $L_3$ and $L_4$ each independently represent:

a single bond;

a substituted or unsubstituted divalent aromatic hydrocarbon group having 6 to 30 ring carbon atoms;

a substituted or unsubstituted divalent heterocyclic group having 5 to 30 ring atoms; or a group formed by bonding the above divalent aromatic hydrocarbon group and the divalent heterocyclic group.

In the above formula (101), the aryl group having 6 to 30 ring carbon atoms, the heterocyclic group having 5 to 30 ring atoms, the alkyl group having 1 to 30 carbon atoms, the alkoxy group having 1 to 30 carbon atoms, the aryloxy group having 6 to 30 ring carbon atoms, the alkylsilyl group having 3 to 60 carbon atoms and the arylsilyl group having 8 to 30 ring carbon atoms may be the groups explained with reference to the above formulae (1), (b-1) to (b-2) and (2) to (6).

The aralkyl group having 7 to 30 carbon atoms in the formula (101) may be the aralkyl group having 7 to 30 carbon atoms to be explained in a formula (20) below.

The divalent aromatic hydrocarbon group in the formula (a) may be a divalent group derived from an aryl group in the formulae (1) and (b-1) to (b-6). The divalent heterocyclic group having 5 to 30 ring atoms in the formula (a) may be a divalent group derived from a heterocyclic group in the formulae (1) and (b-1) to (b-6).

The compound represented by the formula (1) is especially preferably a compound in which A is represented by the above formula (14), B is represented by the above formula (2) and L is a substituted or unsubstituted aryl group having 6 to 30 ring carbon atoms. Further, L is preferably a phenylene group.

In the invention, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

Examples of the substituent meant by "substituted or unsubstituted" are the above-described aryl group, heterocyclic group, alkyl group (linear or branched alkyl group, cycloalkyl group and halogenated alkyl group), alkenyl group, alkynyl group, alkylsilyl group, arylsilyl group, alkoxy group, halogenated alkoxy group, aralkyl group, aryloxy group, halogen atom, cyano group, hydroxyl group, nitro group and carboxy group. In the above-described substituents, the aryl group, heterocyclic group, alkyl group, halogen atom, alkylsilyl group, arylsilyl group and cyano group are preferable. The preferable ones of the specific examples of each substituent are further preferable. "Unsubstituted" in "substituted or unsubstituted" means that a group is not substituted by the above-described substituents but bonded with a hydrogen atom.

In a later-described compound or a partial structure thereof, the same applies to a substituent when being "substituted or unsubstituted."

In the invention, a "hydrogen atom" means isotopes having different neutron numbers and specifically encompasses protium, deuterium and tritium.

Dopant Material

In this exemplary embodiment, the fluorescent dopant material is used as the dopant material of the emitting layer as described above.

Known fluorescent materials are usable as the fluorescent dopant material. Examples of the fluorescent dopant material include a bisarylamino naphthalene derivative, an aryl-substituted naphthalene derivative, a bisarylamino anthracene derivative, an aryl-substituted anthracene derivative, a bisarylamino pyrene derivative, an aryl-substituted pyrene derivative, a bisarylamino chrysene derivative, an aryl-substituted chrysene derivative, a bisarylamino fluoranthene derivative, an aryl-substituted fluoranthene derivative, an indenoperylene derivative, a pyrromethene boron complex compound, a compound having a pyrromethene skeleton or a metal complex thereof, a diketopyrrolopyrrole derivative, and a perylene derivative.

In the above dopant material, a dopant material represented by a formula (20) below is especially preferable.

(20)

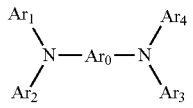

In the above formula (20):

$Ar_0$ is a substituted or unsubstituted divalent fused aromatic hydrocarbon group having 10 to 50 ring carbon atoms; and $Ar_1$ to $Ar_4$ each independently represent:

a substituted or unsubstituted aryl group having 6 to 30 ring carbon atoms;

a substituted or unsubstituted heterocyclic group having 5 to 30 ring atoms;

a substituted or unsubstituted alkyl group having 6 to 30 carbon atoms; or a substituted or unsubstituted aralkyl group having 7 to 50 carbon atoms.

Examples of the divalent fused aromatic hydrocarbon group having 10 to 50 ring carbon atoms in the above formula (20) are naphtylene group, anthracenylene group, phenanthrylene group, chrysenylene group, pyrenylene group, benzanthracenylene group, fluoranthenylene group, benzofluoranthenylene group, perylenylene group, coronenylene group, picenylene group, diphenylanthracenylene group, fluorenylene group, triphenylylene group, rubicenylene group, phenylanthracenylene group, bisanthracenylene group, dianthracenylbenzynylene group and dibenzoanthracenylene group. Among the above, naphtylene group, anthracenylene group, phenanthrylene group, chrysenylene group, pyrenylene group and benzoanthracenylene group are preferable.

The aryl group having 6 to 30 carbon atoms, the heterocyclic group having 5 to 30 ring carbon atoms and the alkyl group having 6 to 30 carbon atoms in the formula (20) may be the group explained with reference to the above formulae (1) and (b-1) to (b-6).

The aralkyl group having 7 to 30 carbon atoms in the formula (20) is represented by -Rv-Rw. Rv is exemplified by an alkylene group corresponding to the alkyl group having 1 to 30 carbon atoms. Rw is exemplified by the examples of the above aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms, and an alkyl moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, α-naphthylmethyl group, 1-α-naphthylethyl group, 2-α-naphthylethyl group, 1-α-naphthylisopropyl group, 2-α-naphthylisopropyl group, 1-pyrorylmethyl group, 2-(1-pyroryl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

At least one of $Ar_1$ to $Ar_4$ in the above formula (20) is preferably represented by a formula (21) below, (21)

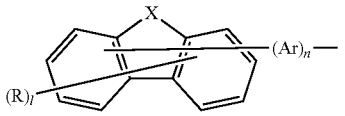

In the above formula (21):

n represents an integer in a range from 0 to 3, m represents an integer in a range from 0 to 5 and 1 represents an integer in a range from 0 to 7;

X represents an oxygen atom, a sulfur atom or a selenium atom;

Ar is a substituted or unsubstituted arylene group having 6 to 30 ring carbon atoms;

R represents a halogen atom, a cyano group, a nitro group, a hydroxyl group, a silyl group, a carboxyl group, a substituted or unsubstituted aryl group having 6 to 30 ring carbon atoms, a substituted or unsubstituted alkyl group having 1 to 30 carbon atoms, a substituted or unsubstituted alkylamino group having 1 to 30 carbon atoms, a substituted or unsubstituted arylamino group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted arylthio group having 6 to 30 ring carbon atoms, or a substituted or unsubstituted alkoxycarbonyl group having 1 to 30 carbon atoms; a plurality of Ar and R are mutually the same or different when n, m and 1 are 2 or more; and when plural R are present, the plural R may bond to each other to form a saturated or unsaturated five-membered or six-membered ring structure that may be substituted.

In the above formula (21), the aryl group having 6 to 30 ring carbon atoms, the alkyl group having 1 to 30 carbon atoms, the alkylamino group having 1 to 30 carbon atoms, the arylamino group having 6 to 60 ring carbon atoms, the alkoxy group having 1 to 30 carbon atoms, the aryloxy group having 6 to 30 ring carbon atoms and the arylthio group having 6 to 30 ring carbon atoms may be the groups explained with reference to the above formulae (2) to (6) and (51).

The alkoxycarbonyl group having 1 to 30 carbon atoms is represented by —COORv. Examples of Rv are the same as the examples of the alkyl group having 1 to 30 carbon atoms.

The thickness of the emitting layer is preferably in a range from 5 nm to 50 nm, more preferably from 7 nm to 50 nm, the most preferably from 10 nm to 50 nm. The thickness of less than 5 nm may cause difficulty in forming the emitting layer and in controlling chromaticity, while the thickness of more than 50 nm may raise drive voltage.

In the emitting layer, a ratio of the host material and the fluorescent dopant material is preferably in a range of 99:1 to 50:50 at a mass ratio.

Further, the above-described host material and the dopant material are preferably a compound satisfying the following specific conditions. The specific conditions will be described below.

It is preferable that singlet energy EgS(H) of the host material and singlet energy EgS(D) of the dopant material satisfy the relationship according to the following numerical formula (1) and the difference ΔST(H) of the host material between the singlet energy EgS(H) and an energy gap $Eg_{77K}(H)$ at 77K satisfies the relationship according to the following numerical formula (2).

$$EgS(H)>EgS(D) \quad (1)$$

$$\Delta ST(H)=EgS(H)-Eg_{77K}(H)<0.3\ [eV] \quad (2)$$

Further, a difference ΔT between the energy gap $Eg_{77K}(H)$ at 77K of the host material and an energy gap $Eg_{77K}(T)$ at 77K of the dopant material satisfies a relationship of the following numerical formula (3).

$$\Delta T=Eg_{77K}(H)-Eg_{77K}(D)\geq 0.6\ [eV] \quad (3)$$

ΔST

The organic EL device emits light at a high efficiency in a high current density area by using a compound having a small energy gap (ΔST) between singlet energy EgS and triplet energy EgT as the host material. The ΔST(H) refers to ΔST of the host material.

From quantum chemical viewpoint, decrease in the energy difference (ΔST) between the singlet energy EgS and the triplet energy EgT can be achieved by a small exchange interaction therebetween. Physical details of the relationship between ΔST and the exchange interaction are exemplarily described in the following:

Literature 5: Organic EL Symposium, proceeding for the tenth meeting edited by Chihaya Adachi et al., S2-5, pp. 11-12; and Literature 6: Organic Photochemical Reaction Theory edited by Katsumi Tokumaru, Tokyo Kagaku Dojin Co., Ltd. (1973).

Such a material can be synthesized according to molecular design based on quantum calculation. Specifically, the material is a compound in which a LUMO electron orbit and a HOMO electron orbit are localized to avoid overlapping.

Examples of the compound having a small ΔST, which is used as the host material in the exemplary embodiment, are compounds in which a donor element is bonded to an acceptor element in a molecule and ΔST is in a range of 0 eV or more and less than 0.3 eV in terms of electrochemical stability (oxidation-reduction stability).

A more preferable compound is such a compound that dipoles formed in the excited state of a molecule interact with each other to form an aggregate having a reduced exchange interaction energy. According to analysis by the inventors, the dipoles are oriented substantially in the same direction in the compound, so that ΔST can be further reduced by the interaction of the molecules. In such a case, ΔST can be extremely small in a range of 0 eV to 0.2 eV.

Aggregate

Figure 2:
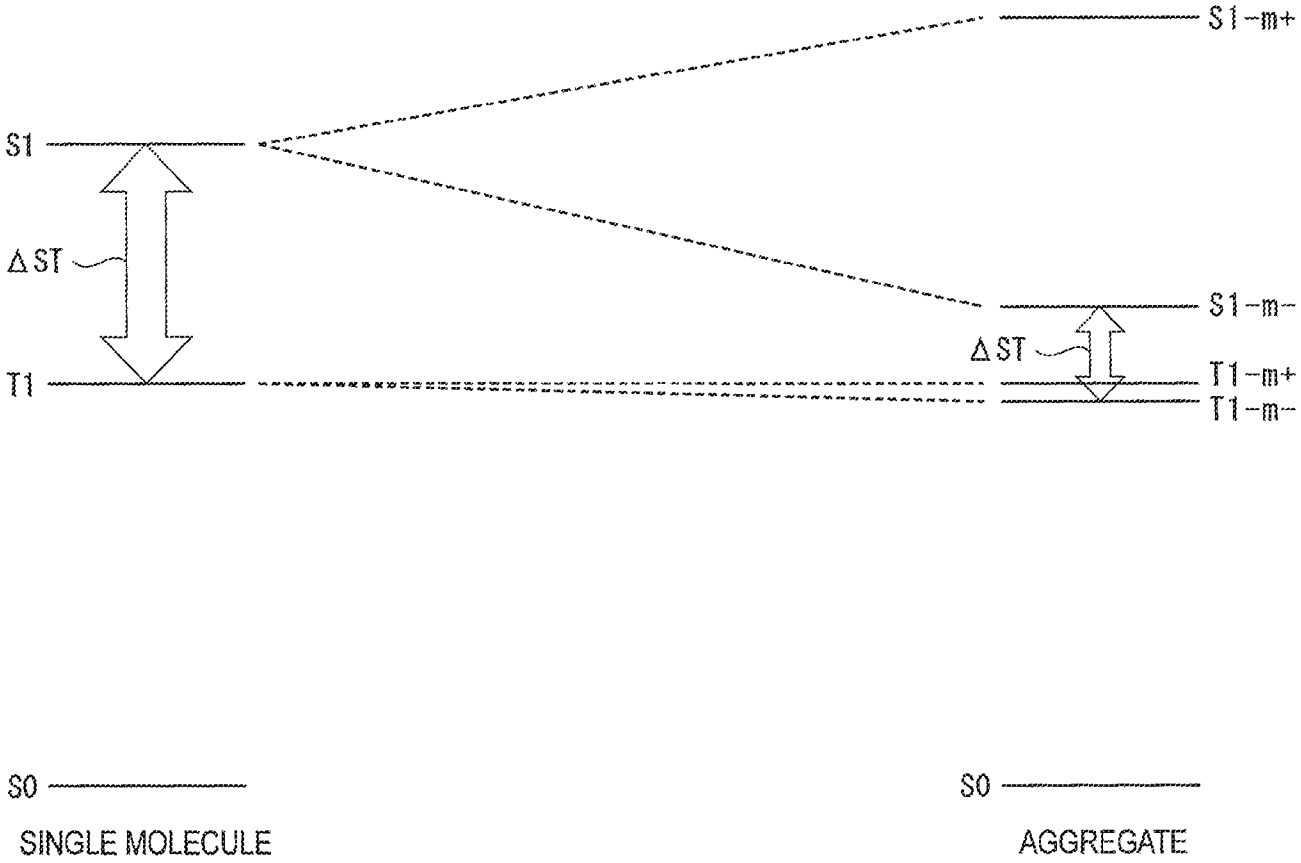
FIG. 2 shows an example of physics models with aggregate formation.

Decrease in the energy gap (ΔST) between the singlet energy EgS and the triplet energy EgT can also be achieved by aggregate formation. Herein, the aggregate does not reflect an electronic state by a single molecule, but the aggregate is provided by several molecules physically approaching each other. After the plurality of molecules approach each other, electronic states of a plurality of molecules are mixed and changed, thereby changing an energy level. A value of singlet energy is mainly decreased, thereby decreasing a value of ΔST. The decrease in the value of ΔST by the aggregate formation can also be explained by Davydov splitting model showing that two molecules approach each other to change electronic states thereof (see FIG. 2). As shown in Davydov splitting model, it is considered that change of the electronic states by two molecules different from change of an electronic state by a single molecule is brought about by two molecules physically approaching each other. A singlet state exists in two states represented by $S1\text{-}m^+$ and $S1\text{-}m^-$. A triplet state exists in two states represented by $T1\text{-}m^+$ and $T1\text{-}m^-$. Since $S1\text{-}m^-$ and $T1\text{-}m^-$ showing a lower energy level exist, ΔST representing a gap between $S1\text{-}m^-$ and $T1\text{-}m^-$ becomes smaller than that in the electronic state by a single molecule.

The Davydov splitting model is exemplarily described in the following:

Literature 7: J. Kang, et al, International Journal of Polymer Science, Volume 2010, Article ID 264781;

Literature 8: M. Kasha, et al, Pure and Applied Chemistry, Vol. 11, pp 371, 1965; and Literature 9: S. Das, et al, J. Phys. Chem. B. vol. 103, p 209, 1999.

The inventors found usage of sublevels of a singlet state and a triplet state of a compound easily forming an aggregate in a thin film, and consequent possibility of promotion of inverse intersystem crossing by molecules and aggregates in the thin film.

For instance, a compound having a large half bandwidth of a photoluminescence spectrum is considered to easily form an aggregate in a thin film of the compound. A relationship between the half bandwidth of the photoluminescence spectrum and easy formability of the aggregate can be estimated as follows.

In a compound having a property of typically existing as a single molecule without forming an aggregate, a vibrational level is less recognized in the singlet state, so that a narrow half bandwidth of the photoluminescence spectrum is observed. For instance, CBP (4,4'-bis[9-dicarbazolyl]-2,2'-biphenyl) exhibits a property to typically exist as a single molecule, in which a half bandwidth of a photoluminescence spectrum is relatively as narrow as about 50 nm.

On the other hand, in the compound easily forming the aggregate, a plurality of molecules electronically influence each other, whereby a lot of vibrational levels exist in the singlet state. As a result, since the vibrational levels of the singlet state are often relaxed to the ground state, the half bandwidth of the photoluminescence spectrum is increased.

Such a compound easily forming the aggregate is expected to have a lot of vibrational levels even in a triplet state. Consequently, it is speculated that ΔST in relation to heat is decreased through the sublevels to promote the inverse intersystem crossing, since a lot of sublevels exist between the singlet state and the triplet state.

It should be noted that the aggregate according to the exemplary embodiment means that a single molecule forms any aggregate with another single molecule. In other words, a specific aggregate state is not shown in the exemplary embodiment. An aggregate state of an organic molecule is probably formable in various states in a thin film, which is different from an aggregate state of an inorganic molecule.

TADF Mechanism

As described above, when ΔST(H) of the organic material is small, inverse intersystem crossing from the triplet level of the host material to the singlet level thereof is easily caused by heat energy given from the outside. Herein, an energy state conversion mechanism to perform spin exchange from the triplet state of electrically excited excitons within the organic EL device to the singlet state by inverse intersystem crossing is referred to as TADF Mechanism.

In the exemplary embodiment, since the material having a small ΔST(H) is used as the host material, inverse intersystem crossing from the triplet level of the host material to the singlet level thereof is easily caused by heat energy given from the outside.

Figure 3:
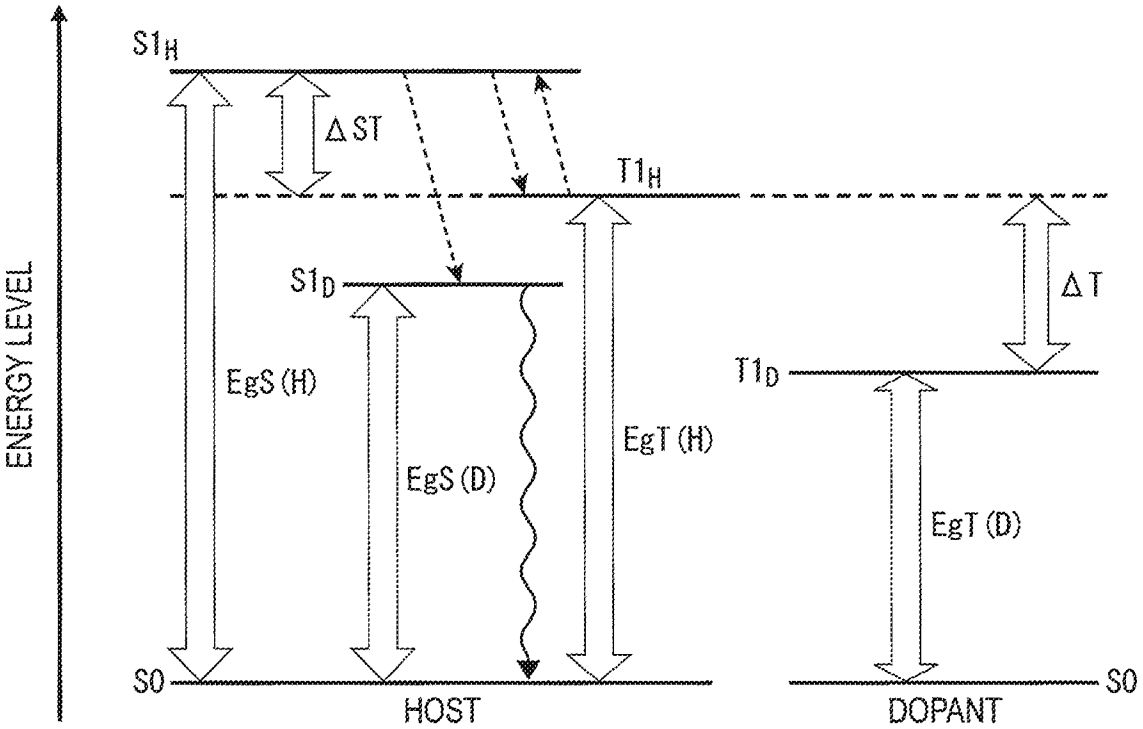
FIG. 3 shows a relationship in energy level between the host material and the dopant material in the emitting layer.

FIG. 3 shows a relationship in energy level between the host material and the dopant material in the emitting layer. In FIG. 3, S0 represents a ground state, $S1_H$ represents a lowest singlet state of the host material, $T1_H$ represents a lowest triplet state of the host material, $S1_D$ represents a lowest singlet state of the dopant material, and $T1_D$ represents a lowest triplet state of the dopant material. As shown in FIG. 3, a difference between $S1_H$ and $T1_H$ corresponds to ΔST(H), a difference between $S1_H$ and S0 corresponds to EgS(H), a difference between $S1_D$ and S0 corresponds to EgS(D), and a difference between $T1_H$ and $T1_D$ corresponds to ΔT. A dotted-line arrow shows energy transfer between the respective excited states in FIG. 3.

As described above, a compound having a small ΔST(H) is selected as the compound for the host material in the exemplary embodiment. This is because the material having a small ΔST(H) is considered to easily cause inverse intersystem crossing from the triplet excitons generated in the lowest triplet state $T1_H$ to the lowest singlet state $S1_H$ of the host material by heat energy. Due to the small ΔST(H), inverse intersystem crossing is easily caused, for instance, even around a room temperature. When the inverse intersystem crossing is thus easily caused, a ratio of energy transfer from the host material to the lowest singlet state [$T1_D$] $S1_D$ of the fluorescent dopant material is increased by Förster transfer, resulting in improvement in a luminous efficiency of a fluorescent organic EL device.

In other words, use of the compound having a small ΔST(H) as the host material increases emission by the TADF mechanism, so that a delayed fluorescence ratio becomes large. When the delayed fluorescence ratio is large, a high internal quantum efficiency is achievable. It is considered that the internal quantum efficiency can be theoretically raised up to 100% even by using delayed fluorescence by the TADF mechanism.

Figure 4:
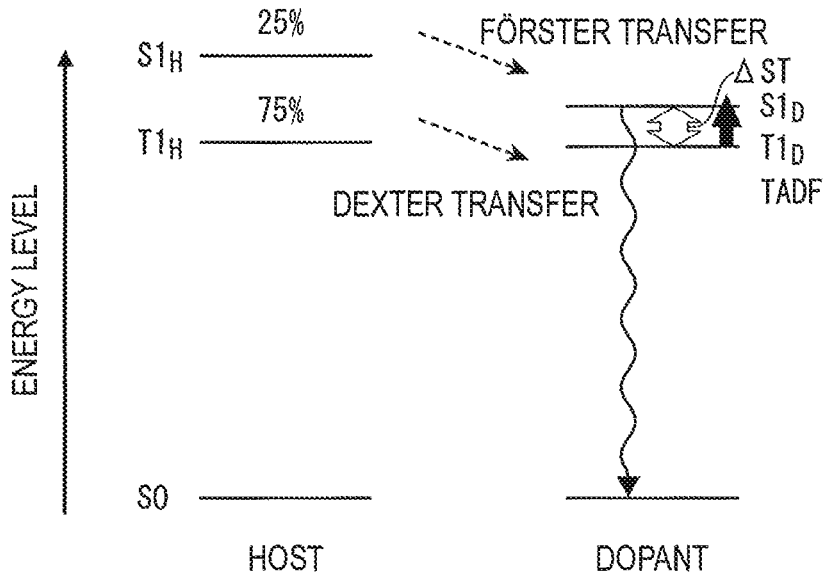
FIG. 4 shows a relationship in energy level between the host material and the dopant material in the emitting layer.

FIG. 4 shows a relationship in energy level between the host material and the dopant material in the emitting layer in the TADF mechanism described in Literature 5. In FIG. 4, S0, $S1_H$, $T1_H$, $S1_D$, and $T1_D$ represent the same as those in FIG. 3. A dotted-line arrow shows energy transfer between the respective excited states. As shown in FIG. 4, a material having a small ΔST(D) is used as the dopant material in the TADF mechanism described in Literature 3. Accordingly, energy is transferred from the lowest triplet state $T1_H$ of the host material to the lowest triplet state $T1_D$ of the dopant material by Dexter transfer. Further, inverse intersystem crossing from the lowest triplet state $T1_D$ to the lowest singlet state $S1_D$ of the dopant material is possible by heat energy. As a result, fluorescent emission from the lowest [triplet state $T1_D$] *single state* $S1_D$ of the dopant material can be observed. It is considered that the internal quantum efficiency can be theoretically raised up to 100% also by using delayed fluorescence by the TADF mechanism.

The inventors herein employ a fluorescent compound having a small ΔST(H) as described in Literature 3 as a host material in a host-dopant system. The reasons are detailed as follows.

First, considering conversion of energy states on the dopant material by the TADF mechanism, the dopant material has a relatively high singlet energy for fluorescent emission and triplet energy approximately equivalent to the singlet energy. In order to efficiently trap the triplet energy within the emitting layer, it is necessary to select a host material having larger triplet energy. If a typical organic material usually having a large ΔST is used as the host material, the singlet energy of the host material, i.e., an energy gap between a HOMO level and a LUMO level becomes extremely large. As a result, an energy gap between the host material and a carrier transporting layer adjacent to the emitting layer becomes large, so that injection of carriers to the emitting layer is considered to become difficult. Accordingly, the inventors consider that conversion of the energy states by the TADF mechanism is preferably performed on the host material, whereby the carriers are advantageously injected to the emitting layer and are easily balanced in the entire organic EL device.

Secondly, the inventors believe it possible to suppress decrease in a luminous efficiency caused by Triplet-Triplet-Annihilation in a high current density area by using the fluorescent compound having a small ΔST(H) as the host material. Herein, Triplet-Triplet-Annihilation (hereinafter, referred to as TTA) is a physical phenomenon in which long-life triplet excitons generated on a molecule are adjacent to each other at a high density to collide with each other and are thermally deactivated.

The inventors believe it possible to suppress decrease in the luminous efficiency in the high current density area to some extent in the host-dopant system in which the triplet energy is difficult to transit from the host material to the dopant material. In the exemplary embodiment, the compound having a small ΔST is used as the host material of the emitting layer. After inverse intersystem crossing from a triplet excited level of the host material to a singlet excited level thereof by the TADF mechanism, energy is transferred to a singlet excited level of the dopant material. Accordingly, the generated triplet excitons are kept in a triplet excited state on the host material whose abundance ratio is high in the emitting layer. On the other hand, if the compound having a small ΔST is used as the dopant material in the emitting layer, the generated triplet excitons are kept in a triplet excited state on the dopant material whose abundance ratio is extremely low in the emitting layer. In other words, the inventors believe it preferable to design a system that avoids concentration of triplet excited state on the dopant material in driving the organic EL device in the high current density area. Accordingly, in the exemplary embodiment, the inventors employ the material having a small ΔST(H) as the host material.

Thirdly, a material having a high emission quantum efficiency can be easily selected as the dopant material by using a material causing inverse intersystem crossing from the triplet level to the singlet level as the host material. As a result, emission of the singlet excitons is quickly relaxed after energy transfer thereof to the dopant material, so that energy quenching in the high current density area is suppressible. In the host-dopant system in a fluorescent device, generally, the host material has a carrier transporting function and an exciton generating function and the dopant material has an emission function. This system is for separating the carrier transporting function and the emission function of the emitting layer. Accordingly, effective organic EL emission is promoted by doping a small amount of a dopant material having a high emission quantum efficiency into the emitting layer. The emitting layer according to the exemplary embodiment is required to have a function to cause inverse intersystem crossing by the TADF function in addition to a typical function of the emitting layer. By requiring the host material to have the function to cause inverse intersystem crossing by the TADF mechanism, the inventors increased options for the dopant material having a high emission quantum efficiency which largely contributes to the luminous efficiency of the organic EL device. With this arrangement, a fluorescent dopant material typically known as being highly efficient can be selected.

Relationship Between EgT and $Eg_{77K}$

In this exemplary embodiment, the compound having ΔST of a predetermined value or less is used. The aforementioned triplet energy EgT is different from a typically defined triplet energy. Such a difference will be described below.

For general measurement of the triplet energy, a target compound to be measured is dissolved in a solvent to form a sample. A phosphorescent spectrum (ordinate axis: phosphorescent luminous intensity, abscissa axis: wavelength) of the sample is measured at a low temperature (77K). A tangent is drawn to the rise of the phosphorescent spectrum on the short-wavelength side. The triplet energy is calculated by a predetermined conversion equation based on a wavelength value at an intersection of the tangent and the abscissa axis.

As described above, the compound for the host material in the exemplary embodiment has a small ΔST. When ΔST is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish emission from the singlet state from emission from the triplet state, the value of the triplet energy is basically considered dominant.

Accordingly, in order to distinguish the triplet energy EgT in the exemplary embodiment from the typical triplet energy EgT in a strict meaning although the measurement method is the same, the triplet energy EgT in the exemplary embodiment is defined as follows. A target compound to be measured is dissolved in a solvent to form a sample. A phosphorescent spectrum (ordinate axis: phosphorescent luminous intensity, abscissa axis: wavelength) of the sample is measured at a low temperature (77K). A tangent is drawn to the rise of the phosphorescent spectrum on the short-wavelength side. Energy is calculated as an energy gap $Eg_{77K}$ by a predetermined conversion equation based on a wavelength value at an intersection of the tangent and the abscissa axis. ΔST is defined as a difference between the singlet energy EgS and the energy gap $Eg_{77K}$. Accordingly, ΔST(H) is represented by the formula (1).

The triplet energy measured in a solution state may include an error by interaction between the target molecule and the solvent. Accordingly, as an ideal condition, a measurement in a thin film state is desired in order to avoid the interaction between the target molecule and the solvent. In this exemplary embodiment, the molecule of the compound used as the host material exhibits a photoluminescence spectrum having a broad half bandwidth in a solution state, which strongly implies aggregate formation also in the solution state. Accordingly, the solution state is considered to be under the same conditions as in a thin film state. Consequently, in this exemplary embodiment, a measurement value of the triplet energy in the solution state is used.

Singlet Energy EgS

The singlet energy EgS in the exemplary embodiment is defined based on calculation by a typical method. Specifically, the target compound is deposited on a quartz substrate to prepare a sample. An absorption spectrum (ordinate axis: absorbance, abscissa axis: wavelength) of the sample is measured at a normal temperature (300K). A tangent is drawn to the rise of the absorption spectrum on the long-wavelength side. The singlet energy EgS is calculated by a predetermined conversion equation based on the tangent and the wavelength value at the intersection. EgS in aggregate formation corresponds to an energy gap between S1-$m^-$ and the ground state S0 in the Davydov splitting model.

The calculation of the singlet energy EgS and the energy gap $Eg_{77K}$ will be described in detail later.

Delayed Fluorescence Ratio

It was found that a delayed fluorescence ratio according to the organic EL device of the exemplary embodiment exceeds the theoretical upper-limit of a delayed fluorescence ratio (TTF ratio) of a case where it is assumed that delayed fluorescence is caused only by the TTF mechanism. In other words, according to the exemplary embodiment, an organic EL device having a higher internal quantum efficiency is achievable.

The delayed fluorescence ratio is measurable by a transitional EL method. The transitional EL method is for measuring reduction behavior (transitional property) of EL emission after pulse voltage applied on the device is removed. EL luminous intensity is classified into a luminescence component from singlet excitons generated in first recombination and a luminescence component from singlet excitons generated through triplet excitons. Since lifetime of the singlet excitons generated in the first recombination is very short at a nano-second order, EL emission is rapidly reduced after removal of pulse voltage.

On the other hand, since delayed fluorescence provides emission from singlet excitons generated through long-life triplet excitons, EL emission is gradually reduced. Thus, since there is a large difference in time between emission from the singlet excitons generated in the first recombination and emission from the singlet excitons derived from the triplet excitons, a luminous intensity derived from delayed fluorescence is obtainable. Specifically, the luminous intensity can be determined by the following method.

Figure 5:
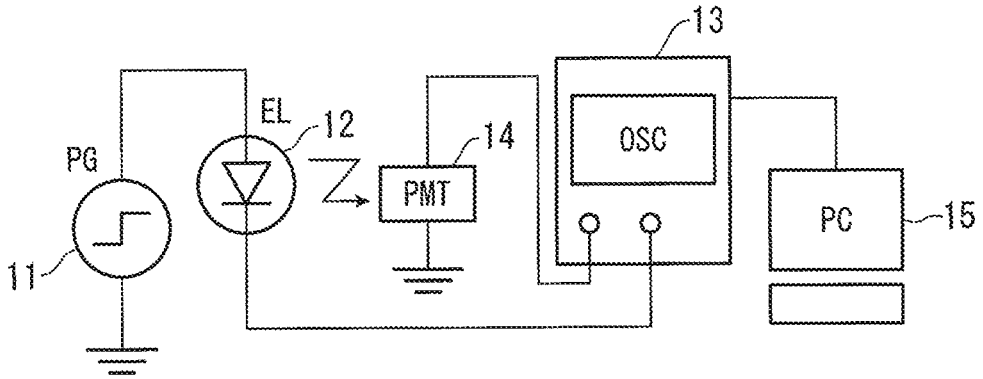
FIG. 5 shows a measurement system of transitional EL waves.

Transitional EL waveform is measured as follows (see FIG. 5). Pulse voltage waveform outputted from a voltage pulse generator (PG) 11 is applied on an organic EL device (EL) 12. The applied voltage waveform is loaded in an oscilloscope (OSC) 13. When pulse voltage is applied on the organic EL device 12, the organic EL device 12 generates pulse emission. This emission is loaded in the oscilloscope (OSC) 13 through a photomultiplier (PMT) 14. The voltage waveform and the pulse emission are synchronized and loaded in a personal computer (PC) 15.

The ratio of luminous intensity derived from delayed fluorescence is defined as follows based on analysis of the transitional EL waveform. It should be noted that a formula to calculate a TTF ratio described in International Publication No. WO2010/134352 may be used for calculation of the ratio of luminous intensity derived from delayed fluorescence.

It is considered that a delayed fluorescence component defined in the exemplary embodiment includes thermally activated delayed fluorescence (TADF mechanism) described in the exemplary embodiment in addition to the luminescence component derived from TTF. For this reason, in the exemplary embodiment, a ratio of the delayed fluorescence component calculated according to the following numerical formula (4) is referred to as a delayed fluorescence ratio, not as a TTF ratio.

The delayed fluorescence ratio is calculated according to the numerical formula (4).

$$\frac{1}{\sqrt{I}} \propto A + \gamma \cdot t \tag{4}$$

In the numerical formula (4), I represents luminous intensity derived from delayed fluorescence. A represents a constant. The measured transitional EL waveform data is fit in the numerical formula (4) to obtain the constant A. Here, a luminous intensity $1/A^2$ at the time t=0 when pulse voltage is removed is defined as the ratio of luminous intensity derived from delayed fluorescence.

Figure 6A:
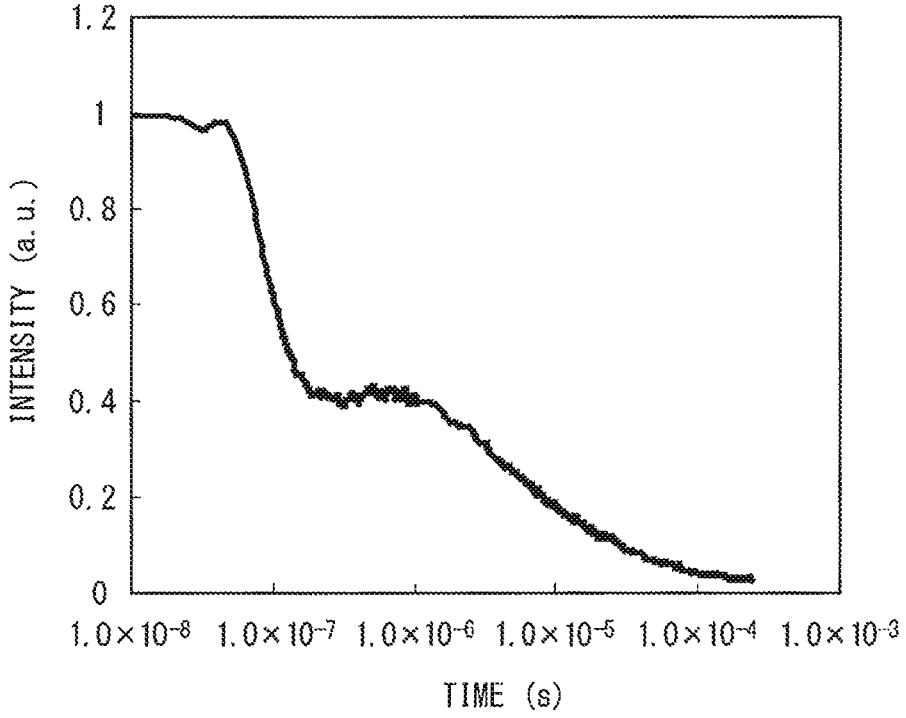
FIG. 6A shows a measurement method of a ratio of luminous intensities derived from delayed fluorescence and is a graph showing time-varying luminous intensities of the EL device.

A graph of FIG. 6(A) shows a measurement example where a predetermined pulse voltage is applied on the organic EL device and then the pulse voltage is removed and shows time-varying luminous intensities of the organic EL device.

The pulse voltage was removed at the time of about $3\times10^{-8}$ seconds in the graph of FIG. 6 (A). In the graph of FIG. 6(A), the luminous intensity when the voltage is removed is defined as 1.

After rapid reduction before the elapse of about $2\times10^{-7}$ seconds after the voltage removal, a gradual reduction component appears.

Figure 6B:
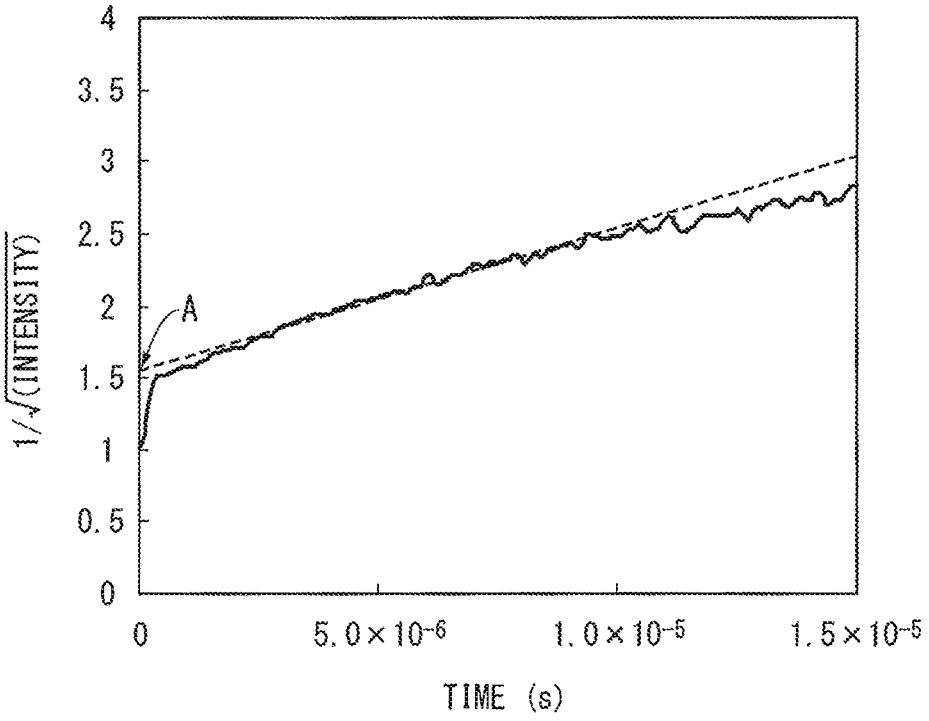
FIG. 6B shows a measurement method of a ratio of luminous intensities derived from delayed fluorescence and is a graph showing time-varying inverse square root of luminous intensities.

In the graph of FIG. 6(B), the voltage removal time is a starting point and the inverse square root of luminous intensity before the elapse of $1.5\times10^{-5}$ seconds after voltage removal is plotted. Fitting is conducted as follows.

A value at an intersection A of the ordinate axis and the linear line extended to the starting point is 1.55. Accordingly, the ratio of luminous intensity derived from the delayed fluorescence obtained from the transitional EL waveform is $1/(1.55)^2=0.41$, which means 41% of the luminous intensity was derived from the delayed fluorescence. In other words, the ratio of luminous intensity exceeds 37.5%, i.e., the supposed theoretical upper-limit of the TTF ratio.

The luminous intensity derived from the delayed fluorescence obtained from the transitional EL waveform is variable in accordance with measurement temperatures. Such a phenomenon is considered to be inherent mostly in fluorescent emission by the TADF mechanism.

The luminous intensity is preferably fitted in a linear line by the method of least squares. In this case, the luminous intensity before the elapse of $10^{-5}$ seconds is preferably fitted.

Figure 7:
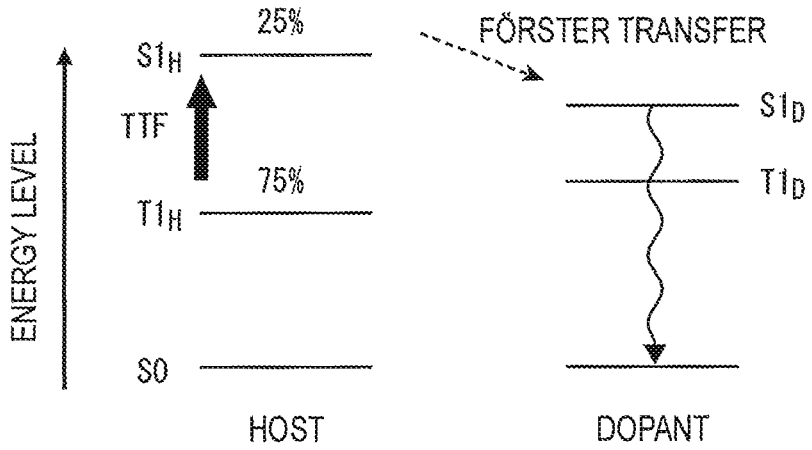
FIG. 7 shows a relationship in energy level between the host material and the dopant material in the emitting layer.

The TTF mechanism having an emission mechanism by delayed fluorescence will be described using FIG. 7. FIG. 7 shows a relationship in energy level between the host material and the dopant material in an organic EL device using the TTF mechanism. In FIG. 7, S0, $S1_H$, $T1_H$, $S1_D$ and $T1_D$ represent the same as those in FIG. 3. An arrow shows energy transfer between the respective excited states in FIG. 7.

As described above, the TTF mechanism utilizes a phenomenon in which singlet excitons are generated by collision between two triplet excitons. As shown in FIG. 7, it is preferable that the lowest triplet state $T1_H$ of the host material is lower than the lowest triplet state $T1_D$ of the dopant material, so that triplet excitons concentrate on molecules of the host material. The triplet excitons efficiently collide with each other in accordance with increase in the density of the triplet excitons, whereby the triplet excitons are partially changed into singlet excitons. The lowest singlet state $S1_H$ of the host material generated by the TTF mechanism is immediately transferred to the lowest singlet state $S1_D$ of the dopant material by Förster transfer, so that the dopant material emits fluorescence.

The theoretical upper-limit of the TTF ratio can be obtained as follows.

According to S. M. Bachilo et al. (J. Phys. Chem. A, 104, 7711 (2000)), assuming that high-order excitons such as quintet excitons are quickly returned to triplet excitons, triplet excitons (hereinafter abbreviated as $^3A^*$) collide with one another when the density thereof is increased, whereby a reaction shown by the following numerical formula (5) occurs. In the formula, $^1A$ represents the ground state and $^1A^*$ represents the lowest singlet excitons.

$$^3A^*+{}^3A^*\rightarrow(4/9)^1A+(1/9)^1A^*+(13/9)^3A^* \quad (5)$$

Specifically, $$5\,^3A^*\rightarrow4\,^1A+{}^1A^*$$

It is expected that, among triplet excitons initially generated, which account for 75%, one fifth thereof (i.e., 20%) is changed to singlet excitons.

Accordingly, the amount of singlet excitons which contribute to emission is 40%, which is a value obtained by adding 15% (75%×(1/5)=15%) to 25% (the amount ratio of initially generated singlet excitons).

At this time, a ratio of luminous intensity derived from TTF (TTF ratio) relative to the total luminous intensity is 15/40, i.e., 37.5%. Thus, it is recognized that the delayed fluorescence ratio of the organic EL device according to the exemplary embodiment exceeds the theoretical upper-limit of only the TTF ratio.

Residual Strength Ratio in 1 μs

A method for relatively measuring an amount of delayed fluorescence is exemplified by a method for measuring a residual strength in 1 μs. The residual strength in 1 μs is defined as a ratio of a luminous intensity after the elapse of 1 μs after removal of a pulse voltage measured by a transitional EL method to a luminous intensity at the time of the removal of the pulse voltage. The relative amount of delayed fluorescence can be estimated based on reduction behavior of EL emission after the removal of the pulse voltage measured by the transitional EL method. The residual strength ratio in 1 μs can be obtained by reading luminous intensity at the time of 1.0 μs in the graph of FIG. 6A.

The residual strength ratio in 1 μs is preferably larger than 36.0%, more preferably 38.0% or more.

Dopant Properties

A preferable dopant in the exemplary embodiment has properties to emit fluorescence and to have a large speed constant of radiational transition. In this arrangement, singlet excitons electrically excited on the host material, singlet excitons generated by the TADF mechanism and the like are transferred to singlet excitons of the dopant material by Förster energy transfer and the dopant material immediately emits light. In other words, fluorescent emission is possible through the above energy transition before triplet excitons on the host material causes TTA, by which decrease in an efficiency in the high current area is likely to be considerably improved.

It is preferable to select a dopant material having a fluorescence lifetime of 5 ns or less, more preferably 2 ns or less as the dopant material having a large speed constant of radiational transition in the exemplary embodiment. A fluorescence quantum efficiency of the dopant material is preferably 80% or more in a solution. The fluorescence quantum efficiency can be obtained by measuring the dopant material in a range of $10^{-5}$ mol/l to $10^{-6}$ mol/l of a concentration in a toluene solution using Absolute PL Quantum Yield Measurement System C9920-02 manufactured by HAMAMATSU PHOTONICS K.K.

It is also expected by measuring an EL spectrum of the device and confirming a luminescence component of a material other than the dopant material is 1/10 or less of the luminescence component of the dopant that the dopant material has a large speed constant of radiational transition.

Relationship Between Emitting Layer and Electron Transporting Layer

When ΔST(H) of the host material is small, the energy gap between the host material and the electron transporting layer adjacent thereto is small, so that the electrons are likely to be injected into the emitting layer. As a result, carrier balance is easily obtainable to decrease roll-off.

Relationship Between Emitting Layer and Hole Transporting Layer

When an ionization potential of the hole transporting layer is represented by $IP_{HT}$, $IP_{HT}\leq5.7$ eV is preferable. With this arrangement, balance between the electrons and the holes can be enhanced. The ionization potential can be obtained, for instance, by measuring the material in a form of a thin film using a photoelectron spectroscopy (AC-3: manufactured by RIKEN KEIKI Co., Ltd.).

Relationship in Singlet Energy Between Host Material and Dopant Material

In the exemplary embodiment, the dopant material is a fluorescent dopant material. A compound used as the host material and a compound used as the dopant material satisfy a relationship represented by the numerical formula [(2)] (*1*) in terms of the singlet energy.

When such a relationship is satisfied, energy of the singlet excitons initially generated on the host material and the singlet excitons derived from the delayed fluorescence is easily transferred to the dopant material. Consequently, the dopant efficiently emits fluorescence.

Δn

The inventors found that one way to reduce ΔST is to use the compound forming the aggregate and that the compound having a large Δn easily forms the aggregate in a film of the compound. Herein, Δn is a value representing the largest difference between the refractive index $n_Z$ perpendicular to the silicon substrate surface and the refractive index $n_X$ parallel to the silicon substrate surface in an area where a reflectivity to be observed simultaneously with a refractivity is not observed, in the spectroscopic ellipsometry measurement (measurement range: 200 nm to 1000 nm).

A relationship between Δn and easy formability of the aggregate is estimated as follows.

When a large difference is generated between a refractive index n in a vertical direction z relative to the silicon substrate and a refractive index n in a parallel direction x relative to the silicon substrate, it is considered that molecules exist with a certain regularity in a thin film state. In other words, the compound used as the host material in the exemplary embodiment is expected to have a predetermined value of Δn while forming the aggregate in the thin film state to exhibit a certain regularity.

On the other hand, a compound having an extremely small Δn (e.g., CBP and $Alq_3$(tris(8-hydroxyquinolinato)aluminium)) exists in an amorphous state in which molecules have no regularity in a thin film state.

The relationship between Δn and easy formability of the aggregate is described in the following:

Literature 10: D. Yokoyama et al., Org. Electron. 10, 127-137 (2009);

Literature 11: D. Yokoyama et al., Appl. Phys. Lett. 93, 173302 (2008); and

Literature 12: D. Yokoyama et al., Appl. Phys. Lett. 95, 243303 (2009).

Figure 8A:
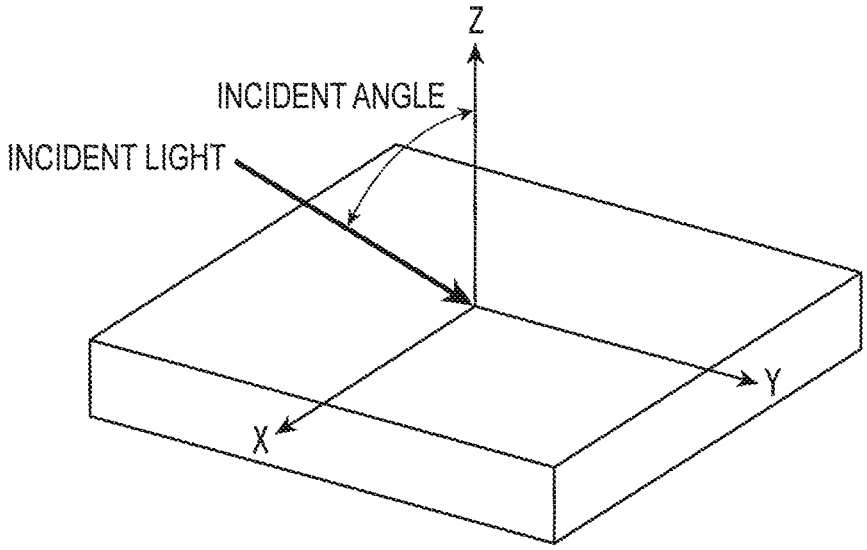
FIG. 8A schematically shows an incident angle of an incident light from a light source as an example of spectroscopic ellipsometry measurement.
Figure 8B:
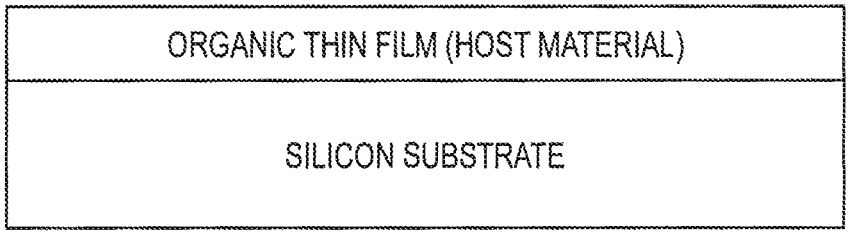
FIG. 8B shows a cross section of an organic thin film on a silicon substrate (a measurement target) as an example of the spectroscopic ellipsometry measurement.

Δn can be calculated based on the refractive index of each compound measured by the spectroscopic ellipsometry method. The spectroscopic ellipsometry method is a measurement method of an optical constant (i.e., a refractive index n and an extinction coefficient k) and a thickness of a thin film. For instance, a variable-incident-angle high-speed spectroscopic ellipsometer (M–2000D: manufactured by J. A. Woollam Co., Inc.) is usable. FIGS. 8A and 8B show an example of spectroscopic ellipsometry measurement. FIG. 8A shows an incident angle of an incident light from a light source. FIG. 8B shows a cross section of an organic thin film (a measurement target) on a silicon substrate.

Each compound is deposited on the silicon substrate (Si (100)) to form a 100-nm organic thin film. Using the variable-incident-angle high-speed spectroscopic ellipsometer (M-2000D: manufactured by J. A. Woollam Co., Inc.), ellipsometric parameters yi and A are measured at every five degrees in a range of 45 degrees to 80 degrees of an incident angle and at every 1.6 nm in a range of 200 nm to 1000 nm of a wavelength. The obtained parameters are analyzed together using an analysis software WVASE32 (manufactured by J. A. Woollam Co., Inc) to examine optical anisotropy of the film. The anisotropy of the optical constant (i.e., the refractive index n and the extinction coefficient k) of the film reflects the anisotropy of molecular orientation in the film. The measurement method and the analysis methods are described in detail in the above Literatures 10 to 12.

Δn can be obtained as a difference between the refractive index n in the perpendicular direction z relative to the silicon substrate and the refractive index n in the parallel direction x relative to a surface of the silicon substrate. The perpendicular direction z and the parallel direction x relative to the surface of the silicon substrate are shown in FIG. 8A.

Half Bandwidth

A half bandwidth represents a width of an emission spectrum when a luminous intensity becomes half relative to the maximum luminous intensity of the emission spectrum. The inventors found that a host material having 50 nm or more of a half bandwidth of a photoluminescence spectrum is a material easily forming an aggregate state and easily causing inverse intersystem crossing in a thin film. Accordingly, the TADF mechanism easily works in the host material having 50 nm or more of the half bandwidth of the photoluminescence spectrum. Particularly preferably, the half bandwidth of the photoluminescence spectrum of the host material is 65 nm or more.

ΔT

It is preferable that a difference ΔT between triplet energy $Eg_{77K}$(H) of the host material and triplet energy $Eg_{77K}$(D) of the dopant material satisfies a relationship represented by the numerical formula (3). ΔT is more preferably 0.8 eV or more, further preferably 1.0 eV or more.

When ΔT satisfies the relationship represented by the numerical formula (3), energy of the triplet excitons generated by recombination on the host material becomes difficult to transfer to the triplet level of the dopant material, and thermal deactivation of the triplet excitons becomes difficult. Consequently, the dopant efficiently emits fluorescence.

Examples of the compound used as the host material in the exemplary embodiment are shown below. However, the host material in the exemplary embodiment is not limited thereto.

H-1

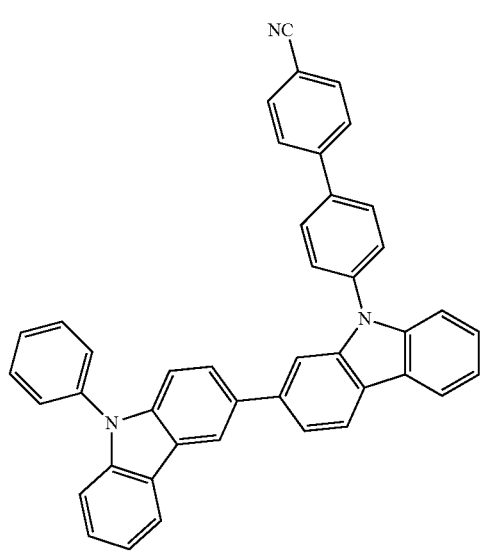

-continued

H-2

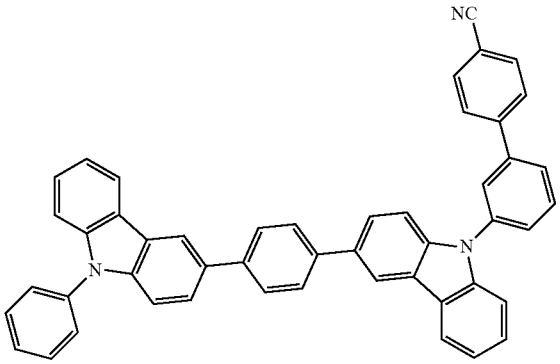

H-3

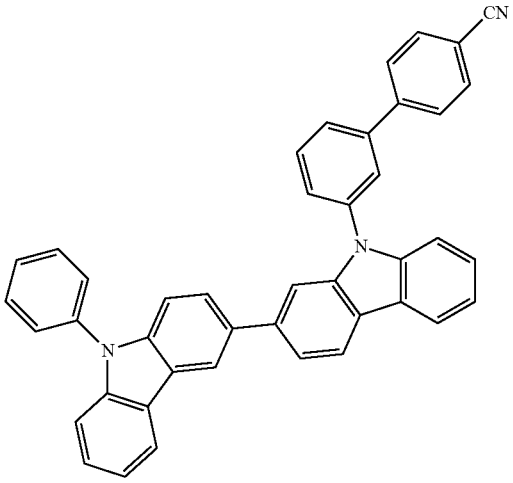

GH-1

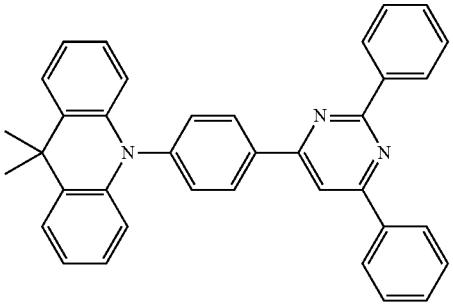

GH-2

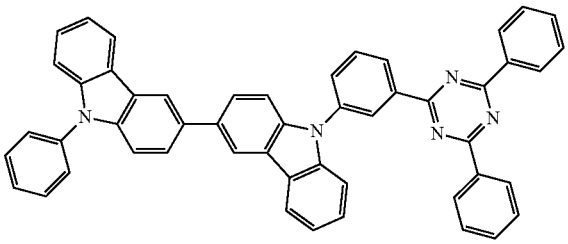

-continued

GH-3

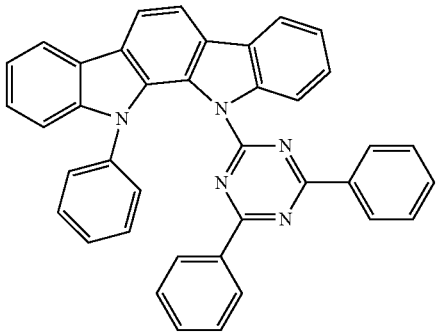

GH-4

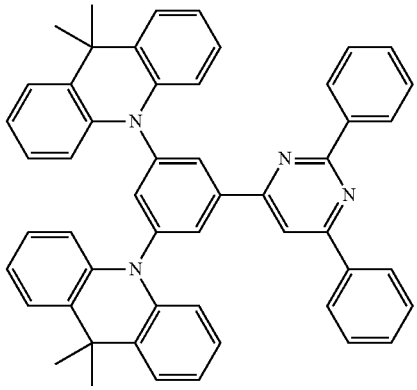

BH-1

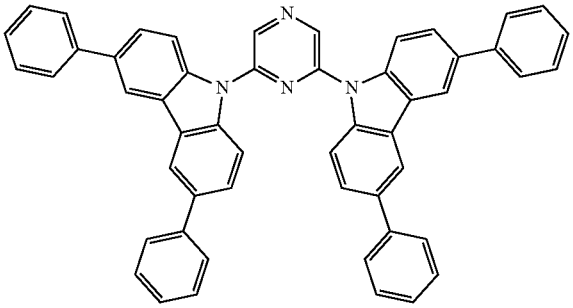

Substrate

The organic EL device according to the exemplary embodiment is formed on a light-transmissive substrate. The light-transmissive substrate supports an anode, an organic compound layer, a cathode and the like of the organic EL device. The light-transmissive substrate is preferably a smoothly-shaped substrate that transmits 50% or more of light in a visible region of 400 nm to 700 nm.

The light-transmissive plate is exemplarily a glass plate, a polymer plate or the like.

The glass plate is formed of soda-lime glass, barium/strontium-containing glass, lead glass, aluminosilicate glass, borosilicate glass, barium borosilicate glass, quartz and the like.

The polymer plate is formed of polycarbonate, acryl, polyethylene terephthalate, polyether sulfide, polysulfone and the like.

Anode and Cathode

The anode of the organic EL device injects holes into the emitting layer, so that it is efficient that the anode has a work function of 4.5 eV or higher.

Exemplary materials for the anode are indium-tin oxide (ITO), tin oxide (NESA), indium zinc oxide, gold, silver, platinum and copper.

When light from the emitting layer is to be emitted through the anode, the anode preferably transmits more than 10% of the light in the visible region. Sheet resistance of the anode is preferably several hundreds Ω per square or lower. Although depending on the material of the anode, the thickness of the anode is typically in a range of 10 nm to 1 μm, preferably in a range of 10 nm to 200 nm.

The cathode is preferably formed of a material with smaller work function in order to inject electrons into the emitting layer.

Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, and alloy of magnesium and silver.

Like the anode, the cathode may be made by forming a thin film on, for instance, the electron transporting layer and the electron injecting layer by a method such as vapor deposition. In addition, the light from the emitting layer may be emitted through the cathode. When light from the emitting layer is to be emitted through the cathode, the cathode preferably transmits more than 10% of the light in the visible region.

Sheet resistance of the cathode is preferably several hundreds Ω per square or lower.

The thickness of the cathode is typically in the range of 10 nm to 1 μm, and preferably in the range of 50 nm to 200 nm, though it depends on the material of the cathode.

Hole Injecting/Transporting Layer

The hole injection/transport layer helps injection of holes to the emitting layer and transport the holes to an emitting region. A compound having a large hole mobility and a small ionization energy is used as the hole injection/transport layer.

A material for forming the hole injection/transport layer is preferably a material of transporting the holes to the emitting layer at a lower electric field intensity. For instance, an aromatic amine compound is preferably used.

Electron Injecting/Transporting Layer

The electron injecting/transporting layer helps injection of the electrons into the emitting layer and transports the electrons to an emitting region. A compound having a large electron mobility is used as the electron injecting/transporting layer.

A preferable example of the compound used as the electron injecting/transporting layer is an aromatic heterocyclic compound having at least one heteroatom in a molecule. Particularly, a nitrogen-containing cyclic derivative is preferable. The nitrogen-containing cyclic derivative is preferably a heterocyclic compound having a nitrogen-containing six-membered or five-membered ring skeleton.

In the organic EL device in the exemplary embodiment, in addition to the above exemplary compound, any compound selected from compounds known as being used in the typical organic El device is usable as a compound for the organic compound layer other than the emitting layer.

Layer Formation Method(s)

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Thickness

The thickness of each organic layer of the organic EL device in the exemplary embodiment is subject to no limitation except for the thickness particularly described above. However, the thickness is typically preferably in a range of several nanometers to 1 μm because an excessively thin film is likely to entail defects such as a pin hole while an excessively thick film requires high applied voltage and deteriorates efficiency.

Modifications of Exemplary Embodiment(s)

It should be noted that the invention is not limited to the above exemplary embodiment but may include any modification and improvement as long as such modification and improvement are compatible with the invention.

The emitting layer is not limited to a single layer, but may be provided as laminate by a plurality of emitting layers. When the organic EL device includes the plurality of emitting layers, it is only required that at least one of the emitting layers includes the host material and the fluorescent dopant material defined in the exemplary embodiment. The others of the emitting layers may be a fluorescent emitting layer or a phosphorescent emitting layer.

When the organic EL device includes the plurality of emitting layers, the plurality of emitting layers may be adjacent to each other.

Though examples using a fluorescent dopant material in an emitting layer are exemplarily mentioned in the above exemplary embodiment(s), the fluorescent dopant material is not requisite in the exemplary embodiment(s) but a dopant material that is not a heavy metal complex may alternatively be used in the exemplary embodiment(s).

Further, the materials and treatments for practicing the invention may be altered to other arrangements and treatments as long as such other arrangements and treatments are compatible with the invention.

EXAMPLES

Examples of the invention will be described below. However, the invention is not limited by these Examples.

Used compounds are as follows.

HI-1

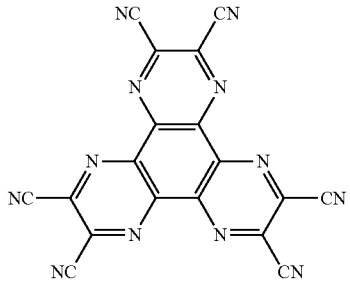

HT-1

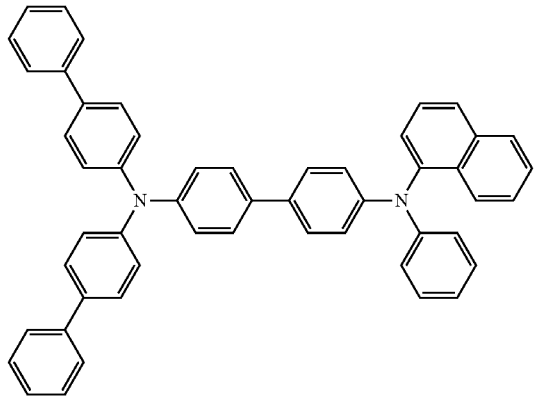

-continued
HT-2
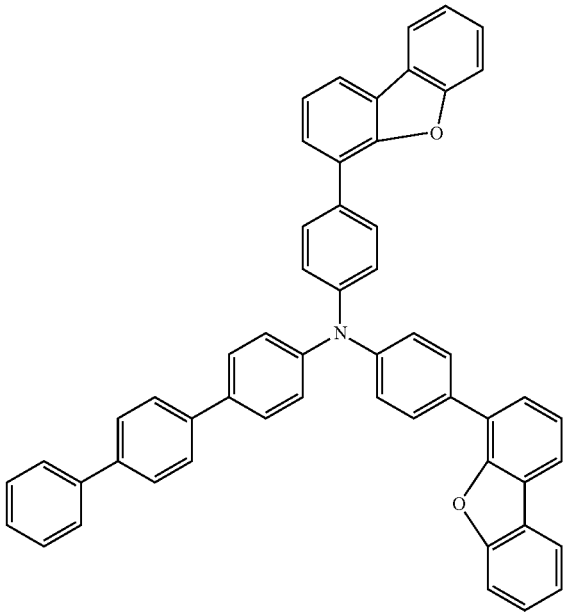
ET-1
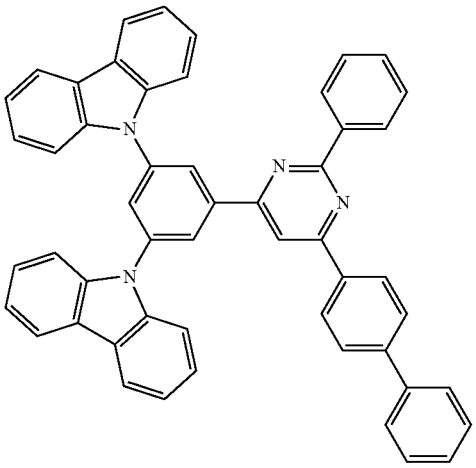
ET-2
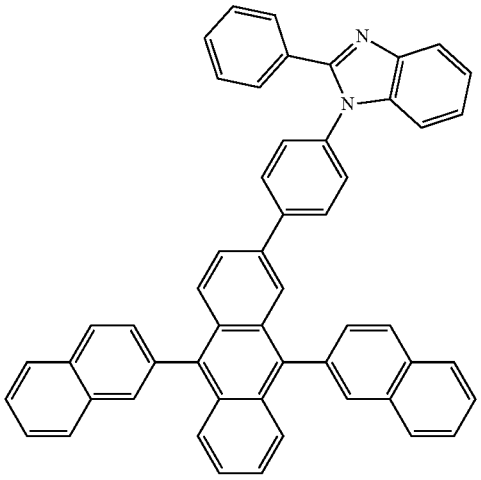
-continued
H-1
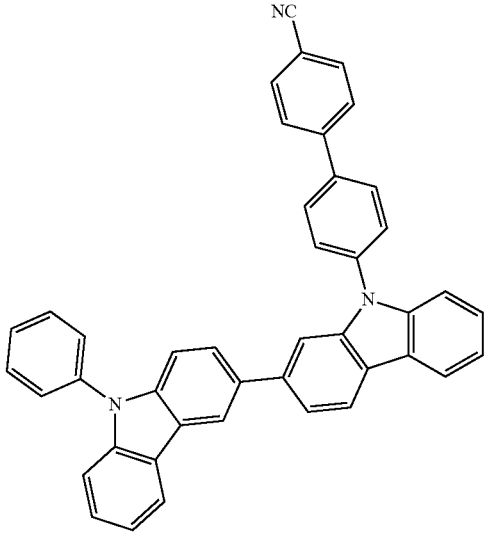
BD-1
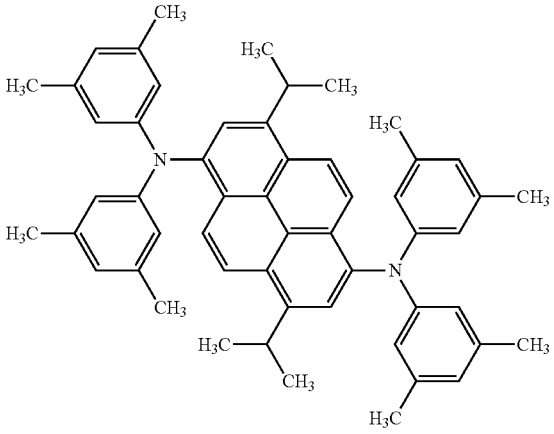
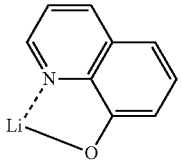
Liq
H-2
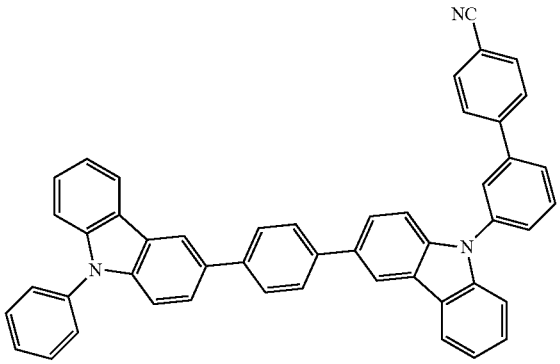

-continued
ET-3
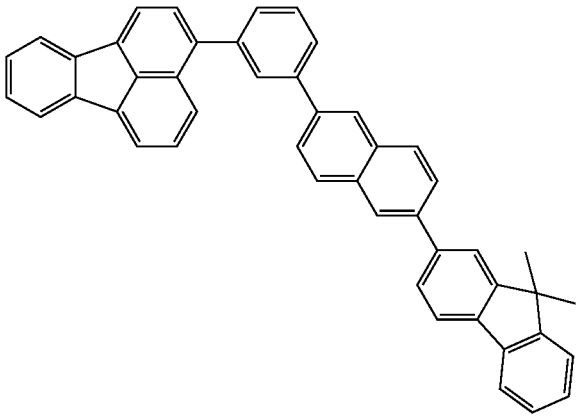
-continued
HI-2
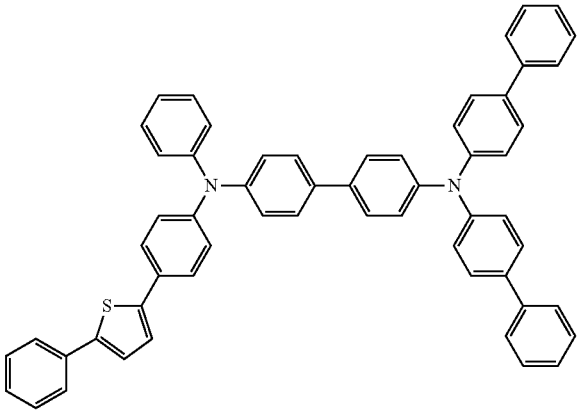
H-3
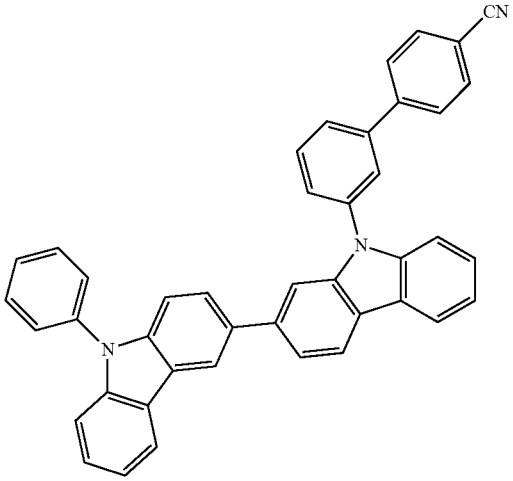
HT-2
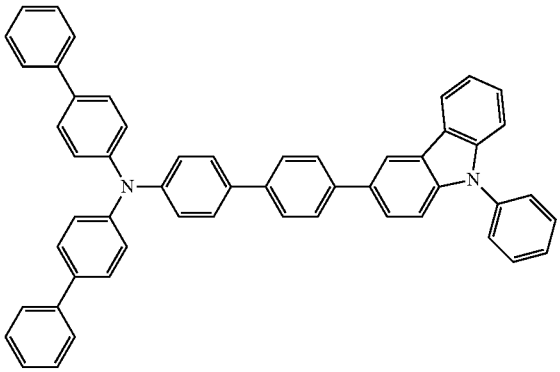
YD-1
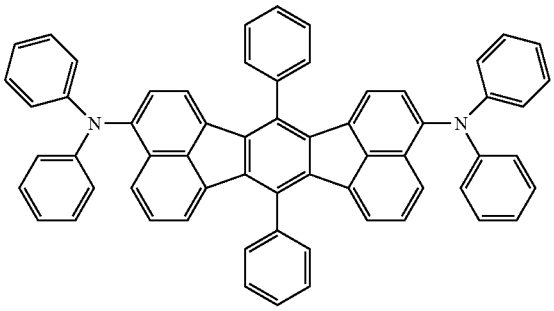
GH-4
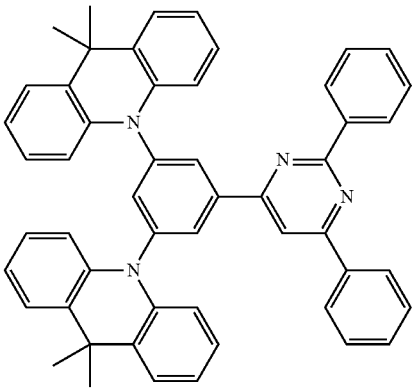

-continued

GD-1

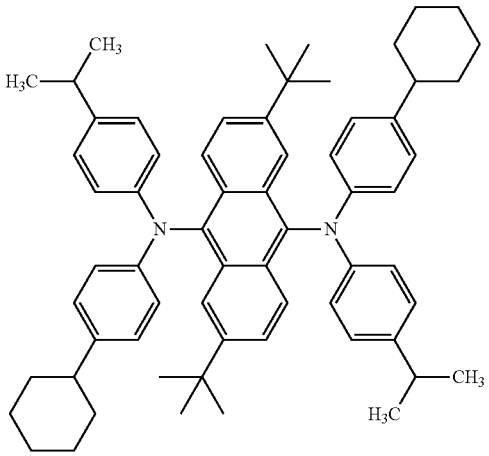

ET-4

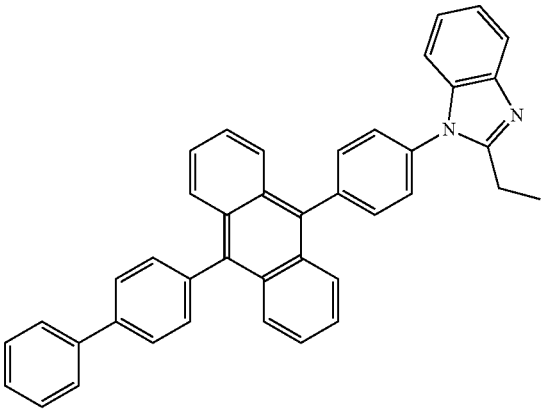

BH-1

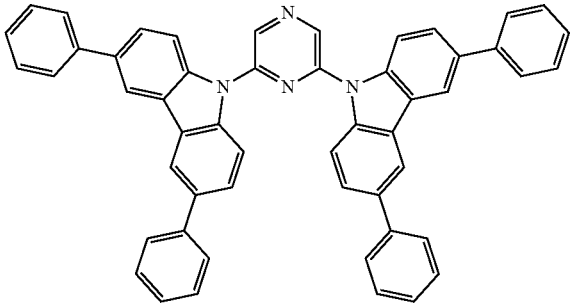

Synthesis of Compound(s)

Synthesis Example 1

Synthesis of H-1

(1-1) Synthesis of Intermediate Body 1

Under an argon gas flow, 2-nitro-1,4-dibromobenzene (11.2 g, 40 mmol), phenylboronic acid (4.9 g, 40 mmol), tetrakis(triphenylphosphine)palladium (1.39 g, 1.2 mmol), toluene (120 mL) and an aqueous solution of 2M sodium carbonate (60 mL) were added together in sequential order, and heated to reflux for 8 hours.

After the reaction solution was cooled down to the room temperature, an organic layer was separated and an organic solvent was distilled away under reduced pressure. The obtained residue was refined by silica-gel column chromatography, so that the intermediate body 1 (6.6 g, a yield of 59%) was obtained. As a result of FD-MS (Field Desorption Mass Spectrometry) analysis, the reactant was identified as the intermediate body 1.

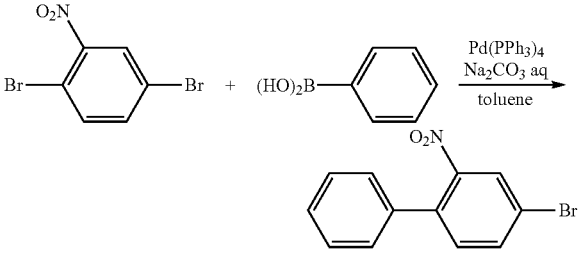

Intermediate Body 1

(1-2) Synthesis of Intermediate Body 2

Under an argon gas flow, the intermediate body 1 (6.6 g, 23.7 mmol), triphenylphosphine (15.6 g, 59.3 mmol), and o-dichlorobenzene (24 mL) were added together in sequential order, and heated to reflux at 180 degrees C. for 8 hours.

After cooled down to the room temperature, the reaction solution was refined by silica-gel column chromatography, whereby an intermediate body 2 (4 g, a yield of 68%) was obtained. As a result of FD-MS (Field Desorption Mass Spectrometry) analysis, the reactant was identified as the intermediate body 2.

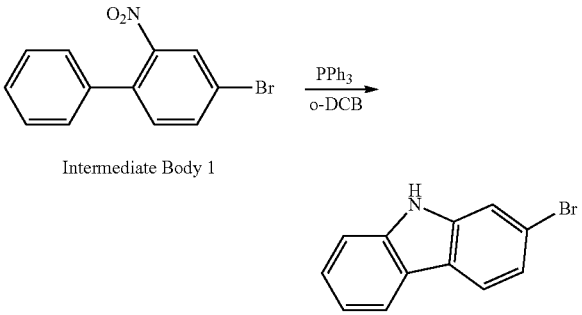

Intermediate Body 1

Intermediate Body 2

(1-3) Synthesis of Intermediate Body 3

An intermediate body 3 was synthesized according to the same method as that for the synthesis of the intermediate body 1, except for using the intermediate body 2 in place of 2-nitro-1,4-dibromobenzene and 9-phenyl-9H-carbazole-3-ylboronic acid in place of phenylboronic acid. As a result of FD-MS (Field Desorption Mass Spectrometry) analysis, the reactant was identified as the intermediate body 3.

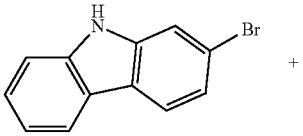

Intermediate Body 2

-continued

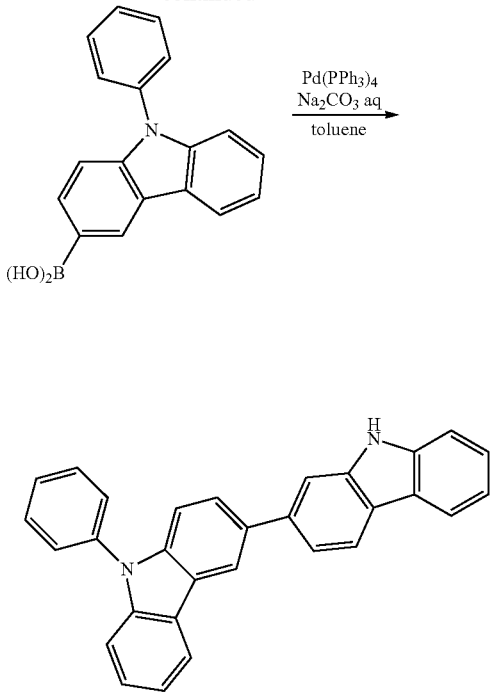

Intermediate Body 3

(1-4) Synthesis of H-1

Under argon gas flow, the intermediate body 3 (3.3 g, 8.1 mmol), 4-bromo-4'-cyanobiphenyl (2.5 g, 9.7 mmol), tris (dibenzylideneacetone)dipalladium (0.297, 0.324 mmol), tri-t-butylphosphonium tetrafluoroborate (0.234 g, 0.805 mmol), sodium t-butoxide (1.5 g, 16.2 mmol), and anhydrous xylene (40 mL) were sequentially mixed, and heated to reflux for eight hours.

After the reaction solution was cooled down to the room temperature, an organic layer was separated and an organic solvent was distilled away under reduced pressure. The obtained residue was refined by silica-gel column chromatography, whereby 2.6 g of a white solid (yield 54%) was obtained.

FD-MS (Field Desorption Mass Spectrometry), maximum ultraviolet absorption wavelength λmax and maximum fluorescence emission wavelength in a toluene solution of the obtained compound are as follows.

FDMS, calcd for C43H27N3=585. found m/z=585 (M+)

UV(PhMe); λmax, 324 nm, FL(PhMe, λex=300 nm); λmax, 393 nm

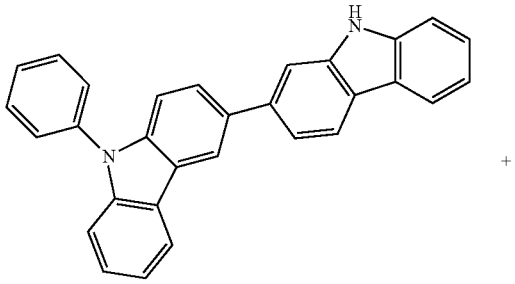

Intermediate Body 3

-continued

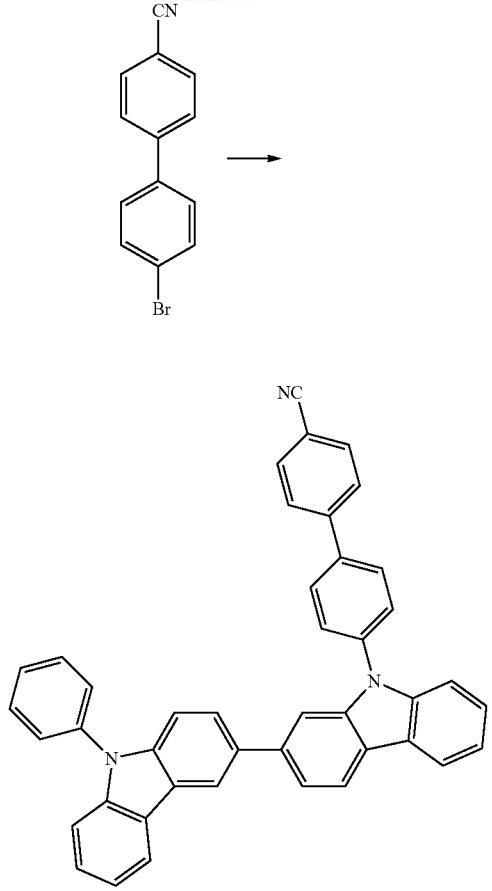

H-1

Synthesis Example 2

Synthesis of H-2

(2-1) Synthesis of Intermediate Body 4

An intermediate body 4 was synthesized according to the same method as that for the synthesis of the intermediate body 1, except for using 1-bromo-4-iodebenzene in place of 2-nitro-1,4-dibromo-1-benzene and 9-phenyl-9H-carbazole-3-ylboronic acid in place of phenylboronic acid. As a result of FD-MS (Field Desorption Mass Spectrometry) analysis, the reactant was identified as the intermediate body 4.

(2-2) Synthesis of Intermediate Body 5

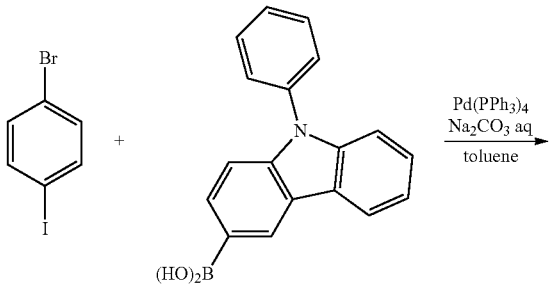

-continued

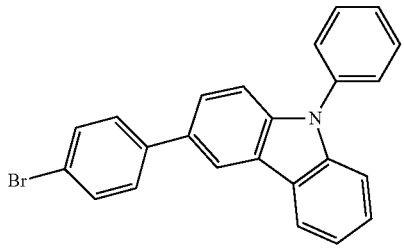

Intermediate Body 4

Under argon gas flow, the intermediate body 4 (10 g, 25 mmol), bis(pinacolato)diboron (8.3 g, 33 mmol), [1,1'-bis (diphenylphosphino)ferrocene]palladium (II) dichloride dichloromethane adduct (0.62 g, 0.75 mmol), potassium acetate (7.4 g, 75 mmol) and N,N-dimethylformamide (170 mL) were sequentially mixed, and heated to reflux for eight hours.

After the reaction solution was cooled down to the room temperature, an organic layer was separated and an organic solvent was distilled away under reduced pressure. The obtained residue was refined by silica-gel column chromatography, so that an intermediate body 5 (10 g, a yield of 91%) was obtained. As a result of FD-MS (Field Desorption Mass Spectrometry) analysis, the reactant was identified as the intermediate body 5.

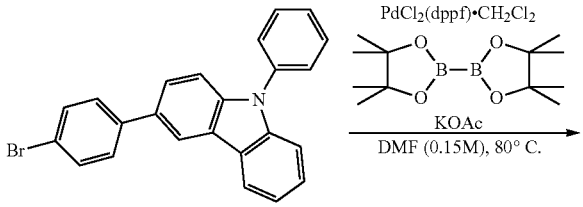

Intermediate Body 4

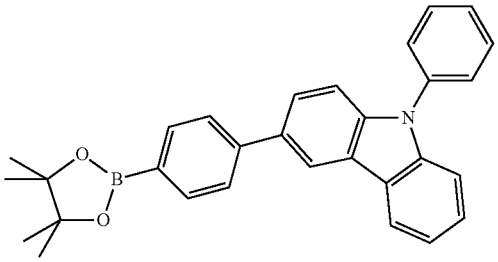

Intermediate Body 5

(2-3) Synthesis of Intermediate Body 6

An intermediate body 6 was synthesized according to the same method as that for the synthesis of the intermediate body 1, except for using 3-bromocarbazole in place of 2-nitro-1,4-dibromobenzene and the intermediate body 5 in place of phenylboronic acid. As a result of FD-MS (Field Desorption Mass Spectrometry) analysis, the reactant was identified as the intermediate body 6.

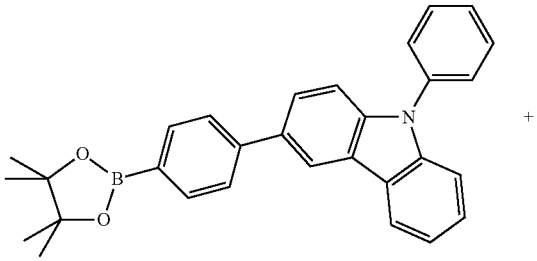

Intermediate Body 5

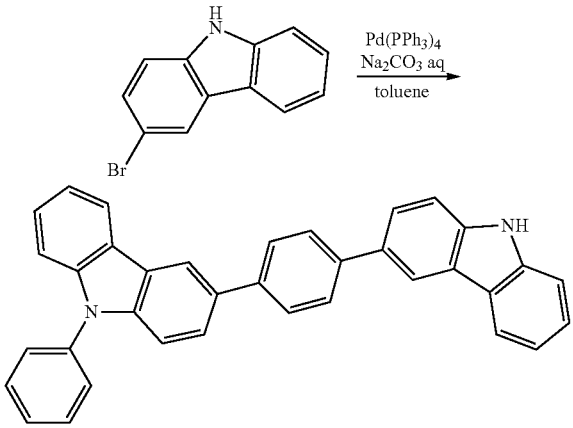

Intermediate Body 6

(2-4) Synthesis of H-2

H-2 was synthesized according to the same method as that for the synthesis of H-1, except for using 3'-bromophenyl-4-carbonitrile in place of 4-bromo-4'-cyanobiphenyl and the intermediate body 6 in place of intermediate body 3.

FD-MS (Field Desorption Mass Spectrometry) of the obtained compound is as follows.

FDMS, calcd for C49H31N3=661. found m/z=661 (M+)

UV(PhMe); λmax, not detected, FL(PhMe, λex=300 nm); λmax, 418 nm

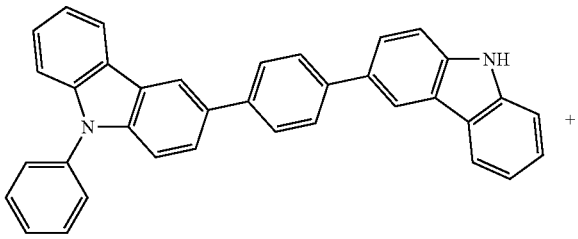

Intermediate Body 6

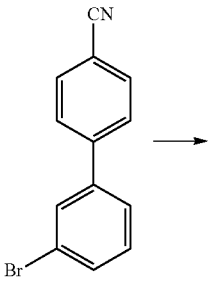

-continued

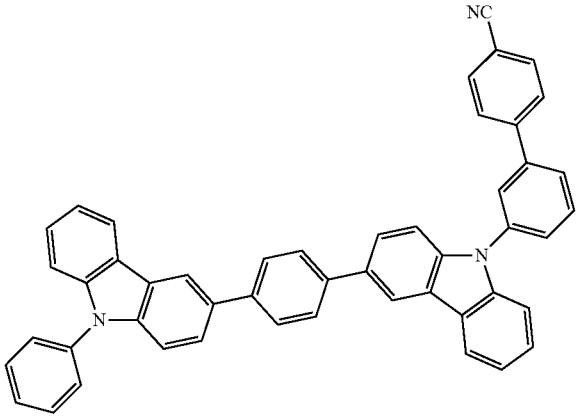

H-2

Synthesis Example 3

Synthesis of H-3

H-3 was synthesized in the same manner as H-1, except that 4'-bromobiphenyl-3-carbonitrile was used in place of 4-bromo-4'-cyanobiphenyl.

FD-MS (Field Desorption Mass Spectrometry), maximum ultraviolet absorption wavelength λmax and maximum fluorescence emission wavelength in a toluene solution of the obtained compound are as follows.

FDMS, calcd for C43H27N3=585. found m/z=585 (M+)

UV(PhMe); λmax, 322 nm, FL(PhMe, λex=300 nm); λmax, 376 nm

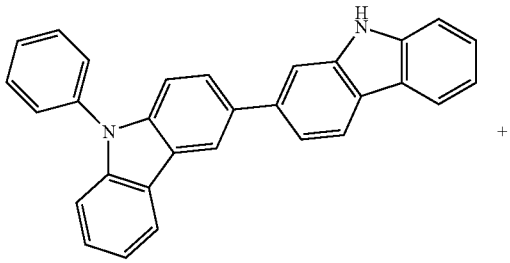

Intermediate Body 3

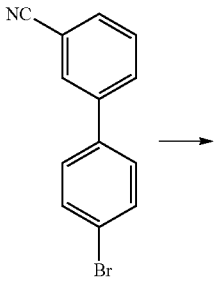

-continued

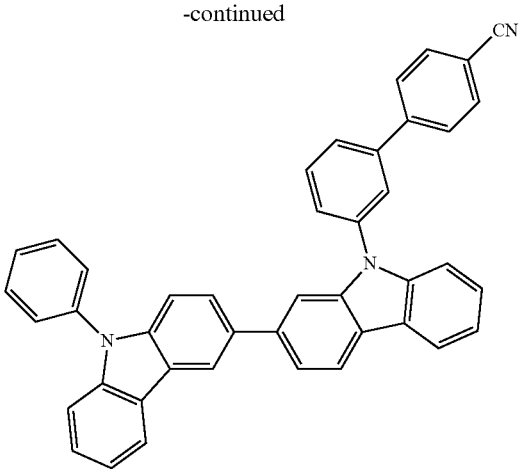

H-3

Synthesis Example 4

Synthesis of GH-4

Under an argon gas atmosphere, an intermediate A (4.4 g, 21 mmol) synthesized according to the method described in JP-A-2010-180204, an intermediate B (4.7 g, 10 mmol) synthesized according to the method described in International Publication No. WO03/080760, tris(dibenzylidene acetone)dipalladium (0.37 g, 0.4 mmol), tri-t-butylphosphonium tetrafluoroborate (0.46 g, 1.6 mmol), t-butoxysodium (2.7 g, 28 mmol) and anhydrous toluene (100 ml) were sequentially added and refluxed for eight hours.

After the reaction solution was cooled down to the room temperature, an organic layer was separated and an organic solvent was distilled away under reduced pressure. The obtained residue was refined by silica-gel column chromatography, so that a target compound GH-4 (3.6 g, a yield of 50%) was obtained.

FD-MS analysis consequently showed that m/e was equal to 722 while a calculated molecular weight was 722.

A synthesis scheme of the compound GH-4 is shown below.

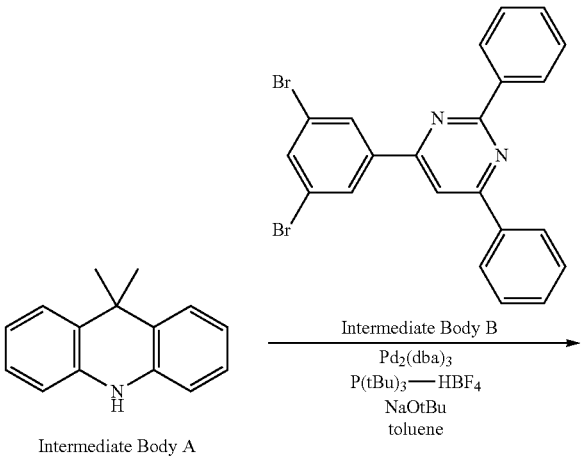

Intermediate Body A

-continued

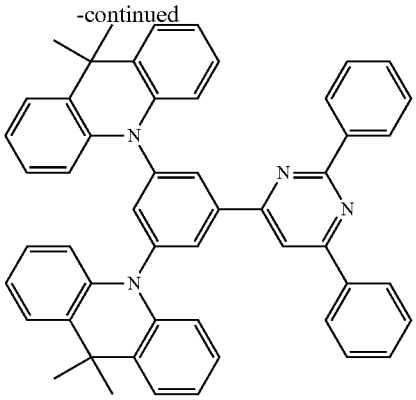

GH-4

Synthesis Example 5

Synthesis of BH-1

(5-1) Synthesis of 3,6-diphenylcarbazole

Under a nitrogen gas atmosphere, to a flask, 3,6-dibromocarbazole (5 g, 15.4 mmol), phenylboronic acid (4.1 g, 33.9 mmol), tetrakis(triphenylphosphine)palladium (0.7 g, 0.6 mmol), toluene (45 ml) and 2M sodium carbonate (45 ml) were mixed in sequence, and were stirred for eight hours at 80 degrees C. An organic phase was separated and then concentrated under reduced pressure by an evaporator. The obtained residue thereof was refined by silica-gel column chromatography, so that 3.6-diphenylcarbazole (3.6 g, a yield of 74%) was obtained.

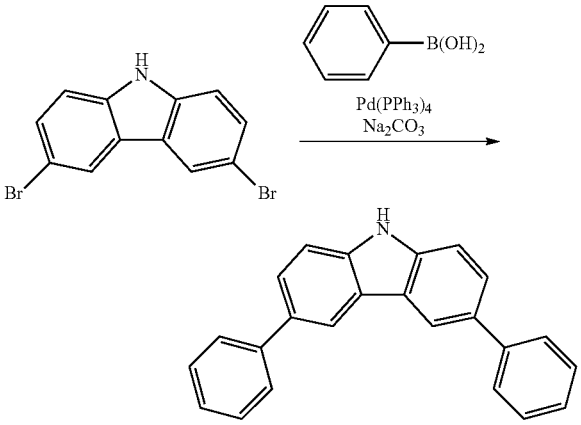

(5-2) Synthesis of BH-1

Under an argon gas atmosphere, 2,6-dichloropyrazine (0.6 g, 3.9 mmol), 3,6-dibromocarbazole (2.6 g, 8 mmol), tris(dibenzylideneacetone)dipalladium (0.07 g, 0.08 mmol), tri-t-butylphosphonium tetrafluoroborate (0.09 g, 0.3 mmol), t-butoxysodium (0.5 g, 5.5 mmol), and anhydrous toluene (20 ml) were sequentially mixed, and heated to reflux for 8 hours.

After the reaction solution was cooled down to the room temperature, an organic layer was separated and an organic solvent was distilled away under reduced pressure. The obtained residue thereof was refined by silica-gel column chromatography, so that 1.8 g of a solid was obtained.

FD-MS analysis consequently showed that the obtained compound was identified as a compound BH-1.

FD-MS:

calcd for $C_{52}H_{34}N_4$=714. found m/z=714(M+, 100)

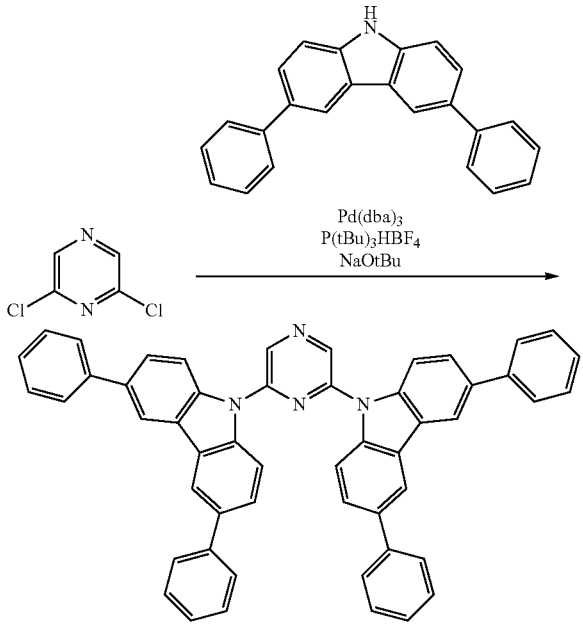

BH-1

Evaluation of Compounds

Next, properties of the compounds used in Example were measured. The target compounds are H-1 to H-3. A measurement method or a calculation method is described below. Measurement results or calculation results are shown in Table 1.

(1) Singlet Energy EgS

Singlet Energy EgS was obtained by the following method.

A target compound to be measured was deposited on a quartz substrate to prepare a sample. An absorption spectrum of the sample was measured at a normal temperature (300K). A sample was 100 nm thick. The absorption spectrum was expressed in coordinates of which ordinate axis indicated absorbance and of which abscissa axis indicated the wavelength. A tangent was drawn to the fall of the absorption spectrum on the long-wavelength side, and a wavelength value λedge (nm) at an intersection of the tangent and the abscissa axis was obtained. The wavelength value was converted to an energy value by the following conversion equation. The energy value was defined as EgS.

The conversion equation: EgS (eV)=1239.85/λedge

For the measurement of the absorption spectrum, a spectrophotometer (U3310 manufactured by Hitachi, Ltd.) was used.

The tangent to the fall of the absorption spectrum on the long-wavelength side was drawn as follows. While moving on a curve of the absorption spectrum from the maximum spectral value closest to the long-wavelength side in a long-wavelength direction, a tangent at each point on the curve is checked. An inclination of the tangent is decreased and increased in a repeated manner as the curve falls (i.e., a value of the ordinate axis is decreased). A tangent drawn at a point of the minimum inclination closest to the long-wavelength side (except when absorbance is 0.1 or less) is defined as the tangent to the fall of the absorption spectrum on the long-wavelength side.

The maximum absorbance of 0.2 or less was not included in the above-mentioned maximum absorbance on the long-wavelength side.

(2) Energy Gap $Eg_{77K}$ and Triplet Energy $EgT_D$ $Eg_{77K}$ and $EgT_D$ were obtained by the following method.

Each of the compounds was measured by a known method of measuring phosphorescence (e.g. a method described in "Hikarikagaku no Sekai (The World of Photochemistry)" (edited by The Chemical Society of Japan, 1993, on and near page 50). Specifically, each of the compounds was dissolved in a solvent (sample: 10 μmol/L, EPA (diethylether:isopentane:ethanol=[5:5:5] *5:5:2* in volume ratio, each solvent in a spectroscopic grade), thereby forming a sample for phosphorescence measurement. The sample for phosphorescence measurement was put into a quartz cell, cooled to 77(K) and irradiated with excitation light, so that phosphorescence intensity was measured while changing a wavelength. The phosphorescence spectrum was expressed in coordinates of which ordinate axis indicated phosphorescence intensity and of which abscissa axis indicated the wavelength.

A tangent was drawn to the rise of the phosphorescent spectrum on the short-wavelength side, and a wavelength value λedge (nm) at an intersection of the tangent and the abscissa axis was obtained. The wavelength value was converted to an energy value by the following conversion equation. The energy value was defined as $Eg_{77K}$(H) or $EgT_D$ ($Eg_{77K}$(D)).

The conversion equation:

$$Eg_{77K}(H)\ (eV)=1239.85/\lambda edge$$

$$:EgT_D\ [eV]=1239.85/\lambda edge$$

The tangent to the rise of the phosphorescence spectrum on the short-wavelength side was drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination was defined as the tangent to the rise of the phosphorescence spectrum on the short-wavelength side.

The maximum with peak intensity being 10% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

For phosphorescence measurement, a spectrophotofluorometer body F-4500 and optional accessories for low temperature measurement (which were manufactured by Hitachi High-Technologies Corporation) were used. The measurement instrument is not limited to this arrangement. A combination of a cooling unit, a low temperature container, an excitation light source and a light-receiving unit may be used for measurement.

(3) ΔST

ΔST was obtained as a difference between EgS and $Eg_{77K}$ measured in the above (1) and (2) (see the above numerical formula (2)). The results are shown in Table 1.

A half bandwidth of photoluminescence spectrum was obtained as follows.

Each of the compounds was formed in a 100 nm-thick film on a glass substrate with a deposition apparatus to prepare a sample for fluorescence measurement.

The sample for phosphorescence measurement was irradiated with excitation light at a room temperature 300(K), so that fluorescence intensity was measured while changing a wavelength.

The photoluminescence spectrum was expressed in coordinates of which ordinate axis indicated fluorescence intensity and of which abscissa axis indicated the wavelength. For fluorescence measurement, a spectrophotofluorometer F-4500 (manufactured by Hitachi High-Technologies Corporation) was used.

The half bandwidth (unit: nm) was measured based on the photoluminescence spectrum.

The compounds H-1, H-2 and H-3 were measured with respect to the half bandwidth. The results are shown in Table 1.

TABLE 1

| Host Material | EgS (Thin Film) [eV] | Eg (77K) [eV] | ΔST [eV] | Half Bandwidth [nm] |
|---|---|---|---|---|
| H-1 | 3.02 | 2.73 | 0.29 | 57 |
| H-2 | 2.99 | 2.71 | 0.28 | 67 |
| H-3 | 3.02 | 2.74 | 0.28 | 62 |
| GH-4 | 2.98 | 2.91 | 0.07 | — |
| GD-1 | 2.47 | 1.80 | 0.67 | — |
| BH-1 | 2.90 | 2.84 | 0.06 | — |
| BD-1 | 2.69 | — | — | — |

Figure 9:
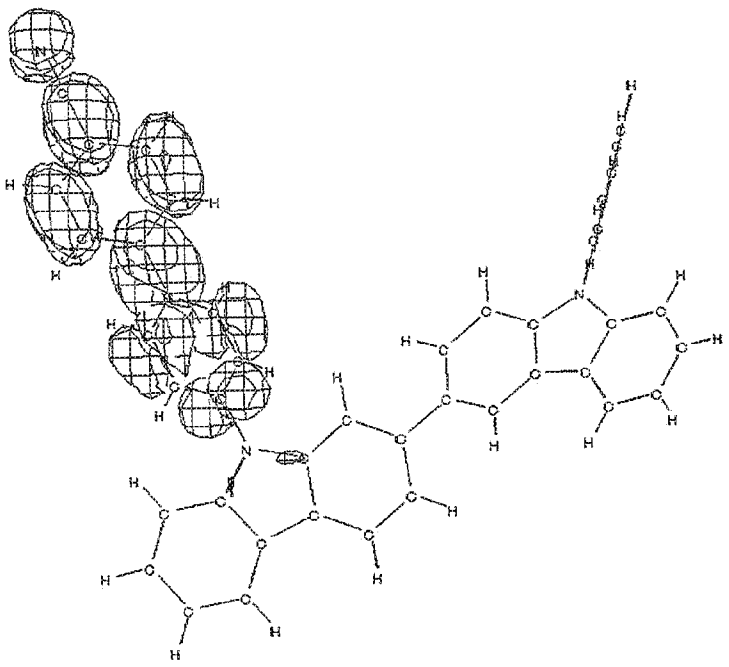
FIG. 9 is a molecular orbital view of the host material according to the exemplary embodiment of the invention.
Figure 9:
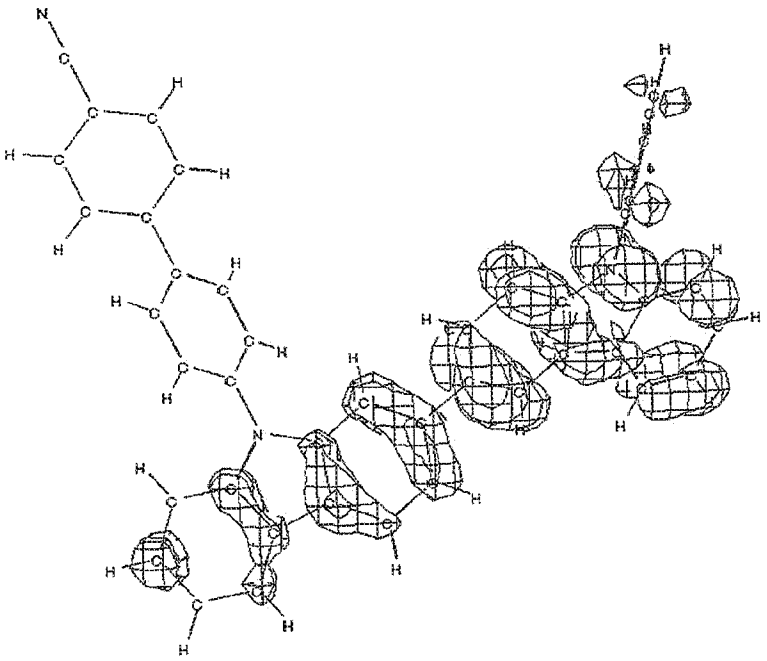
Figure 10:
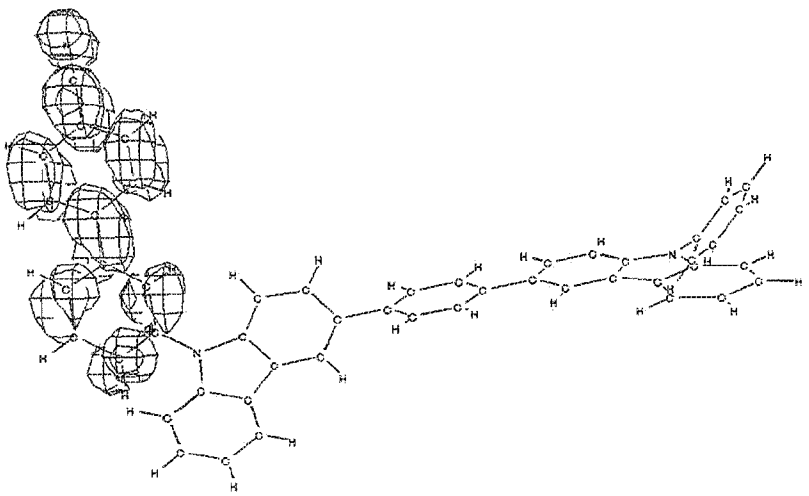
FIG. 10 is another molecular orbital view of the host material according to the exemplary embodiment of the invention.
Figure 10:
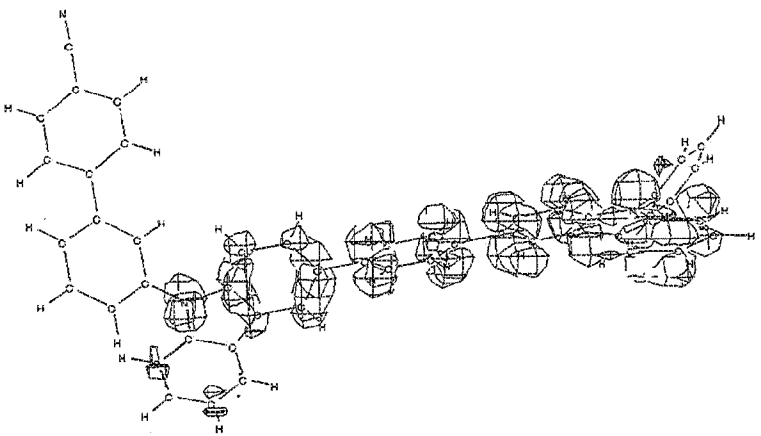
Figure 11:
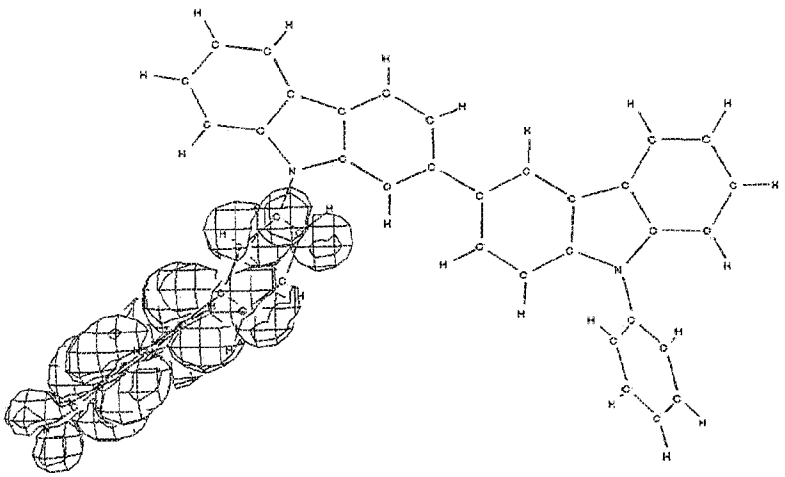
FIG. 11 is still another molecular orbital view of the host material according to the exemplary embodiment of the invention.
Figure 11:
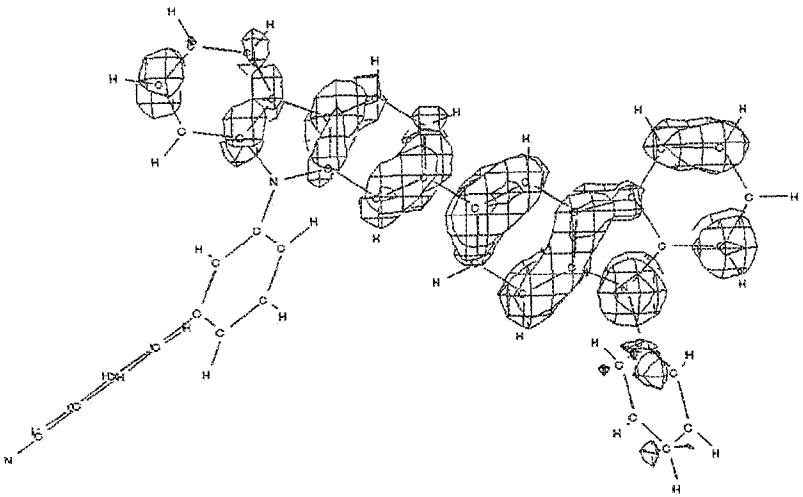

Molecular orbital views of the compounds H-1 to H-3 are respectively shown in FIGS. 9 to 11. Preparation and Evaluation of Organic EL Device The organic EL devices were prepared in the following manner and evaluated.

Example 1

A glass substrate (size: 25 mm×75 min×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 77 nm thick.

After the glass substrate having the transparent electrode line was cleaned, the glass substrate was mounted on a substrate holder of a vacuum evaporation apparatus. Initially, a compound HI-1 was deposited on a surface of the glass substrate where the transparent electrode line was provided in a manner to cover the transparent electrode, thereby forming a 5-nm thick film of the compound HI-1. The HI-1 film serves as a hole injecting layer.

After the film formation of the HI-1 film, a compound HT-1 was deposited on the HI-1 film to form a 125-nm thick HT-1 film. The HT-1 film serves as a first hole transporting layer.

A compound HT-2 was deposited on the HT-1 film to form a 25-nm thick HT-2 film. The HT-2 film serves as a second hole transporting layer.

A compound H-1 (a host material) and a compound BD-1 (a fluorescent dopant material) were co-deposited on the HT-2 film to form a 25-nm thick emitting layer. The concentration of the dopant material was set at 4 mass %.

An electron transporting compound ETA was deposited on the emitting layer to form a 5-nm thick hole blocking layer.

Further, the compound ET-2 and Liq were co-deposited on the ET-1 film to form a 20-nm thick electron transporting layer. The concentration of Liq was set at 50 mass %.

Liq was deposited on the electron transporting layer to form a 1-nm thick Liq film.

A metal Al was deposited on the Liq film to form an 80-nm thick metal cathode.

A device arrangement of the organic EL device in Example 1 is schematically shown as follows.

ITO(77)/HI-1(5)/HT-1(125)/HT-2(25)/H-1:BD-1(25,4%)/ET-1(5)/ET-2:Liq(20,50%)/Liq(1)/Al(80)

Numerals in parentheses represent a film thickness (unit: nm). Numerals represented by percentage in the same parentheses represent a ratio (mass %) of an added component such as the fluorescent dopant material in the emitting layer.

Example 2

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 77 nm thick.

After the glass substrate having the transparent electrode line was cleaned, the glass substrate was mounted on a substrate holder of a vacuum evaporation apparatus. Initially, a compound HI-1 was deposited on a surface of the glass substrate where the transparent electrode line was provided in a manner to cover the transparent electrode, thereby forming a 5-nm thick film of the compound HI-1. The HI-1 film serves as a hole injecting layer.

After the film formation of the HI-1 film, a compound HT-1 was deposited on the HI-1 film to form a 65-nm thick HT-1 film. After the film formation of the HT-1 film, a compound HT-2 was deposited on the HT-1 film to form a 10-nm thick HT-2 film on the HT-1 film. The HT-1 film and the HT-2 film serve as a hole transporting layer.

A compound H-2 (a host material) and a compound YD-1 (a fluorescent dopant material) were co-deposited on the HT-2 film to form a 25-nm thick emitting layer. The concentration of the dopant material was set at 4 mass %.

An electron transporting compound ET-3 was deposited on the emitting layer to form a 5-nm thick hole blocking layer.

ET-2 was deposited on the hole blocking layer to form a 30-nm thick electron transporting layer.

Liq was deposited on the electron transporting layer to form a 1-nm thick LiF film.

A metal Al was deposited on the Liq film to form an 80-nm thick metal cathode.

A device arrangement of the organic EL device in Example 2 is schematically shown as follows.

ITO(77)/HI-1(5)/HT-1(65)/HT-2(10)/H-2:YD-1(25,4%)/ET-3(5)/ET-2(30)/LiF(1)/Al(80)

Numerals in parentheses represent a film thickness (unit: nm). The numerals represented by percentage in parentheses indicate a ratio (mass %) of YD-1.

Example 3

An organic EL device was manufactured in the same manner as Example 2 except that the compound H-3 was used as the host material in place of the compound H-2.

Example 4

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having the transparent electrode line was cleaned, the glass substrate was mounted on a substrate holder of a vacuum evaporation apparatus. Initially, a compound HI-2 was deposited on a surface of the glass substrate where the transparent electrode line was provided in a manner to cover the transparent electrode, thereby forming a 50-nm thick film of the compound HI-2. The HI-2 film serves as a hole injecting layer.

After the film formation of the HI-2 film, a compound HT-2 was deposited on the HI-2 film to form a 60-nm thick HT-2 film. The HT-2 film serves as a hole transporting layer.

The compound GH-4 (a host material) and the compound GD-1 (a fluorescent dopant material) were co-deposited on the HT-2 film to form a 30-nm thick emitting layer. The concentration of the dopant material was set at 5 mass %.

An electron transporting compound ET-4 was deposited on the emitting layer to form a 25-nm thick electron transporting layer.

LiF was deposited on the electron transporting layer to form a 1-nm thick LiF film.

A metal Al was deposited on the LiF film to form an 80-nm thick metal cathode.

Thus, the organic EL device of Example 4 was manufactured.

A device arrangement of the organic EL device in Example 4 is schematically shown as follows.

ITO(130)/HI-2(50)/HT-2(60)/GH-4:GD-1(30,5%)/ET-4(25)/LiF(1)/Al(80)

Example 5

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 70 nm thick.

After the glass substrate having the transparent electrode line was cleaned, the glass substrate was mounted on a substrate holder of a vacuum evaporation apparatus. Initially, a compound HI-1 was deposited on a surface of the glass substrate where the transparent electrode line was provided in a manner to cover the transparent electrode, thereby forming a 5-nm thick film of the compound HI-1. The HI-1 film serves as a hole injecting layer.

After the film formation of the HI-1 film, a compound HT-1 was deposited on the HI-1 film to form a 125-nm thick HT-1 film. After the film formation of the HT-1 film, a compound HT-2 was deposited on the HT-1 film to form a 25-nm thick HT-2 film on the HT-1 film. The HT-1 film and the HT-2 film serve as a hole transporting layer.

A compound BH-1 (a host material) and a compound BD-1 (a fluorescent dopant material) were co-deposited on the HT-2 film to form a 25-nm thick emitting layer. The concentration of the dopant material was set at 4 mass %.

An electron transporting compound ET-1 was deposited on the emitting layer to form a 5-nm thick hole blocking layer.

ET-2 and Liq were co-deposited on the hole blocking layer to form a 20-nm thick electron transporting layer. A concentration ratio between ET-2 and Liq was set at 50 mass %:50 mass %.

Liq was deposited on the electron transporting layer to form a 1-nm thick Liq film.

A metal Al was deposited on the Liq film to form an 80-nm thick metal cathode.

Thus, the organic EL device of Example 5 was manufactured.

A device arrangement of the organic EL device in Example 5 is schematically shown as follows.

ITO(70)/HI-1(5)/HT-1(125)/HT-2(25)/BH-1:BD-1(25, 4%)/ET-1(5)/ET-2:Liq(20,50%)/Liq(1)/Al(80)

Evaluation of Organic EL Devices

The manufactured organic EL devices were evaluated in terms of drive voltage, luminous intensity, CIE1931 chromaticity, current efficiency L/J, power efficiency primary peak wavelength $\lambda_p$ and external quantum efficiency EQE. The current density was set at 1.00 mA/cm$^2$ or 10.00 mA/cm$^2$. The results are shown in Table 2.

The manufactured organic EL devices were evaluated in terms of delayed fluorescence ratio and residual strength ratio supposing that the current density was 1.00 mA/cm$^2$. The details are shown below.

Drive Voltage

Voltage was applied between ITO and Al such that the current density was 1.00 mA/cm$^2$ or 10.00 mA/cm$^2$, where the voltage (unit: V) was measured.

CIE1931 Chromaticity

Voltage was applied on each of the organic EL devices such that the current density was 1.00 mA/cm$^2$ or 10.00 mA/cm$^2$, where CIE1931 chromaticity coordinates (x, y) were measured using a spectroradiometer CS-1000 (manufactured by Konica Minolta Holdings, Inc.).

Current Efficiency L/J and Power Efficiency η

Voltage was applied on each of the organic EL devices such that the current density was 1.00 mA/cm$^2$ or 10.00 mA/cm$^2$, where spectral radiance spectra were measured by the aforementioned spectroradiometer. Based on the obtained spectral radiance spectra, the current efficiency (unit: cd/A) and the power efficiency η (unit: lm/W) were calculated.

Main Peak Wavelength $\lambda_p$

A main peak wavelength $\lambda_p$ was calculated based on the obtained spectral-radiance spectra.

External Quantum Efficiency EQE

The external quantum efficiency EQE (unit: %) was calculated based on the obtained spectral-radiance spectra, assuming that the spectra was provided under a Lambertian radiation.

Delayed Fluorescence Ratio

Voltage pulse waveform (pulse width: 500 micro second, frequency: 20 Hz, voltage: equivalent to 0.1 to 100 mA/cm$^2$) output from a pulse generator (8114A: manufactured by Agilent Technologies) was applied. EL emission was input in a photomultiplier (R928: manufactured by Hamamatsu Photonics K.K.). The pulse voltage waveform and the EL emission were synchronized and loaded in an oscilloscope (2440: Tektronix) to obtain a transitional EL waveform. Reciprocal numbers of square root of luminous intensity were plotted, which were fitted in a linear line using a value before the elapse of $10^{-5}$ seconds calculated by the method of least squares to determine a delayed fluorescence ratio.

Figure 12:
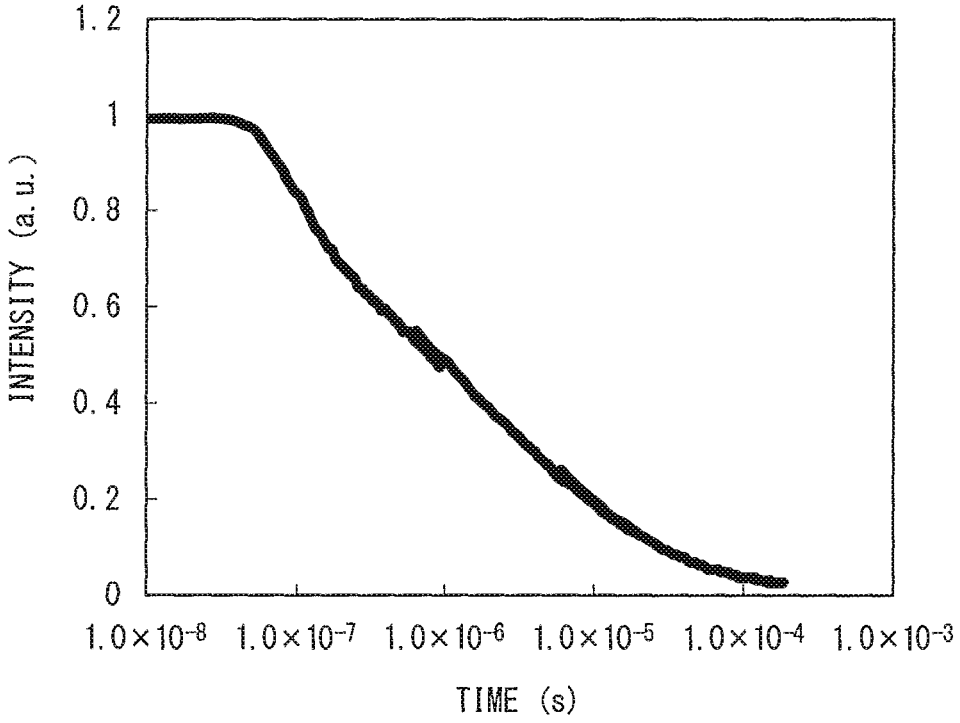
FIG. 12 is a graph showing time-varying luminous intensities of the organic EL device according to the exemplary embodiment of the invention.

The transitional EL waveform where voltage of 1.00 mA/cm$^2$ was applied on the organic EL device of the Example 1 at the room temperature is shown in FIG. 12. The pulse voltage was removed at the time of about $3\times10^{-8}$ seconds.

Based on the graph, where the voltage removal time was a starting point and the reciprocal numbers of the square root of luminous intensity before the elapse of $1.5\times10^{-5}$ seconds after voltage removal were plotted, the delayed fluorescence ratio of the organic EL device of the Example 1 was 45.9%. This delayed fluorescence ratio exceeded the theoretical upper-limit (37.5%) of the TTF ratio.

It was read from the graph in FIG. 12 that a residual strength ratio in 1 μs was 46.2%.

Figure 13:
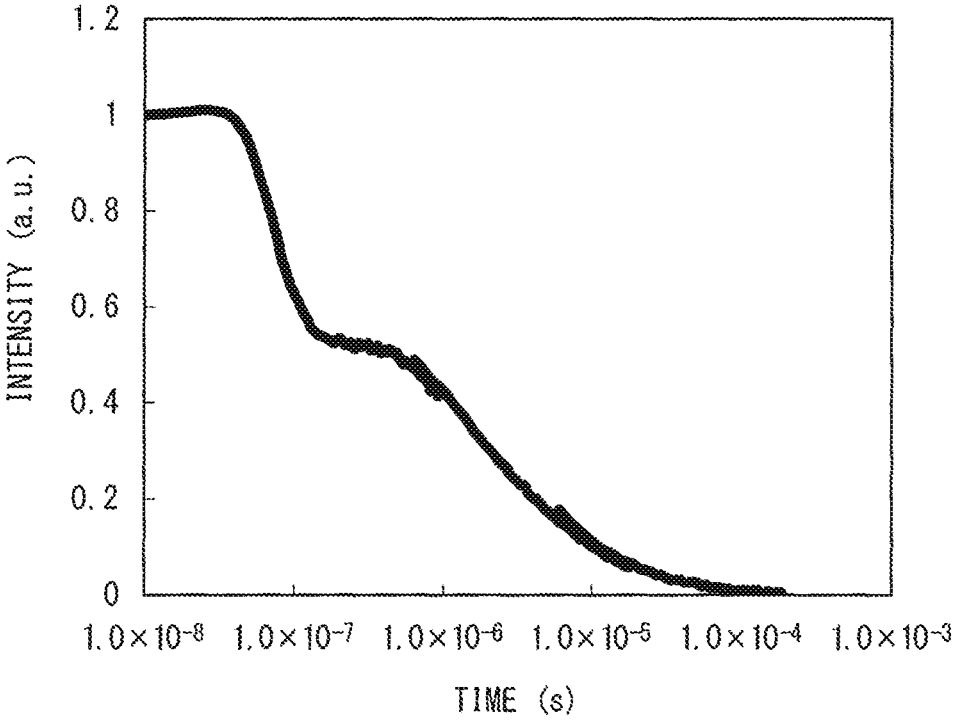
FIG. 13 is another graph showing time-varying luminous intensities of the organic EL device according to the exemplary embodiment of the invention.
Figure 14:
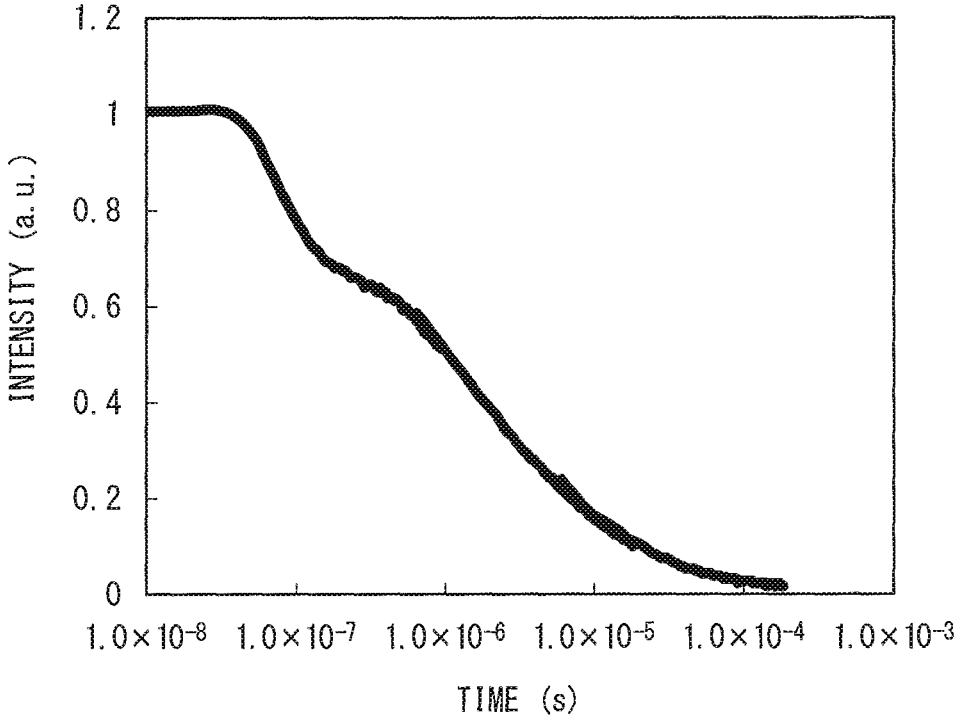
FIG. 14 is still another graph showing time-varying luminous intensities of the organic EL device according to the exemplary embodiment of the invention.
Figure 15:
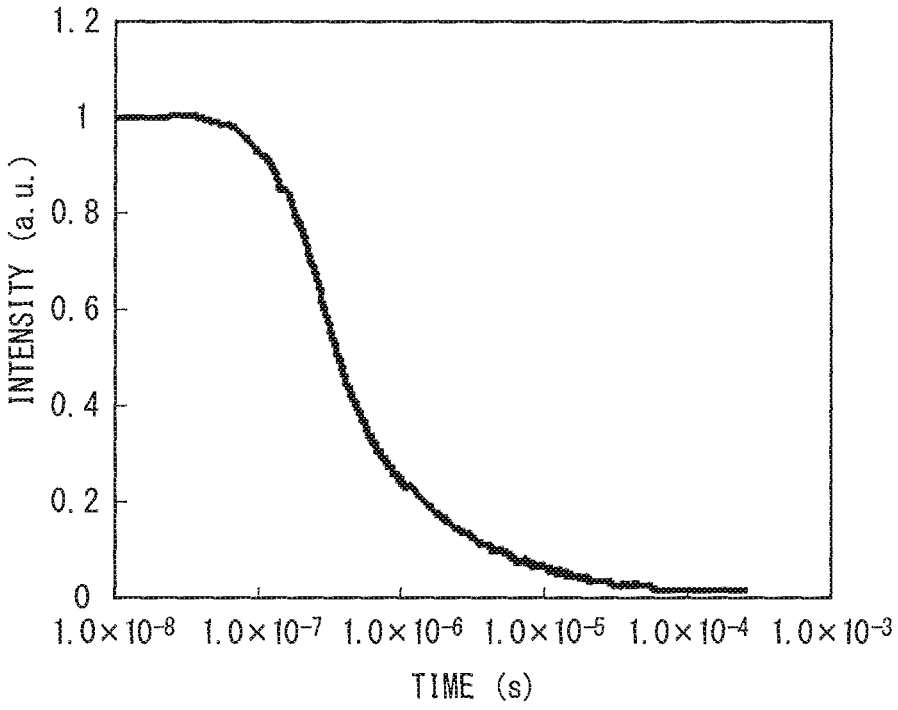
FIG. 15 is a further graph showing time-varying luminous intensities of the organic EL device according to the exemplary embodiment of the invention.

For the organic EL devices according to the Examples 2 to 5, transitional EL waveforms were obtained in the same manner as in Example 1. Specifically, reciprocal numbers of square root of the luminous intensity were plotted and were fitted in a linear line using a value before the elapse of $10^{-5}$ seconds calculated by the method of least squares, which were analyzed to determine a delayed fluorescence ratio, thereby obtaining residual strength ratio in 1 μs. The transitional EL waveforms of the organic EL devices in the Examples 2, 3 and 5 are respectively shown in FIGS. 13 to 15. The transitional EL waveform of the organic EL device in the Example 4 is shown in FIG. 6A.

The delayed fluorescence ratio and residual strength ratio of the organic EL devices in the Examples 1 to 5 are shown in Table 3.

TABLE 2

| | Host Material | Current Density [mA/cm$^2$] | Voltage [V] | Luminance [cd/m$^2$] | L/J [cd/A] | η [lm/W] | Chromaticity x | Chromaticity y | λp [nm] | EQE [%] |
|---|---|---|---|---|---|---|---|---|---|---|
| Ex. 1 | H-1 | 1.00 | 3.80 | 67.6 | 6.76 | 5.59 | 0.128 | 0.214 | 473 | 4.67 |
| Ex. 2 | H-2 | 1.00 | 3.52 | 147.2 | 14.72 | 13.12 | 0.497 | 0.481 | 572 | 4.94 |
| Ex. 3 | H-3 | 1.00 | 3.30 | 122.0 | 12.20 | 11.60 | 0.506 | 0.482 | 572 | 4.11 |
| Ex. 4 | *GH-4* | 10.00 | 3.97 | 1585.2 | 15.85 | 12.85 | 0.274 | 0.606 | 520 | 4.59 |
| | [GH-1] | 1.00 | 3.44 | 174.0 | 17.40 | 15.89 | 0.276 | 0.604 | 522 | 5.04 |
| Ex. 5 | BH-1 | 1.00 | 3.81 | 57.6 | 5.76 | 4.75 | 0.130 | 0.197 | 471 | 4.16 |

TABLE 3

| | Delayed Fluorescence Ratio [%] | Residual Strength Ratio [%] |
|---|---|---|
| Ex. 1 | 45.9 | 46.2 |
| Ex. 2 | 47.5 | 41.2 |
| Ex. 3 | 54.1 | 50.1 |
| Ex. 4 | 41.0 | 39.8 |
| Ex. 5 | 38.7 | 36.3 |

Reference Example

Herein, the organic EL device described in Literature 3 are shown as a reference example and compared with the organic EL device of Example 1 in terms of the device arrangement.

A device arrangement of the organic EL devices in the reference example is schematically shown below in the same manner as in Example 1.

ITO(110)/NPD(40)/m-CP(10)/m-CP:PIC-TRZ(20,6%)/BP4 mPy(40)/LiF(0.8)/Al(70)

Compounds used in the reference example will be shown below.

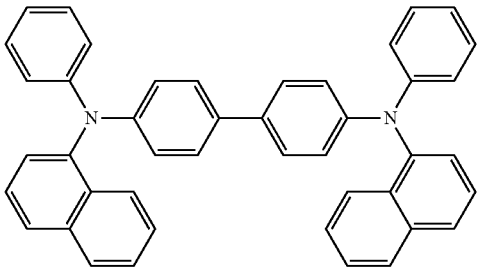

α-NPD

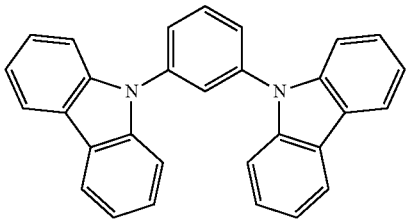

m-CP

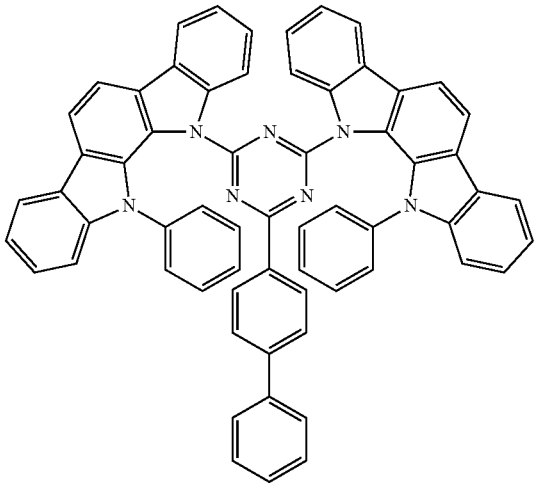

PIC-TRZ

-continued

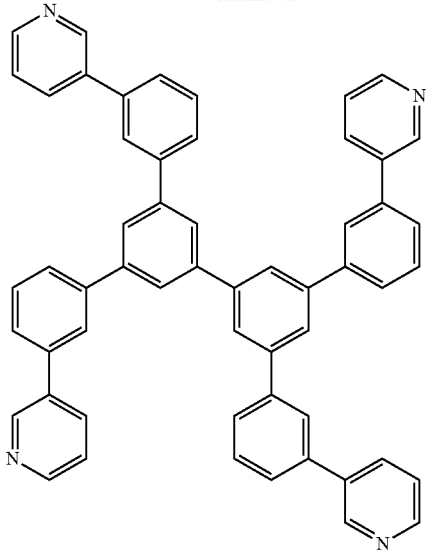

BP4mPy

The device only exhibits the maximum EQE of 5.1% in the current density area of 0.01 mA/cm$^2$ which is much lower than the current density area in a practical use. Accordingly, in a high current density area around 1 mA/cm$^2$, roll-off is generated and a luminous efficiency is reduced.

Accordingly, it is recognized that the organic EL devices of Examples 1 to 5 emitted light with a high efficiency even in the high current density area.

What is claimed is:

[1. An organic electroluminescence device comprising:

a cathode;

an anode; and an organic thin-film layer disposed between the cathode and the anode, the organic thin-film layer having one or more layers comprising an emitting layer, the emitting layer comprising a first material represented by a formula (1) below and a second material in a form of a fluorescent dopant material, $$(B)_b-L-(A)_a \tag{1}$$

where, in the formula (1):

A is a group having a partial structure selected from formulae (a-1) to (a-7) below;

B is a group having a partial structure selected from formulae (b-1) to (b-6) below;

L represents a single bond or a linking group;

the linking group is:

a substituted or unsubstituted aryl group having 6 to 30 ring carbon atoms;

a substituted or unsubstituted heterocyclic group having 5 to 30 ring atoms; or a group derived from a group formed by mutually bonding two to five of the substituted or unsubstituted aryl group having 6 to 30 ring carbon atoms and/or the substituted or unsubstituted heterocyclic group having 5 to 30 ring atoms, the mutually bonded groups being the same or different;

a is an integer in a range from 1 to 5 representing the number of a substituent(s) of A directly bonded to L; a plurality of A being mutually the same or different when a is 2 or more, b is an integer in a range from 1 to 5 representing the number of a substituent(s) of B directly bonded to L, a plurality of B being mutually the same or different when b is 2 or more;

(a-1)

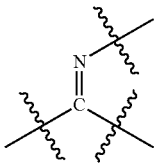

(a-2)

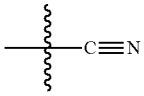

(a-3)

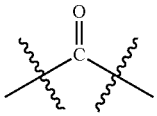

(a-4)

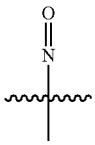

(a-5)

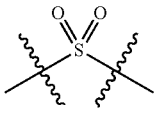

(a-6)

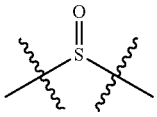

(a-7)

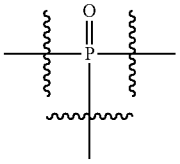

(b-1)

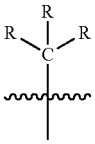

(b-2)

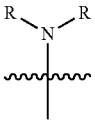

(b-3)

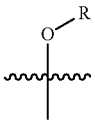

(b-4)

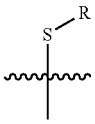

(b-5)

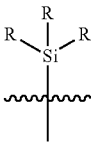

(b-6)

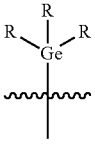

where

R is: a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms, and when a plurality of R are present, the plurality of R being mutually the same or different.]

[2. The organic electroluminescence device according to claim 1, wherein B in the formula (1) is represented by one of formulae (2), (3), (4), (5) and (6) below, (2)

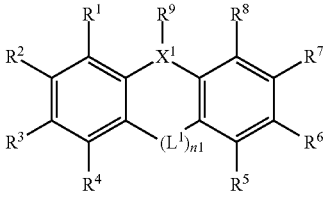

where: $R^1$ and $R^9$ each independently represent:

a hydrogen atom;

a substituted or unsubstituted aryl group having 6 to 30 ring carbon atoms;

a substituted or unsubstituted heterocyclic group having 5 to 30 ring atoms;

a substituted or unsubstituted alkyl group having 1 to 30 carbon atoms, a substituted or unsubstituted alkylsilyl group having 3 to 30 carbon atoms;

a substituted or unsubstituted arylsilyl group having 6 to 60 ring carbon atoms;

a substituted or unsubstituted alkoxy group having 1 to 30 carbon atoms;

a substituted or unsubstituted aryloxy group having 6 to 30 ring carbon atoms;

a substituted or unsubstituted alkylamino group having 2 to 30 carbon atoms;

a substituted or unsubstituted arylamino group having 6 to 60 ring carbon atoms;

a substituted or unsubstituted alkylthio group having 1 to 30 carbon atoms; or a substituted or unsubstituted arylthio group having 6 to 30 ring carbon atoms, at least one of the combinations of $R^1$ and $R^2$, $R^2$ and $R^3$, $R^3$ and $R^4$, $R^5$ and $R^6$, $R^6$ and $R^7$, $R^7$ and $R^8$, $R^8$ and $R^9$ and $R^9$ and $R^1$ optionally forming a saturated or unsaturated ring structure;

$L^1$ is a linking group selected from formulae (21) to (27) below, n1 represents an integer in a range from 1 to 3, and, when n1 is 2 or 3, plural $L^1$ are mutually the same or different, and $X^1$ is a linking group selected from formulae (41) to (45) below, (21)

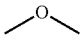

(22)

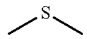

(23)

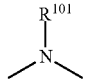

(24)

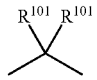

(25)

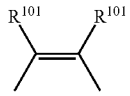

(26)

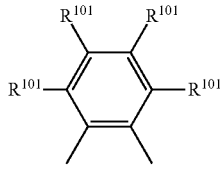

(27)

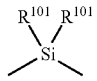

where, in the formulae (23) to (27), $R^{101}$ is the same as $R^1$ to $R^9$ in the formula (2), with a proviso that, in the formula (2), one of $R^1$ to $R^9$ or one of $R^{101}$ is a single bond to be bonded to L, and when a plurality of $R^{101}$ are present, the plurality of $R^{101}$ are mutually the same or different, (41)

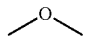

(42)

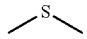

(43)

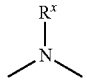

(44)

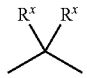

(45)

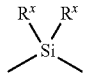

where, in the formulae (43) to (45), $R^x$ represents:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms, and when a plurality of $R^x$ are present, the plurality of $R^x$ are mutually the same or different, (3)

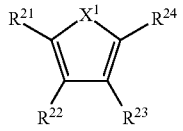

where, in the above formula (3), $R^{21}$ to $R^{24}$ are the same as $R^1$ to $R^9$ in the formula (2), one of the combinations of $R^{21}$ and $R^{22}$, $R^{22}$ and $R^{23}$, and $R^{23}$ and $R^{24}$ optionally forming a saturated or unsaturated cyclic structure; and $X^1$ is a linking group selected from the formulae (41) to (45), with a proviso that, in the above formula (3), one of $R^{21}$ to $R^{24}$ and $R^x$ is a single bond to be bonded to L, (4)

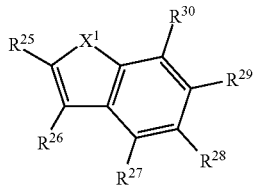

where, in the formula (4):

$R^{25}$ to $R^{30}$ represent the same as $R^1$ to $R^9$ in the formula (2), one of the combinations of $R^{25}$ and $R^{26}$, $R^{27}$ and $R^{28}$, $R^{28}$ and $R^{29}$, and $R^{29}$ and $R^{30}$ optionally forming a saturated or unsaturated cyclic structure; and $X^1$ is a linking group selected from the formulae (41) to (45), with a proviso that, in the above formula (4), one of $R^{25}$ to $R^{30}$ and $R^x$ is a single bond to be bonded to L, (5)

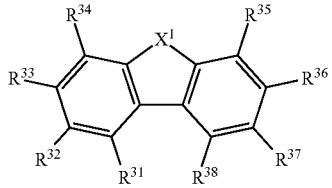

where, in the formula (5):

$R^{31}$ to $R^{38}$ are the same as $R^1$ to $R^9$ in the formula (2), one of the combinations of $R^{31}$ and $R^{32}$, $R^{32}$ and $R^{33}$, $R^{33}$ and $R^{34}$, and $R^{35}$ and $R^{36}$, $R^{36}$ and $R^{37}$, and $R^{37}$ and $R^{38}$ optionally forming a saturated or unsaturated cyclic structure; and $X^1$ is a linking group selected from the formulae (41) to (45), with a proviso that, in the above formula (5), one of $R^{31}$ to $R^{38}$ and $R^x$ is a single bond to be bonded to L, $$(Z^b)_r—Ar^b— \quad (6)$$

where, in the formula (6):

$Ar^b$ represents a substituted or unsubstituted aryl group having 6 to 30 ring carbon atoms;

Zb represents:

a substituted or unsubstituted tertiary alkyl group having 4 to 30 carbon atoms;

a substituted or unsubstituted alkylsilyl group having 3 to 30 carbon atoms;

a substituted or unsubstituted arylsilyl group having 6 to 60 ring carbon atoms;

a substituted or unsubstituted alkoxy group having 1 to 30 carbon atoms;

a substituted or unsubstituted aryloxy group having 6 to 30 ring carbon atoms;

a substituted or unsubstituted alkylamino group having 2 to 60 carbon atoms;

a substituted or unsubstituted arylamino group having 6 to 60 ring carbon atoms;

a substituted or unsubstituted alkylthio group having 1 to 30 carbon atoms; or a substituted or unsubstituted arylthio group having 6 to 30 ring carbon atoms, r is an integer in a range from 1 to 5 representing the number of a substituent(s) of $Z^b$ directly bonded to $A^b$, and a plurality of $Z^b$ being mutually the same or different when r is 2 or more.]

[3. The organic electroluminescence device according to claim 2, wherein the formula (2) is represented by a formula (2a) below, (2a)

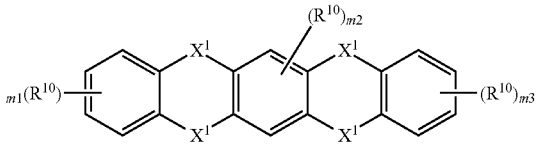

where, $R^{10}$ is the same as $R^1$ to $R^9$ in the formula (2), m1 and m3 represent an integer in a range from 0 to 4, m2 represents an integer in a range from 0 to 2, plural $R^{10}$ being mutually the same or different, and $X^1$ is a linking group selected from the formulae (41) to (45), plural $X^1$ being mutually the same or different, with a proviso that, in the formula (2a), one of $R^{10}$ and $R^x$ in the formulae (43) to (45) is a single bond to be bonded to L.]

[4. The organic electroluminescence device according to claim 2, wherein at least one of $R^{31}$ to $R^{38}$ in the formula (5) is represented by a formula (51) below, (51)

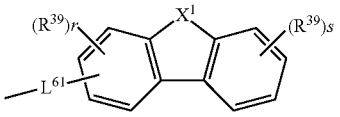

where: $R^{39}$ represents the same as $R^1$ to $R^9$ in the formula (2), r represents an integer in a range from 0 to 3 and S represents an integer in a range from 0 to 4, plural $R^{39}$ being mutually the same or different;

$X^1$ is a linking group selected from the formulae (41) to (45), $L^{61}$ represents a single bond or a linking group, and the linking group is:

a substituted or unsubstituted aryl group having 6 to 30 ring carbon atoms;

a substituted or unsubstituted heterocyclic group having 5 to 30 ring atoms; or a group derived from a group formed by mutually bonding two to five of the substituted or unsubstituted aryl group having 6 to 30 ring carbon atoms and/or the substituted or unsubstituted heterocyclic group having 5 to 30 ring atoms, the mutually bonded groups being mutually the same or different.]

[5. The organic electroluminescence device according to claim 1, wherein

A in the formula (1) is represented by one of formulae (8), (9), (10), (11), (12), (13) and (14) below, (8)

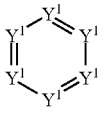

where, in the formula (8): two to four of $Y^1$ are a nitrogen atom, one of $Y^1$ is a carbon atom bonded to L and the rest of $Y^1$ is $CR^y$;

when the formula (8) includes a plurality of $R^y$, the plurality of $R^y$ independently represent: a hydrogen atom;

a fluorine atom;

a cyano group;

a nitro group;

a substituted or unsubstituted aryl group having 6 to 30 ring carbon atoms;

a substituted or unsubstituted heterocyclic group having 5 to 30 ring atoms;

a substituted or unsubstituted alkyl group having 1 to 30 carbon atoms;

a substituted or unsubstituted alkylcarbonyl group having 1 to 30 carbon atoms;

a substituted or unsubstituted arylcarbonyl group having 6 to 30 ring carbon atoms;

a substituted or unsubstituted alkylsulfinyl group having 1 to 30 carbon atoms;

a substituted or unsubstituted arylsulfinyl group having 6 to 30 ring carbon atoms;

a substituted or unsubstituted alkylphosphinyl group having 2 to 60 carbon atoms;

a substituted or unsubstituted arylphosphinyl group having 6 to 60 ring carbon atoms;

a substituted or unsubstituted alkylsulfonyl group having 1 to 30 carbon atoms;

a substituted or unsubstituted arylsulfonyl group having 6 to 30 ring carbon atoms;

a substituted or unsubstituted alkylsilyl group having 3 to 60 carbon atoms;

a substituted or unsubstituted arylsilyl group having 8 to 60 ring carbon atoms;

a substituted or unsubstituted alkoxy group having 1 to 30 carbon atoms; or a substituted or unsubstituted aryloxy group having 6 to 30 ring carbon atoms; and adjacent two $Y^1$ optionally form a saturated or unsaturated cyclic structure when the adjacent two $Y^1$ are $CR^y$, (9)

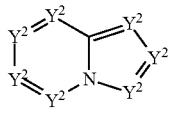

where, in the formula (9), $Y^2$ is the same as the other $Y^1$ in the formula (8), (10)

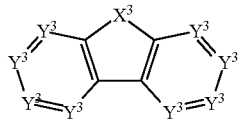

(11)

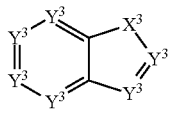

(12)

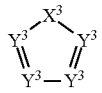

where, in the formulae (10), (11) and (12):

$Y^3$ represents the same as $Y^1$ in the formula (8); and $X^3$ is a linking group selected from formulae (41) to (45) below, (41)

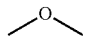

(42)

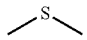

(43)

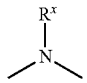

(44)

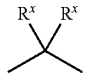

(45)

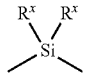

where, in the above formulae (43) to (45):

$R^x$ independently represents:

a hydrogen atom;

a substituted or unsubstituted aryl group having 6 to 30 carbon atoms;

a substituted or unsubstituted heterocyclic group having 5 to 30 ring atoms; or a substituted or unsubstituted alkyl group having 1 to 30 carbon atoms, and when a plurality of $R^x$ are present, the plurality of $R^x$ are mutually the same or different, (13)

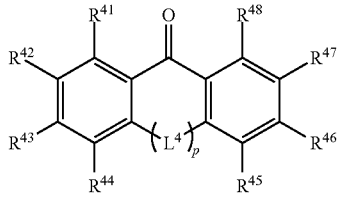

where, in the formula (13):

one of $R^{41}$ to $R^{48}$ is a single bond to be bonded to L;

the rest of $R^{41}$ to $R^{48}$ represent the same as $R^y$ in the formula (8);

$L^4$ is a linking group selected from formulae (131) to (136) below; and p represents an integer in a range from 1 to 3, a plurality of $L^4$ being mutually the same or different when p is 2 or 3, (131)

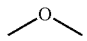

(132)

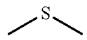

(133)

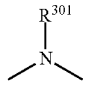

(134)

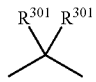

(135)

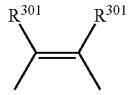

(136)

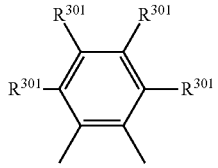

where, in the above formulae (133) to (136):

each of $R^{301}$ independently represents:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms, and when a plurality of $R^{301}$ are present, the plurality of $R^{301}$ are mutually the same or different, $$—Ar^a—(Z^a)_q \quad (14)$$

where, in the formula (14):

$Ar^a$ represents:

a substituted or unsubstituted aryl group having 6 to 30 ring carbon atoms, or a substituted or unsubstituted heterocyclic group having 5 to 30 ring atoms;

$Zr^a$ represents:

a fluorine atom;

a cyano group;

a nitro group;

a substituted or unsubstituted alkylcarbonyl group having 1 to 20 carbon atoms;

a substituted or unsubstituted arylcarbonyl group having 6 to 30 ring carbon atoms;

a substituted or unsubstituted alkylsulfinyl group having 1 to 20 carbon atoms;

a substituted or unsubstituted arylsulfinyl group having 6 to 30 ring carbon atoms;

a substituted or unsubstituted alkylphosphinyl group having 2 to 60 carbon atoms;

a substituted or unsubstituted arylphosphinyl group having 6 to 60 ring carbon atoms;

a substituted or unsubstituted alkylsulfonyl group having 1 to 30 carbon atoms; or a substituted or unsubstituted arylsulfonyl group having 6 to 30 ring carbon atoms;

q is an integer in a range from 1 to 5 representing the number of a substituent(s) of $Z^a$ directly bonded to $Ar^a$; and a plurality of $Z^a$ are mutually the same or different when q is 2 or more.]

[6. The organic electroluminescence device according to claim 1, wherein the second material in the form of the fluorescent dopant material is represented by a formula (20) below, (20)

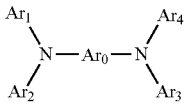

where, in the formula (20):

$Ar_0$ is a substituted or unsubstituted divalent fused aromatic hydrocarbon group having 10 to 50 ring carbon atoms; and $Ar_1$ to $Ar_4$ each independently represent:

a substituted or unsubstituted aryl group having 6 to 30 ring carbon atoms;

a substituted or unsubstituted heterocyclic group having 5 to 30 ring atoms;

a substituted or unsubstituted alkyl group having 6 to 30 carbon atoms; or a substituted or unsubstituted aralkyl group having 7 to 30 carbon atoms.]

[7. The organic electroluminescence device according to claim 1, wherein the organic electroluminescence device exhibits a delayed fluorescence ratio larger than 37.5%.]

[8. The organic electroluminescence device according to claim 1, wherein the organic electroluminescence device exhibits a residual strength ratio larger than 36.0% after an elapse of 1 μs after voltage removal in a transitional EL measurement.]

[9. The organic electroluminescence device according to claim 1, wherein a half bandwidth of a photoluminescence spectrum of the first material is 50 nm or more.]

[10. An organic electroluminescence device comprising:

a cathode;

an anode; and an organic thin-film layer disposed between the cathode and the anode, the organic thin-film layer having one or more layers comprising an emitting layer, the emitting layer comprising a first material represented by a formula (1) below and a second material in a form of a dopant material, with a proviso that the dopant material is not a heavy metal complex, (1)

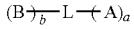

where, in the formula (1):

A is a group having a partial structure selected from formulae (a-1) to (a-7) below;

B is a group having a partial structure selected from formulae (b-1) to (b-6) below;

L represents a single bond or a linking group;

the linking group is:

a substituted or unsubstituted aryl group having 6 to 30 ring carbon atoms;

a substituted or unsubstituted heterocyclic group having 5 to 30 ring atoms; or a group derived from a group formed by mutually bonding two to five of the substituted or unsubstituted aryl group having 6 to 30 ring carbon atoms and/or the substituted or unsubstituted heterocyclic group having 5 to 30 ring atoms, the mutually bonded groups being mutually the same or different;

a is an integer in a range from 1 to 5 representing the number of a substituent(s) of A directly bonded to L;

a plurality of A being mutually the same or different when a is 2 or more; and b is an integer in a range from 1 to 5 representing the number of a substituent(s) of B directly bonded to L, a plurality of B being mutually the same or different when b is 2 or more, (a-1)

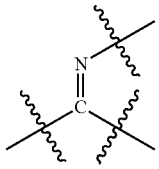

(a-2)

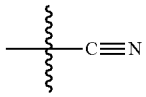

(a-3)

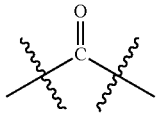

(a-4)

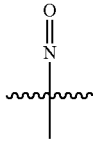

(a-5)

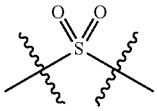

(a-6)

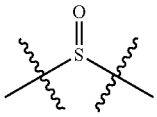

(a-7)

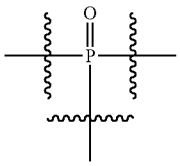

(b-1)

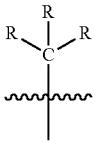

(b-2)

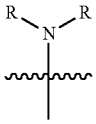

(b-3)

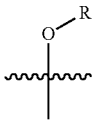

(b-4)

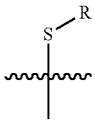

(b-5)

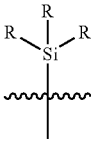

(b-6)

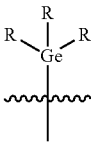

where, in the formulae (b-1) to (b-6):

R is:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms; and when a plurality of R are present, the plurality of R are mutually the same or different.]

*11. An organic electroluminescence device, comprising:*

*a cathode;*

*an anode; and*

*an organic thin-film layer disposed between the cathode and the anode, the organic thin-film layer having one or more layers comprising an emitting layer, the emitting layer comprising a first material of formula (1e) below and a second material in a form of a fluorescent dopant material,*

*(1e)*

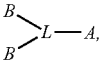

*where, in the formula (1e):*

*L is a substituted or unsubstituted phenyl group;*

*A is a group of formula (a-2)*

*(a-2)*

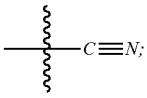

*B is independently a group of formula (5):*

*(5)*

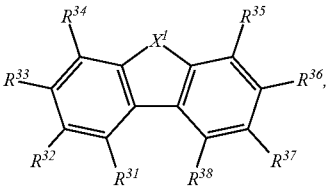

where, in the formula (5):

$R^{31}$ to $R^{38}$ are independently a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted alkylthio group having 1 to 30 carbon atoms, or a substituted or unsubstituted arylthio group having 6 to 30 ring carbon atoms; and $X^1$ is a linking group of formula (41), (42), (43), or (45), with a proviso that, in the above formula (5), one of $R^{31}$ to $R^{38}$ or $R^x$ in each B is a single bond directly bonded to L, (41)

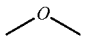

(42)

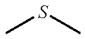

(43)

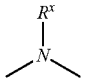

(45)

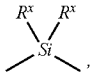

where, in the formulae (43) to (45), $R^x$ is independently:

a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms;

wherein, in at least one of two B that are groups of the formula (5) in the formula (1e), one of the combinations of $R^{31}$ and $R^{32}$, $R^{32}$ and $R^{33}$, $R^{33}$ and $R^{34}$, $R^{35}$ and $R^{36}$, $R^{36}$ and $R^{37}$, and $R^{37}$ and $R^{38}$ forms a saturated or unsaturated cyclic structure, wherein the first material represented by the formula (1e) does not comprise a structure of formula (51) in a molecule:

(51)

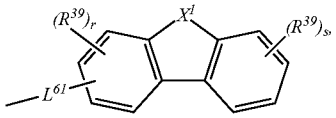

where, in the formula (51):

$R^{39}$ is independently:

a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms;

r is an integer in a range from 0 to 3;

S is an integer in a range from 0 to 4;

$X^1$ is a linking group of formula (44) below:

(44)

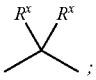

where, in the formula (44), $R^x$ is independently:

a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms;

$L^{61}$ is a single bond or a linking group selected from the group consisting of:

a substituted or unsubstituted aryl group having 6 to 30 ring carbon atoms, a substituted or unsubstituted heterocyclic group having 5 to 30 ring atoms, and a group derived from a group formed by mutually bonding two to five of the substituted or unsubstituted aryl group having 6 to 30 ring carbon atoms and/or the substituted or unsubstituted heterocyclic group haying 5 to 30 ring atoms, the mutually bonded groups being mutually the same or different; and wherein the first material does not comprise a substituted or unsubstituted arylamino group having 6 to 30 ring carbon atoms in a molecule;

wherein the first material does not include an arylamino group in a foil of —$N(Rw)_2$ in a molecule, Rw being a substituted or unsubstituted aryl group having 6 to 30 ring carbon atoms;

wherein the first material does not include a group of formula (b-2) in a molecule, (b-2)

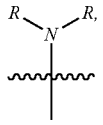

in which R is a substituted or unsubstituted heterocyclic group having 5 to 30 ring atoms;

wherein the first material does not include a group of formula (2b), (2b)

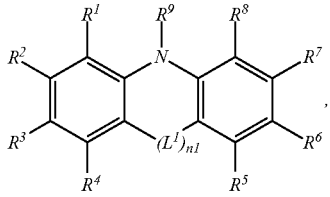

in a molecule, where, in the formula (2b), $R^1$ to $R^9$ are independently:

a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted alkylthio group having 1 to 30 carbon atoms, or a substituted or unsubstituted arylthio group having 6 to 30 ring carbon atoms, at least one of the combinations of $R^1$ and $R^2$, $R^2$ and $R^3$, $R^3$ and $R^4$, $R^5$ and $R^6$, $R^6$ and $R^7$, $R^7$ and $R^8$, $R^8$ and $R^9$ and $R^9$ and $R^1$ optionally forming a saturated or unsaturated ring structure:

$L^1$ is independently a linking group selected from formulae (21) to (27) below, (21)

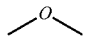

(22)

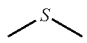

(23)

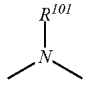

(24)

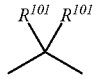

-continued (25)

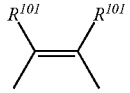

(26)

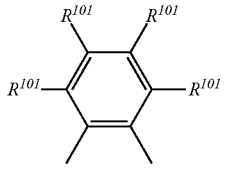

(27)

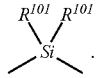

where, in the formulae (23) to (27), $R^{101}$ is independently any group as defined for $R^1$ to $R^9$ in the formula (2b), with a proviso that, in the formula (2b), one of $R^1$ to $R^9$ or one of $R^{101}$ is a single bond to be bonded to L, n1 is an integer in a range from 1 to 3, and, when n1 is 2 or 3, plural $L^1$ are mutually the same or different, wherein the first material does not include an azacarbazolyl group; and wherein L of the first material represented by the formula (1e) does not include an anthryl group;

wherein the first material of formula (1e) does not have a structure of formula (101), (101)

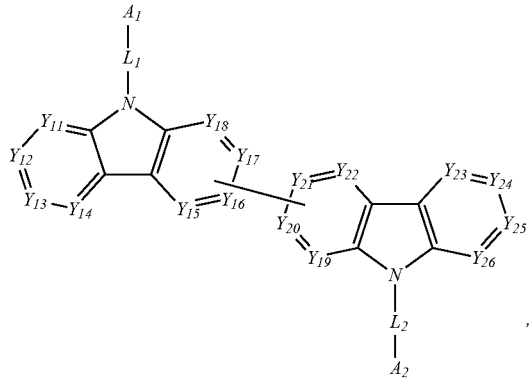

where, in the formula (101), $A_1$ and $A_2$ are independently:

a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, a substituted or unsubstituted alkylsilyl group having 3 to 60 carbon atoms, or a substituted or unsubstituted arylsilyl group having 8 to 30 ring carbon atoms, $Y_{11}$ to $Y_{14}$ and $Y_{23}$ to $Y_{26}$ in the formula (101) are independently C(R) or a nitrogen atom, $Y_{15}$ to $Y_{18}$ are independently a nitrogen atom, C(R) or a carbon atom bonded with at least one of $Y_{19}$ to $Y_{22}$, and $Y_{19}$ to $Y_{22}$ are independently C(R), a nitrogen atom or a carbon atom bonded with at least one of $Y_{15}$ to $Y_{18}$, with a proviso that R is independently a hydrogen atom or a substituent, the substituent for R being the same as the substituents for $A_1$ and $A_2$, $L_1$ and $L_2$ in the formula (101) are independently a single bond, a substituted or unsubstituted divalent aromatic hydrocarbon group having 6 to 30 ring carbon atoms, a substituted or unsubstituted divalent heterocyclic group having 5 to 30 ring atoms or a group formed by mutually bonding the substituted or unsubstituted divalent aromatic hydrocarbon group having 6 to 30 ring carbon atoms and/or the substituted or unsubstituted divalent heterocyclic group having 5 to 30 ring atoms;

wherein, when $X^1$ in the formula (5) is of the formula (43), $R^x$ is a single bond directly bonded to L; and wherein the first material does not comprise a partial structure of formula (a-1) in a molecule (a-1)

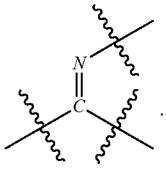

12. The device of claim 11, wherein the emitting layer does not comprise a heavy metal complex.

13. The device of claim 11, wherein, in B, at least one of $R^{31}$ to $R^{38}$ in the formula (5) has a structure of formula (51) below, (51)

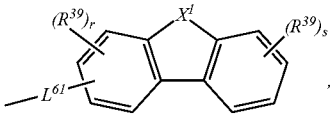

where, in the formula (51), $R^{39}$ is independently any group as defined for $R^1$ to $R^9$ in the formula (2b), r is an integer in a range from 0 to 3, and S is an integer in a range from 0 to 4;

$X^1$ is a linking group represented by the formula (41), (42), (43), or (45), $L^{61}$ is a single bond or a linking group, the linking group being:

a substituted or unsubstituted aryl group having 6 to 30 ring carbon atoms;

a substituted or unsubstituted heterocyclic group having 5 to 30 ring atoms; or a group derived from a group formed by mutually bonding two to five of the substituted or unsubstituted aryl group having 6 to 30 ring carbon atoms and/or the substituted or unsubstituted heterocyclic group having 5 to 30 ring atoms, the mutually bonded groups being mutually the same or different.

14. The device of claim 11, wherein the second material in the form of the fluorescent dopant material has a structure of formula (20) below, (20)

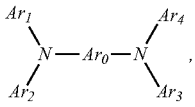

where, in the formula (20):

$Ar_0$ is a substituted or unsubstituted divalent fused aromatic hydrocarbon group having 10 to 50 ring carbon atoms; and $Ar_1$ to $Ar_4$ are independently:

a substituted or unsubstituted aryl group having 6 to 30 ring carbon atoms;

a substituted or unsubstituted heterocyclic group having 5 to 30 ring atoms;

a substituted or unsubstituted alkyl group having 6 to 30 carbon atoms; or a substituted or unsubstituted aralkyl group having 7 to 30 carbon atoms.

15. The device of claim 11, exhibiting a delayed fluorescence ratio larger than 37.5%.

16. The device of claim 11, exhibiting a residual strength ratio larger than 36.0% after an elapse of 1 μs after voltage removal in a transitional EL measurement.

17. The device of claim 11, wherein a half bandwidth of a photoluminescence spectrum of the first material is 50 nm or more.

18. The device of claim 11, wherein $X^1$ is a linking group of the formula (43), and $R^x$ in the formula (43) is a single bond bonded with L.

19. The device of claim 11, wherein at least one of $R^{31}$ to $R^{38}$ has a structure of formula (51), (51)

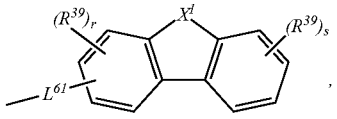

where, in the formula (51), $R^{39}$ is independently any group as defined for $R^1$ to $R^9$ in the formula (2b), r is an integer ranging from 0 to 3, S is an integer ranging from 0 to 4, $X^1$ is a linking group of the formula (43), and $L^{61}$ is a single bond or a linking group, the linking group being:

a substituted or unsubstituted aryl group having 6 to 30 ring carbon atoms;

a substituted or unsubstituted heterocyclic group having 5 to 30 ring atoms; or a group derived from a group formed by mutually bonding two to five of the substituted or unsubstituted aryl group having 6 to 30 ring carbon atoms and/or the substituted or unsubstituted heterocyclic croup having 5 to 30 ring atoms, the mutually bonded groups being the same or different.

20. The device of claim 19, wherein a plurality of $X^1$ are linking groups of the formula (43), and at least one of $R^x$ in the formula (43) is a single bond bonded with L.

21. The device of claim 11, wherein the fluorescent dopant material is selected from the group consisting of a bisarylamino naphthalene derivative, an aryl-substituted naphthalene derivative, a bisarylamino anthracene derivative, an aryl-substituted anthracene derivative, a bisarylamino pyrene derivative, an aryl-substituted pyrene derivative, a bisarylamino chrysene derivative, an aryl-substituted chrysene derivative, a bisarylamino fluoranthene derivative, an aryl-substituted fluoranthene derivative, an indenoperylene derivative, a pyrromethene boron complex compound, a compound having a pyrromethene skeleton or a metal complex thereof, a diketopyrrolopyrrole derivative, and a perylene derivative.

22. The device of claim 11, wherein the first material does not comprise a structure of formula (51A) in a molecule, (51A)

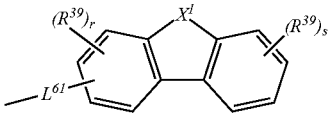

where, in the formula (51A), $R^{39}$ is independently any group as defined for $R^1$ to $R^9$ in the formula (2b), r is an integer in a range from 0 to 3, and S is an integer in a range from 0 to 4;

$X^1$ is a linking group of the formula (43), $L^{61}$ is a single bond or a linking group, the linking group being:

a substituted or unsubstituted aryl group having 6 to 30 ring carbon atoms;

a substituted or unsubstituted heterocyclic group having 5 to 30 ring atoms; or a group derived from a group formed by mutually bonding two to five of the substituted or unsubstituted aryl group having 6 to 30 ring carbon atoms and/or the substituted or unsubstituted heterocyclic group having 5 to 30 ring atoms, the mutually bonded groups being mutually the same or different.

23. The device of claim 11, wherein the first material does not comprise a partial structure of formula (b-5) in a molecule, (b-5)

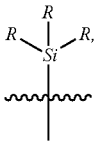

where, in the partial structure of the formula (b-5), R is independently:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms.

24. The device of claim 23, wherein the first material does not comprise a structure of formula (51C) in a molecule, (51C)

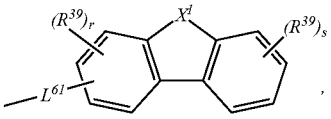

where, in the formula (51C), $R^{39}$ is independently:

a hydrogen atom;

a substituted or unsubstituted aryl group having 6 to 30 ring carbon atoms;

a substituted or unsubstituted heterocyclic group having 5 to 30 ring atoms;

a substituted or unsubstituted alkyl group having 1 to 30 carbon atoms, a substituted or unsubstituted alkylsilyl group having 3 to 30 carbon atoms;

a substituted or unsubstituted arylsilyl group having 6 to 60 ring carbon atoms;

a substituted or unsubstituted alkoxy group having 1 to 30 carbon atoms;

a substituted or unsubstituted aryloxy group having 6 to 30 ring carbon atoms;

a substituted or unsubstituted alkylamino group having 2 to 30 carbon atoms;

a substituted or unsubstituted arylamino group having 6 to 60 ring carbon atoms;

a substituted or unsubstituted alkylthio croup having 1 to 30 carbon atoms; or a substituted or unsubstituted arylthio group having 6 to 30 ring carbon atoms;

r is an integer in a range from 0 to 3, and

S is an integer in a range from 0 to 4;

$X^1$ is a linking group of the formula (43):

(43)

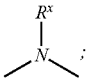

where, in the formula (43), $R^x$ is independently:

a hydrogen atom, a substituted or unsubstituted aryl group having 6 to 30 carbon atoms, a substituted or unsubstituted heterocyclic group having 5 to 30 ring atoms, or a substituted or unsubstituted alkyl group having 1 to 30 carbon atoms;

$L^{61}$ is a single bond or a linking group, the linking group being:

a substituted or unsubstituted aryl group haying 6 to 30 ring carbon atoms;

a substituted or unsubstituted heterocyclic group having 5 to 30 ring atoms; or a group derived from a group formed by mutually bonding two to five of the substituted or unsubstituted aryl group having 6 to 30 ring carbon atoms and/or the substituted or unsubstituted heterocyclic group having 5 to 30 ring atoms, the mutually bonded groups being mutually the same or different.

25. The device of claim 11, wherein the first material does not comprise a structure of formula (51D) in a molecule, (51D)

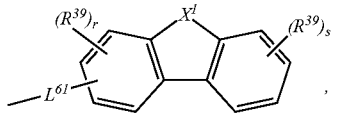

where, in the formula (51D):

$R^{39}$ is independently a substituted or unsubstituted arylamino group having 6 to 60 ring carbon atoms, r is an integer in a range from 0 to 3 and S is an integer in a range from 0 to 4, with a proviso that at least one of r and S is 1 or more;

$X^1$ is a linking group of the formula (43), $L^{61}$ is a single bond or a linking group, the linking group being:

a substituted or unsubstituted aryl group having 6 to 30 ring carbon atoms;

a substituted or unsubstituted heterocyclic group having 5 to 30 ring atoms; or a group derived from a group formed by mutually bonding two to five of the substituted or unsubstituted aryl group having 6 to 30 ring carbon atoms and/or the substituted or unsubstituted heterocyclic croup having 5 to 30 rim atoms, the mutually bonded groups being mutually the same or different.

26. The device of claim 11, wherein the first material does not comprise in a molecule (i) and (ii):

(i) a structure of the formula (2), (2)

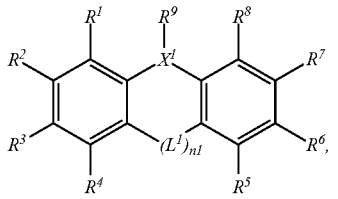

where, in the formula (2), $R^1$ to $R^9$ are independently:

a hydrogen atom;

a substituted or unsubstituted aryl group having 6 to 30 ring carbon atoms;

a substituted or unsubstituted heterocyclic group having 5 to 30 ring atoms;

a substituted or unsubstituted alkyl group having 1 to 30 carbon atoms, a substituted or unsubstituted alkylsilyl group having 3 to 30 carbon atoms;

a substituted or unsubstituted arylsilyl group having 6 to 60 ring carbon atoms;

a substituted or unsubstituted alkoxy group having 1 to 30 carbon atoms;

a substituted or unsubstituted aryloxy group having 6 to 30 ring carbon atoms;

a substituted or unsubstituted alkylamino group having 2 to 30 carbon atoms;

a substituted or unsubstituted alkylthio group having 1 to 30 carbon atoms; or a substituted or unsubstituted arylthio group having 6 to 30 ring carbon atoms, at least one of the combinations of $R^1$ and $R^2$, $R^2$ and $R^3$, $R^3$ and $R^4$, $R^5$ and $R^6$, $R^6$ and $R^7$, $R^7$ and $R^8$, $R^8$ and $R^9$ and $R^9$ and $R^1$ optionally forming a saturated or unsaturated ring structure;

$L^1$ is a linking group of formula (23), (23)

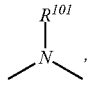

where, in the formula (23), $R^{101}$ is any group as defined for $R^1$ to $R^9$ in the formula (2), with a proviso that, in the formula (2), one of $R^1$ to $R^9$ or $R^{101}$ is a single bond to be bonded to L, n1 is 1, and $X^1$ is a linking group of formula (44), (44)

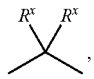

wherein, in the formula (44), $R^x$ is independently:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms, and (ii) a partial structure of formula (b-5), (b-5)

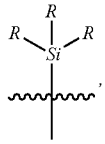

where, in the formula (b-5), R is independently:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms.

27. The device of claim 24, wherein the first material does not comprise in a molecule (i) and (ii):

(i) a structure of the formula (2), (2)

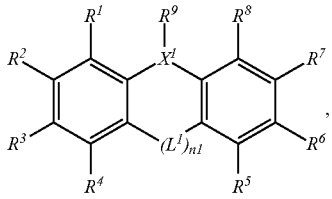

where, in the formula (2), $R^1$ to $R^9$ are independently:

a hydrogen atom;

a substituted or unsubstituted aryl group having 6 to 30 ring carbon atoms;

a substituted or unsubstituted heterocyclic group having 5 to 30 ring atoms;

a substituted or unsubstituted alkyl group having 1 to 30 carbon atoms, a substituted or unsubstituted alkylsilyl group having 3 to 30 carbon atoms;

a substituted or unsubstituted arylsilyl group having 6 to 60 ring carbon atoms;

a substituted or unsubstituted alkoxy group having 1 to 30 carbon atoms;

a substituted or unsubstituted aryloxy group having 6 to 30 ring carbon atoms:

a substituted or unsubstituted alkylamino group having 2 to 30 carbon atoms;

a substituted or unsubstituted alkylthio group having 1 to 30 carbon atoms; or a substituted or unsubstituted arylthio group having 6 to 30 ring carbon atoms, at least one of the combinations of $R^1$ and $R^2$, $R^2$ and $R^3$, $R^3$ and $R^4$, $R^5$ and $R^6$, $R^6$ and $R^7$, $R^7$ and $R^8$, $R^8$ and $R^9$ and $R^9$ and $R^1$ optionally forming a saturated or unsaturated ring structure;

$L^1$ is a linking group of formula (23), (23)

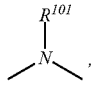

where, in the formula (23), $R^{101}$ is any group as defined for $R^1$ to $R^9$ in the formula (2), with a proviso that, in the formula (2), one of $R^1$ to $R^9$ or $R^{101}$ is a single bond to be bonded to L, n1 is 1, and $X^1$ is a linking group of formula (44) below, (44)

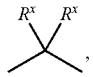

where, in the formula (44), $R^x$ is independently:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms; and (ii) a partial structure of formula (b-5), (b-5)

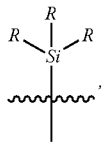

where, in the formula (b-5), R is independently:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms.

28. The device of claim 24, wherein the first material does not comprise in a molecule a structure of the formula (2), (2)

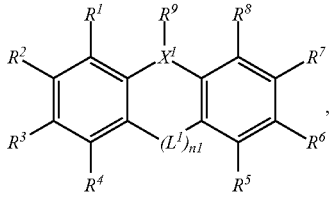

where, in the formula (2), $R^1$ to $R^9$ are independently:

a hydrogen atom;

a substituted or unsubstituted aryl group having 6 to 30 ring carbon atoms;

a substituted or unsubstituted heterocyclic group having 5 to 30 ring atoms;

a substituted or unsubstituted alkyl group having 1 to 30 carbon atoms, a substituted or unsubstituted alkylsilyl group having 3 to 30 carbon atoms;

a substituted or unsubstituted arylsilyl group having 6 to 60 ring carbon atoms;

a substituted or unsubstituted alkoxy group having 1 to 30 carbon atoms;

a substituted or unsubstituted aryloxy group having 6 to 30 ring carbon atoms:

a substituted or unsubstituted alkylamino group having 2 to 30 carbon atoms;

a substituted or unsubstituted alkylthio group having 1 to 30 carbon atoms; or a substituted or unsubstituted arylthio group having 6 to 30 ring carbon atoms, at least one of the combinations of $R^1$ and $R^2$, $R^2$ and $R^3$, $R^3$ and $R^4$, $R^5$ and $R^6$, $R^6$ and $R^7$, $R^7$ and $R^8$, $R^8$ and $R^9$ and $R^9$ and $R^1$ optionally forming a saturated or unsaturated ring structure;

$L^1$ is a linking group of formula (23), (23)

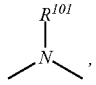

where, in the formula (23), $R^{101}$ is any group as defined for $R^1$ to $R^9$ in the formula (2), with a proviso that, in the formula (2), one of $R^1$ to $R^9$ or $R^{101}$ is a single bond to be bonded to L, n1 is 1, and $X^1$ is a linking group of formula (44), (44)

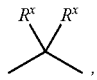

wherein, in the formulae (44), $R^x$ is independently:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms.

29. The device of claim 24, wherein the first material does not comprise in a molecule (i) and (ii):

(i) a structure of the formula (2), (2)

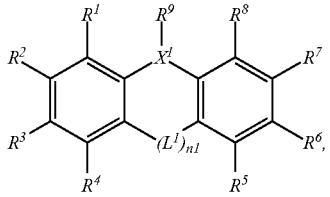

where, in the formula (2), $R^1$ to $R^9$ are independently:

a hydrogen atom;

a substituted or unsubstituted aryl group having 6 to 30 ring carbon atoms;

a substituted or unsubstituted heterocyclic group having 5 to 30 ring atoms;

a substituted or unsubstituted alkyl group having 1 to 30 carbon atoms, a substituted or unsubstituted alkylsilyl group having 3 to 30 carbon atoms;

a substituted or unsubstituted arylsilyl group having 6 to 60 ring carbon atoms, a substituted or unsubstituted alkoxy group having 1 to 30 carbon atoms;

a substituted or unsubstituted aryloxy group having 6 to 30 ring carbon atoms;

a substituted or unsubstituted alkylamino group having 2 to 30 carbon atoms;

a substituted or unsubstituted alkylthio group having 1 to 30 carbon atoms; or a substituted or unsubstituted arylthio group having 6 to 30 ring carbon atoms, at least one of the combinations of $R^1$ and $R^2$, $R^2$ and $R^3$, $R^3$ and $R^4$, $R^5$ and $R^6$, $R^{66}$ and $R^7$, $R^7$ and $R^8$, $R^8$ and $R^9$ and $R^9$ and $R^1$ optionally forming a saturated or unsaturated ring structure;

$L^1$ is a linking group of formula (23), (23)

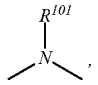

where, in the formula (23), $R^{101}$ is any group as defined for $R^1$ to $R^9$ in the formula (2), with a proviso that, in the formula (2), one of $R^1$ to $R^9$ or $R^{101}$ is a single bond to be bonded to L, n1 is 1, and $X^1$ is a linking group of formula (44), (44)

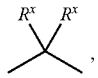

wherein, in the formulae (44), $R^x$ is independently:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms; and (ii) a partial structure of formula (b-5), (b-5)

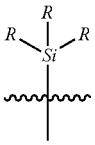

where, in the formula (b-5), R is independently:

a hydrogen atom;

a substituted or unsubstituted aryl group having 6 to 30 ring carbon atoms;

a substituted or unsubstituted heterocyclic group having 5 to 30 ring atoms; or a substituted or unsubstituted alkyl group having 1 to 30 carbon atoms.

30. The device of claim 14, wherein the emitting layer does not comprise a heavy metal complex.

31. The device of claim 15, wherein the emitting layer does not comprise a heavy metal complex.

32. The device of claim 16, wherein the emitting layer does not comprise a heavy metal complex.

33. The device of claim 17, wherein the emitting layer does not comprise a heavy metal complex.

34. The device of claim 26, wherein the emitting layer does not comprise a heavy metal complex.

35. The device of claim 27, wherein the emitting layer does not comprise a heavy metal complex.

36. The device of claim 28, wherein the emitting layer does not comprise a heavy metal complex.

37. The device of claim 29, wherein the emitting layer does not comprise a heavy metal complex.

38. The device of claim 11, wherein a difference $\Delta ST(H)$ between a singlet energy $EgS(H)$ of the first material and an energy gap $Eg_{77K}(H)$ of the first material at 77[K] satisfies a formula (2), $$\Delta ST(H)=EgS(H)-Eg_{77K}(H)<0.3\ [eV] \quad (2).$$

39. The device of claim 38, wherein the emitting layer does not comprise a heavy metal complex.

40. The device of claim 11, wherein the first material is a thermally activated delayed fluorescent compound.

41. The device of claim 40, wherein the emitting layer does not comprise a heavy metal complex.

42. The device of claim 11, wherein the emitting layer is not phosphorescent.

43. The device of claim 11, wherein $X^1$, in the group of the formula (5), is the linking group of the formula (41).

44. The device of claim 11, wherein the $X^1$, in the group of the formula (5), is the linking group of the formula (42).

45. The device of claim 11, wherein the $X^1$, in the group of the formula (5), is the linking group of the formula (43).

46. The device of claim 11, wherein the $X^1$, in the group of the formula (5), is the linking group of the formula (45).

47. The device of claim 11, wherein, in two B in the formula (1e), one of the combinations of $R^{31}$ and $R^{32}$, $R^{32}$ and $R^{33}$, $R^{33}$ and $R^{34}$, and $R^{35}$ and $R^{36}$, $R^{36}$ and $R^{37}$, and $R^{37}$ and $R^{38}$ forms a saturated or unsaturated cyclic structure.

48. The device of claim 11, wherein, in at least one of the two B in the formula (1e), $R^{31}$ and $R^{32}$ form a saturated or unsaturated cyclic structure.

49. The device of claim 11, wherein, in at least one of the two B in the formula (1e), $R^{32}$ and $R^{33}$ form a saturated or unsaturated cyclic structure.

50. The device of claim 11, wherein, in at least one of the two B in the formula (1e), $R^{33}$ and $R^{34}$ form a saturated or unsaturated cyclic structure.

51. The device of claim 11, wherein, in at least one of the two B in the formula (1e), $R^{35}$ and $R^{36}$ form a saturated or unsaturated cyclic structure.

52. The device of claim 11, wherein, in at least one of the two B in the formula (1e), $R^{36}$ and $R^{37}$ form a saturated or unsaturated cyclic structure.

53. The device of claim 11, wherein, in at least one of the two B in the formula (1e), $R^{37}$ and $R^{38}$ form a saturated or unsaturated cyclic structure.

54. An organic electroluminescence device, comprising:

a cathode;

an anode; and an organic thin-film layer disposed between the cathode and the anode, the organic thin-film layer having one or more layers comprising an emitting layer, the emitting layer comprising a first material of formula (1e) below and a second material in a form of a fluorescent dopant material, (1e)

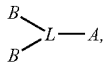

where, in the formula (1e):

L is a substituted or unsubstituted aryl group having 6 to 30 ring carbon atoms;

A is a group of formula (a-2)

(a-2)

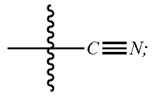

B is independently a group of formula (5):

(5)

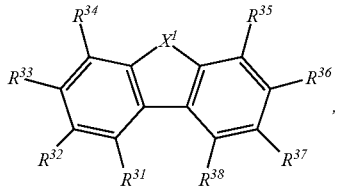

where, in the formula (5):

$R^{31}$ to $R^{38}$ are independently a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted alkylthio group having 1 to 30 carbon atoms, or a substituted or unsubstituted arylthio group having 6 to 30 ring carbon atoms, one of the combinations of $R^{31}$ and $R^{32}$, $R^{32}$ and $R^{33}$, $R^{33}$ and $R^{34}$, and $R^{35}$ and $R^{36}$, $R^{36}$ and $R^{37}$, and $R^{37}$ and $R^{38}$ optionally forming a saturated or unsaturated cyclic structure; and $X^1$ is a linking group of formula (45), with a proviso that, in the above formula (5), one of $R^{31}$ to $R^{38}$ or $R^x$ in each B is a single bond directly bonded to L, (45)

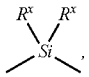

where $R^x$ is independently:

a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms;

wherein the first material represented by the formula (1e) does not comprise a structure of formula (51) in a molecule:

(51)

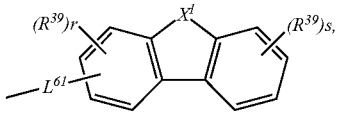

where, in the formula (51):

$R^{39}$ is independently:

a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms;

r is an integer in a range from 0 to 3;

S is an integer in a range from 0 to 4;

$X^1$ is a linking group of formula (44) below:

(44)

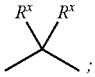

where, in the formula (44), $R^x$ is independently:

a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms;

$L^{61}$ is a single bond or a linking group selected from the group consisting of a substituted or unsubstituted aryl group having 6 to 30 ring carbon atoms, a substituted or unsubstituted heterocyclic group having 5 to 30 ring atoms, and a group derived from a group formed by mutually bonding two to five of the substituted or unsubstituted aryl group having 6 to 30 ring carbon atoms and/or the substituted or unsubstituted heterocyclic group having 5 to 30 ring atoms, the mutually bonded groups being mutually the same or different; and wherein the first material does not comprise a substituted or unsubstituted arylamino group having 6 to 30 ring carbon atoms in a molecule;

wherein the first material does not include an arylamino group in a form of $—N(Rw)_2$ in a molecule, Rw being a substituted or unsubstituted aryl group having 6 to 30 ring carbon atoms;

wherein the first material does not include a group of formula (b-2) in a molecule, (b-2)

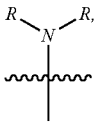

in which R is a substituted or unsubstituted heterocyclic group having 5 to 30 ring atoms;

wherein the first material does not include a group of formula (2b), (2b)

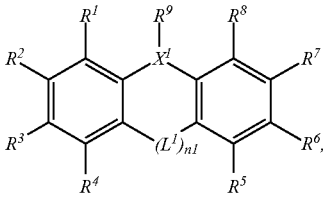

in a molecule, where, in the formula (2b), $R^1$ to $R^9$ are independently:

a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted alkylthio group having 1 to 30 carbon atoms, or a substituted or unsubstituted arylthio group having 6 to 30 ring carbon atoms, at least one of the combinations of $R^1$ and $R^2$, $R^2$ and $R^3$, $R^3$ and $R^4$, $R^5$ and $R^6$, $R^6$ and $R^7$, $R^7$ and $R^8$, $R^8$ and $R^9$ and $R^9$ and $R^1$ optionally forming a saturated or unsaturated ring structure;

$L^1$ is independently a linking group selected from formulae (21) to (27) below, (21)

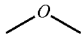

(22)

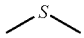

(23)

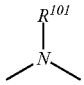

(24)

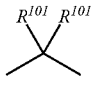

(25)

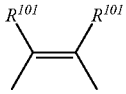

(26)

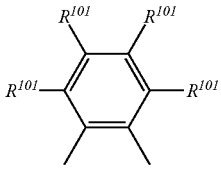

-continued (27)

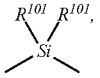

where, in the formulae (23) to (27), $R^{101}$ is independently any group as defined for $R^1$ to $R^9$ in the formula (2b), with a proviso that, in the formula (2b), one of $R^1$ to $R^9$ or one of $R^{101}$ is a single bond to be bonded to L, n1 is an integer in a range from 1 to 3, and, when n1 is 2 or 3, plural $L^1$ are mutually the same or different, wherein the first material does not include an azacarbazolyl group; and wherein L of the first material represented by the formula (1e) does not include an anthryl group;

wherein the first material of formula (1e) does not have a structure of formula (101), (101)

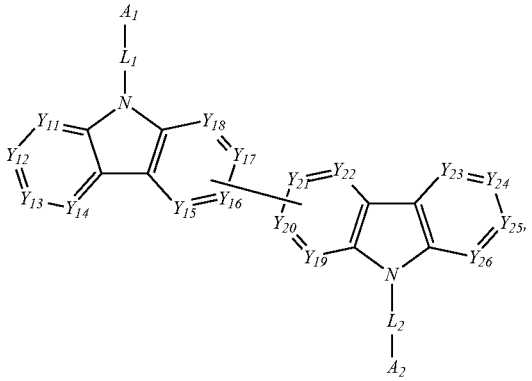

where, in the formula (101), $A_1$ and $A_2$ are independently:

a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, a substituted or unsubstituted alkylsilyl group having 3 to 60 carbon atoms, or a substituted or unsubstituted arylsilyl group having 8 to 30 ring carbon atoms, $Y_{11}$ to $Y_{14}$ and $Y_{23}$ to $Y_{26}$ in the formula (101) are independently C(R) or a nitrogen atom, $Y_{15}$ to $Y_{18}$ are independently a nitrogen atom, C(R) or a carbon atom bonded with at least one of $Y_{19}$ to $Y_{22}$, and $Y_{19}$ to $Y_{22}$ are independently C(R), a nitrogen atom or a carbon atom bonded with at least one of $Y_{15}$ to $Y_{18}$, with a proviso that R is independently a hydrogen atom or a substituent, the substituent for R being the same as the substituents for $A_1$ and $A_2$, $L_1$ and $L_2$ in the formula (101) are independently a single bond, a substituted or unsubstituted divalent aromatic hydrocarbon group having 6 to 30 ring carbon atoms, a substituted or unsubstituted divalent heterocyclic group having 5 to 30 ring atoms or a group formed by mutually bonding the substituted or unsubstituted divalent aromatic hydrocarbon group having 6 to 30 ring carbon atoms and/or the substituted or unsubstituted divalent heterocyclic group having 5 to 30 ring atoms;

wherein, when $X^1$ in the formula (5) is of the formula (43), $R^x$ is a single bond directly bonded to L; and wherein the first material does not comprise a partial structure of formula (a-1) in a molecule (a-1)

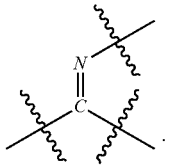

* * * * *